United States Patent [19]
Engel et al.

[11] Patent Number: 6,140,273
[45] Date of Patent: Oct. 31, 2000

[54] SUBSTITUTED 2-BENZOYLCYCLOHEXANE-1,3-DIONES

[75] Inventors: Stefan Engel, Idstein; Ernst Baumann, Dudenhofen; Wolfgang von Deyn, Neustadt; Regina Luise Hill, Speyer; Uwe Kardorff, Mannheim; Guido Mayer, Neustadt; Martina Otten, Ludwigshafen; Joachim Rheinheimer, Ludwigshafen; Oliver Wagner, Ludwigshafen; Matthias Witschel, Ludwigshafen; Ulf Misslitz, Neustadt; Helmut Walter, Obrigheim; Karl-Otto Westphalen, Speyer, all of Germany

[73] Assignee: BASF Aktiengesellschaft, Ludwigshafen, Germany

[21] Appl. No.: 09/423,076
[22] PCT Filed: Apr. 24, 1998
[86] PCT No.: PCT/EP98/02448
  § 371 Date: Nov. 2, 1999
  § 102(e) Date: Nov. 2, 1999
[87] PCT Pub. No.: WO98/50377
  PCT Pub. Date: Nov. 12, 1998

[30] Foreign Application Priority Data

May 7, 1997 [DE] Germany .............. 197 26 711

[51] Int. Cl.$^7$ .................. A01N 43/02; C07D 305/08; C07D 301/30; C07D 303/32
[52] U.S. Cl. .................. 504/291; 549/510; 549/511; 549/539; 549/556
[58] Field of Search .............. 504/291; 549/510, 549/511, 539, 556

[56] References Cited

U.S. PATENT DOCUMENTS 5,451,578  9/1995  Claremon et al. .............. 514/212
5,834,404  11/1998  Sagae et al. .............. 504/348

FOREIGN PATENT DOCUMENTS 278 742  8/1988  European Pat. Off. .
298 680  1/1989  European Pat. Off. .

*Primary Examiner*—Ba K. Trinh
*Attorney, Agent, or Firm*—Keil & Weinkauf

[57] ABSTRACT

2-Benzoylcyclohexane-1,3-diones of the formula I:

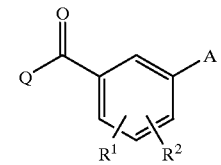

where:

$R^1$ and $R^2$ are each hydrogen, mercapto, nitro, halogen, cyano, thiocyanato, $C_1$–$C_6$-alkyl, $C_1$–$C_6$-haloalkyl, $C_1$–$C_6$-alkoxy, $C_1$–$C_6$-alkyl, $C_2$–$C_6$-alkenyl, $C_2$–$C_6$-alkynyl, —$OR^{10}$, —$OCOR^{10}$, —$OSO_2R^{10}$, —$S(O)_nR^{10}$, —$SO_2OR^{10}$, —$SO_2NR^3R^{10}$, —$NR^{10}SO_2R^{10}$ or —$NR^{10}COR$;

Q is a cyclohexane-1,3-dione ring with or without substitution, which is attached in position 2;

A is a group of the formula IIa, IIb or III:

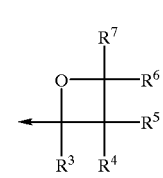

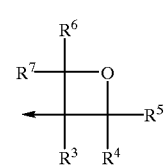

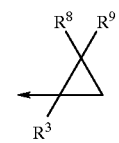

where the substituents are as defined in claim 1, and agriculturally useful salts thereof are described.

11 Claims, No Drawings

SUBSTITUTED 2-BENZOYLCYCLOHEXANE-1,3-DIONES

This application is a 371 of PCT/EP 98/02448 dated Apr. 24, 1998.

The present invention relates to substituted 2-benzoylcyclohexane-1,3-diones of the formula I:

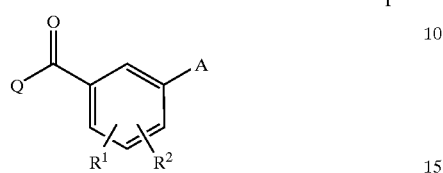

I where:
$R^1$ and $R^2$ are each hydrogen, mercapto, nitro, halogen, cyano, thiocyanato, $C_1$–$C_6$-alkyl, $C_1$–$C_6$-haloalkyl, $C_1$–$C_6$-alkoxy, $C_1$–$C_6$-alkyl, $C_2$–$C_6$-alkenyl, $C_2$–$C_6$-alkynyl, $-OR^{10}$, $-OCOR^{10}$, $-OSO_2R^{10}$, $-S(O)_n R^{10}$, $-SO_2OR^{10}$, $-SO_2NR^3R^{10}$, $-NR^{10}SO_2R^{10}$ or $-NR^{10}COR$;

Q is a cyclohexane-1,3-dione ring with or without substitution which is attached in position 2;

A is a group of the formula IIa, IIb or III:

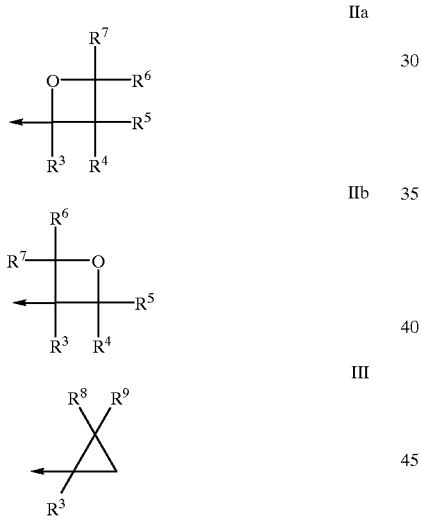

where:
$R^3$ is hydrogen, $C_1$–$C_6$-alkyl or phenyl, where the alkyl and phenyl radicals mentioned may be partially or fully halogenated and/or may carry one to three of the following groups:

hydroxyl, mercapto, amino, cyano, $R^{10}$, $-OR^{10}$, $-SR^{10}$, $-NR^8R^{10}$, $=NOR^{10}$, $-OCOR^{10}$, $-SCOR^{10}$, $-NR^8COR^{10}$, $-CO_2R^{10}$, $-COSR^{10}$, $-CONR^8R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals mentioned may in turn be substituted;

$R^4$–$R^7$ may be identical or different and, independently of each other, are:
hydrogen, hydroxyl, mercapto, amino, halogen, $C_1$–$C_6$-alkyl, $C_3$–$C_6$-cycloalkyl, phenyl, $-OR^{10}$, $-S(O)_n R^{10}$, $-OS(O)_n R^{10}$, $-PO(OR^{10})_2$, $-NR^3R^{10}$, $-Si(R^{10})_3$ or $-OCOR^{10}$, where the alkyl and cycloalkyl radicals mentioned and $R^3$ and $R^{10}$ of the radicals $-OR^{10}$, $-S(O)_n R^{10}$, $-OS(O)_n R^{10}$, $-PO(OR^{10})_2$, $-NR^3R^{10}$, $-Si(R^{10})_3$, $-OCOR^{10}$ may be partially or fully halogenated and/or may carry one to three of the following groups:

hydroxyl, mercapto, amino, cyano, $R^{10}$, $-OR^{10}$, $-SR^{10}$, $-NR^8R^{10}$, $=NOR^{10}$, $-OCOR^{10}$, $-SCOR^{10}$, $-NR^8COR^{10}$, $-CO_2R^{10}$, $-COSR^{10}$, $-CONR^8R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals mentioned may in turn be substituted;

$R^4$ and $R^5$ together may form a $C_2$–$C_5$-alkylene or $C_2$–$C_5$-alkenylene chain which may be interrupted once or twice by a nitrogen or an oxygen atom, or may form a group $=X$, where X is an oxygen atom or a group $CR^3R^{10}$, $NR^{10}$ or $NOR^{10}$;

$R^6$ and $R^7$ together may form a $C_2$–$C_5$-alkylene or $C_2$–$C_5$-alkenylene chain which may be interrupted once or twice by a nitrogen or an oxygen atom, or may form a group $=X$, where X is an oxygen atom or a group $CR^3R^{10}$, $NR^{10}$ or $NOR^{10}$;

n is zero, one or two;

$R^5$ and $R^6$ together may furthermore, if they are attached to adjacent carbon atoms and if $R^4$ and $R^7$ are each hydrogen, form a $C_3$–$C_4$-alkylene or $C_3$–$C_4$-alkenylene chain which may be interrupted by a nitrogen or an oxygen atom;

$R^8$ and $R^9$ may be identical or different and, independently of each other, are:
hydrogen, nitro, halogen, cyano, $C_1$–$C_6$-alkyl, $C_3$–$C_6$-cycloalkyl, $C_5$–$C_6$-heterocyclyl, $-OR^{10}$, $-SR^{10}$, $-COR^{10}$, $-COOR^{10}$, $-CONR^3R^{10}$, phenyl, phenyl-$C_1$–$C_6$-alkyl and five- or six-membered hetaryl, where the alkyl and cycloalkyl radicals mentioned and $R^3$ and $R^{10}$ of the radicals $-OR^{10}$, $-SR^{10}$, $-COR^{10}$, $-COOR^{10}$, $-CONR^3R^{10}$ may be partially or fully halogenated and/or may carry one to three of the following groups:

hydroxyl, mercapto, amino, cyano, $R^{10}$, $-OR^{10}$, $-SR^{10}$, $-NR^8R^{10}$, $=NOR^{10}$, $-OCOR^{10}$, $-SCOR^{10}$, $-NR^8COR^{10}$, $-CO_2OR^{10}$, $-COSR^{10}$, $-CONR^8R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals mentioned may in turn be substituted;

$R^8$ and $R^9$ together may furthermore form a $C_2$–$C_5$-alkylene or $C_2$–$C_5$-alkenylene chain which may be interrupted once or twice by a nitrogen or an oxygen atom;

$R^{10}$ is hydrogen, $C_1$–$C_6$-alkyl, $C_1$–$C_6$-haloalkyl, $C_2$–$C_6$-alkenyl, $C_2$–$C_6$-alkynyl, phenyl or phenyl-$C_1$–$C_6$-alkyl; where the alkyl radicals mentioned may be partially or fully halogenated and/or may carry one to three of the following groups:

hydroxyl, mercapto, amino, cyano, $R^{10}$, $-OR^{10}$, $-SR^{10}$, $-NR^3R^{10}$, $=NOR^{10}$, $-OCOR^{10}$, $-SCOR^{10}$, $-NR^3COR^{10}$, $-CO_2R^{10}$, $-COSR^{10}$, $-CONR^3R^{10}$, $C_1-C_4$-alkyliminooxy, $C_1-C_4$-alkoxyamino, $C_1-C_4$-alkylcarbonyl, $C_1-C_4$-alkoxy-$C_2-C_6$-alkoxycarbonyl, $C_1-C_4$-alkylsulfonyl, heterocyclyl, heterocyclyloxy, phenyl, benzyl, hetaryl, phenoxy, benzyloxy and hetaryloxy, where the last eight radicals mentioned may in turn be substituted;

and agriculturally useful salts thereof.

In addition, the invention relates to processes and intermediates for preparing compounds of the formula I, to compositions comprising them, and to the use of the compounds of the formula I and to compositions comprising them for controlling harmful plants.

2-Benzoylcyclohexane-1,3-diones are disclosed in the literature, for example in EP-A 278 742, EP-A 298 680, EP-A 320 864 and WO 96/14285.

However, the herbicidal properties of the prior art compounds and their crop plant safety are not entirely satisfactory.

It is an object of the present invention to provide novel, in particular herbicidally active, compounds having improved properties.

We have found that this object is achieved by the 2-benzoylcyclohexane-1,3-diones of the formula I and their herbicidal activity.

tetrabutylammonium, trimethylbenzylammonium, furthermore phosphonium ions, sulfonium ions, preferably tri($C_1-C_4$-alkyl)sulfonium, and sulfoxonium ions, preferably tri($C_1-C_4$-alkyl)sulfoxonium.

Anions of useful acid addition salts are primarily chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and also the anions of $C_1-C_4$-alkanoic acids, preferably formate, acetate, propionate and butyrate.

Emphasis is given to the compounds of the formula I according to the invention where the variable Q is a cyclohexane-1,3-dione ring of the formula IV:

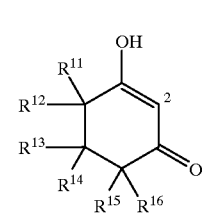

IV which is attached in position 2, where IV also represents the tautomeric formulae IV' and IV":

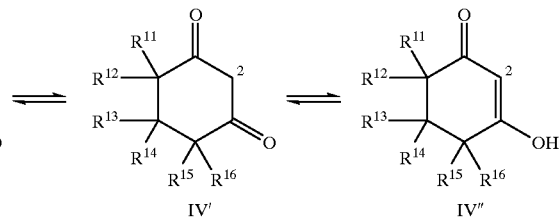

Furthermore, we have found herbicidal compositions which comprise the compounds I and have very good herbicidal activity. Moreover, we have found processes for preparing these compositions and methods for controlling undesirable vegetation using the compounds I.

The present invention also relates to stereoisomers of the compounds of the formula I. Pure stereoisomers and also mixtures thereof are included.

Depending on the substitution pattern, the compounds of the formula I may contain one or more chiral centers and, if this is the case, are present as mixtures of enantiomers or diastereomers. The present invention relates to both the pure enantiomers or diastereomers and also mixtures thereof.

The compounds of the formula I may also be present in the form of their agriculturally useful salts, the kind of salt generally not being important. The salts of those cations or the acid addition salts of those acids whose cations or anions, respectively, do not adversely affect the herbicidal activity of the compounds I are generally suitable.

Suitable cations are in particular ions of the alkali metals, preferably lithium, sodium and potassium, of the alkaline earth metals, preferably calcium and magnesium, and of the transition metals, preferably manganese, copper, zinc and iron, and also ammonium, where, if desired, one to four hydrogen atoms may be replaced by $C_1-C_4$-alkyl or hydroxy-$C_1-C_4$-alkyl and/or one phenyl or benzyl, preferably diisopropylammonium, tetramethylammonium, where:

$R^{11}$, $R^{12}$, $R^{14}$ and $R^{16}$ are each hydrogen or $C_1-C_4$-alkyl;

$R^{13}$ is hydrogen, $C_1-C_4$-alkyl or $C_3-C_4$-cycloalkyl, where the last two groups mentioned may carry one to three of the following substituents:

halogen, $C_1-C_4$-alkylthio or $C_1-C_4$-alkoxy;

or is tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, where the last 6 radicals mentioned may be substituted by one to three $C_1-C_4$-alkyl radicals;

$R^{15}$ is hydrogen, $C_1-C_4$-alkyl or $C_1-C_6$-alkoxycarbonyl;

or $R^{13}$ and $R^{16}$ together form a π bond or a three- to six-membered carbocyclic ring;

or the $CR^{13}R^{14}$ unit may be replaced by C=O.

Process A:

Reactions of cyclohexane-1,3-dione [sic] of the formula IV with an activated carboxylic acid Va or a carboxylic acid Vb, which is preferably activated in situ, to give the acylation product VII, and subsequent rearrangement to the compounds of the formula I according to the invention.

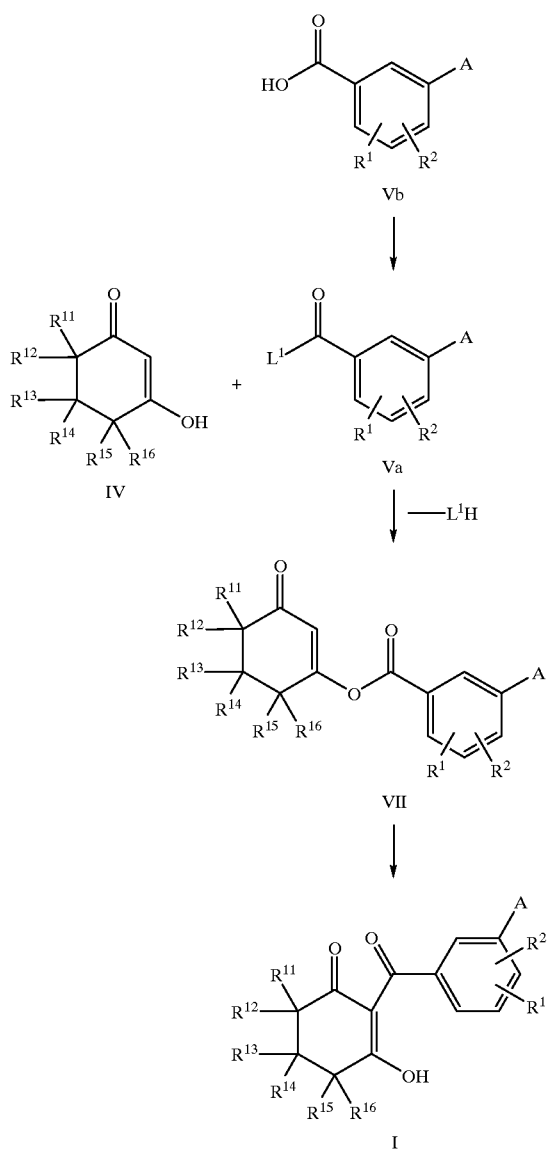

L$^1$ is a nucleophilically exchangeable leaving group such as halogen, for example bromine or chlorine, hetaryl, for example imidazolyl or pyridyl, or carboxylate, for example acetate, trifluoroacetate, ect.

The activated carboxylic acid can be employed directly, as in the case of the acyl halides, or be generated in situ, for example by using dicyclohexylcarbodiimide, triphenylphosphine/azodicarboxylic esters, 2-pyridine disulfite/triphenylphosphine, carbonyldiimidazole, etc.

It may be advantageous to carry out the acylation reaction in the presence of a base. The starting materials and the auxiliary base are advantageously employed in equimolar amounts. A slight excess of the auxiliary base, for example 1.2 to 1.5 molar equivalents, based on II, may be advantageous under certain conditions.

Suitable auxiliary bases are tertiary alkylamines, pyridine or alkali metal carbonates. Examples of solvents which can be used are chlorinated hydrocarbons, such as methylene chloride, 1,2-dichloroethane, aromatic hydrocarbons, such as toluene, xylene, chlorobenzene, ethers, such as diethyl ether, methyl tert-butyl ether, tetrahydrofuran, dioxane, polar aprotic solvents, such as acetonitrile, dimethylformamide, dimethyl sulfoxide, or esters such as ethyl acetate or mixtures of these.

If acyl halides are employed as activated carboxylic acid component, it may be advantageous to cool the reaction mixture to 0–10° C. when adding this reaction partner. The mixture is subsequently stirred at 20–100° C., preferably at 25–50° C., until the reaction is complete. Work-up is carried out in the customary manner, for example by pouring the reaction mixture into water and extracting the product of value. Solvents which are particularly suitable for this purpose are methylene chloride, diethyl ether and ethyl acetate. After the organic phase has been dried and the solvent has been removed, the crude enol ester of the formula VII is purified, preferably by chromatography. Alternatively, it is possible to employ the crude enol ester of the formula VII without further purification for the rearrangement reaction.

The rearrangement of the enol esters of the formula VII to the compounds of the formula I is advantageously carried out at from 20 to 40° C. in a solvent and in the presence of a base and, if appropriate, in the presence of a cyano compound.

Examples of solvents which can be used are acetonitrile, methylene chloride, 1,2-dichloroethane, dioxane, ethyl acetate, toluene or mixtures of these. Preferred solvents are acetonitrile and dioxane.

Suitable bases are tertiary amines such as triethylamine, pyridine or alkali metal carbonates, such as sodium carbonate, potassium carbonate, which are preferably employed in equimolar amounts or up to a four-fold excess, based on the ester. Preference is given to using triethylamine or alkali metal carbonates.

Suitable cyano compounds are inorganic cyanides such as sodium cyanide, potassium cyanide and organic cyano compounds such as acetone cyanohydrin, trimethylsilyl cyanide. They are usually employed in an amount of 1 to 50 mol percent, based on the ester. Preference is given to using acetone cyanohydrin or trimethylsilyl cyanide, for example in an amount of from 5 to 15, preferably 10, mol percent, based on the ester.

Particular preference is given to employing alkali metal carbonates, such as potassium carbonate, in acetonitrile or dioxane.

Work-up can be carried out in a manner known per se. For example, the reaction mixture is acidified with dilute mineral acid, such as 5% strength hydrochloric acid or sulfuric acid, and extracted with an organic solvent, for example methylene chloride, ethyl acetate. The organic extract can be extracted with 5–10% strength alkali metal carbonate solution, for example sodium carbonate or potassium carbonate solution. The aqueous phase is acidified, and the precipitate which forms is filtered off with suction and/or extracted with methylene chloride or ethyl acetate, dried and concentrated.

(Examples of the synthesis of esters of hydroxypyrazoles and the rearrangement reaction of the esters are mentioned for example in EP-A 282 944 or U.S. Pat. No. 4,643,757).

The benzoic acids of the formula V are novel:

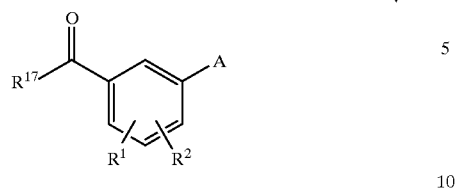

V where:
$R^1$ and $R^2$ are each hydrogen, mercapto, nitro, halogen, cyano, thiocyanato, $C_1$–$C_6$-alkyl, $C_1$–$C_6$-haloalkyl, $C_1$–$C_6$-alkoxy, $C_1$–$C_6$-alkyl, $C_2$–$C_6$-alkenyl, $C_2$–$C_6$-alkynyl, —$OR^{10}$, —$OCOR^{10}$, —$OSO_2R^{10}$, —$S(O)_nR^{10}$, —$SO_2OR^{10}$, —$SO_2NR^3R^{10}$, —$NR^{10}SO_2R^{10}$ or —$NR^{10}COR$;

A is a group of the formula IIIa [sic], IIIb [sic] or IV [sic]:

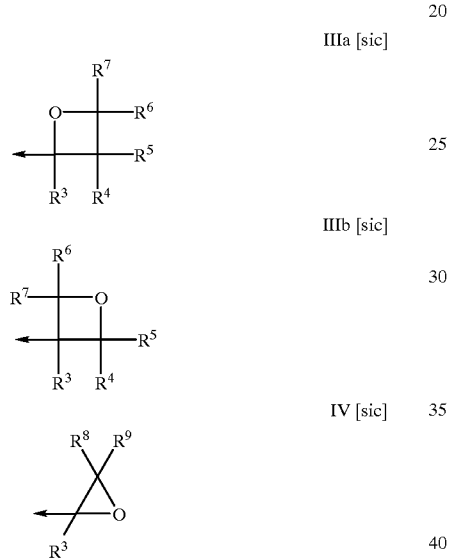

IIIa [sic]

IIIb [sic]

IV [sic]

where:
$R^3$ is hydrogen, $C_1$–$C_6$-alkyl or phenyl,
where the alkyl and phenyl radicals mentioned may be partially or fully halogenated and/or may carry one to three of the following groups:
hydroxyl, mercapto, amino, cyano, $R^{10}$, —$OR^{10}$, —$SR^{10}$, —$NR^3R^{10}$, =$NOR^{10}$, —$OCOR^{10}$, —$SCOR^{10}$, —$NR^3COR^{10}$, —$CO_2R^{10}$, —$COSR^{10}$, —$CONR^3R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals mentioned may in turn be substituted;

$R^4$–$R^7$ may be identical or different and, independently of each other, are:
hydrogen, hydroxyl, mercapto, amino, halogen, $C_1$–$C_6$-alkyl, $C_3$–$C_6$-cycloalkyl, $C_4$–$C_6$-cycloalkenyl, phenyl, —$OR^{10}$, —$S(O)_nR^{10}$, —$OS(O)_nR^{10}$, —$PO(OR^{10})_2$, —$NR^3R^{10}$, —$Si(R^3)_3$ or —$OCOR^{10}$,
where the alkyl and cycloalkyl radicals mentioned and $R^3$ and $R^{10}$ of the radicals —$OR^{10}$, —$S(O)_nR^{10}$, —$OS(O)_nR^{10}$, —$PO(OR^{10})_2$, —$NR^3R^{10}$,
—$Si(R^{10})_3$, —$OCOR^{10}$ may be partially or fully halogenated and/or may carry one to three of the following groups:
hydroxyl, mercapto, amino, cyano, $R^{10}$, —$OR^{10}$, —$SR^{10}$, —$NR^3R^{10}$, =$NOR^{10}$, —$OCOR^{10}$, —$SCOR^{10}$, —$NR^3COR^{10}$, —$CO_2R^{10}$, —$COSR^{10}$, —$CONR^3R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals mentioned may in turn be substituted;

$R^4$ and $R^5$ together may form a $C_2$–$C_5$-alkylene or $C_2$–$C_5$-alkenylene chain which may be interrupted once or twice by a nitrogen or an oxygen atom, or may form a group =X, where X is an oxygen atom or a group $CR^3R^{10}$, $NR^{10}$, $NNR^3R^{10}$ or $NOR^{10}$;

$R^6$ and $R^7$ together may form a $C_2$–$C_5$-alkylene or $C_2$–$C_5$-alkenylene chain which may be interrupted once or twice by a nitrogen or an oxygen atom, or may form a group =X, where X is an oxygen atom or a group $CR^3R^{10}$, $NR^{10}$ or $NOR^{10}$, $NNR^3R^{10}$;

n is zero, one or two;

$R^5$ and $R^6$ together may furthermore, if they are attached to adjacent carbon atoms and if $R^4$ and $R^7$ are each hydrogen, form a $C_3$–$C_4$-alkylene or $C_3$–$C_4$-alkenylene chain which may be interrupted by a nitrogen or an oxygen atom;

$R^8$ and $R^9$ may be identical or different and, independently of each other, are:
hydrogen, nitro, halogen, cyano, $C_1$–$C_6$-alkyl, $C_3$–$C_6$-cycloalkyl, $C_4$–$C_6$-cycloalkenyl, $C_5$–$C_6$-heterocyclyl, —$OR^{10}$, —$SR^{10}$, —$COR^{10}$, —$COOR^{10}$, —$CONR^3R^{10}$, phenyl, phenyl-$C_1$–$C_6$-alkyl and five- or six-membered hetaryl,
where the alkyl and cycloalkyl radicals mentioned and $R^3$ and $R^{10}$ of the radicals —$OR^{10}$, —$SR^{10}$, —$COR^{10}$, —$COOR^{10}$, —$CONR^3R^{10}$ may be partially or fully halogenated and/or may carry one to three of the following groups:
hydroxyl, mercapto, amino, cyano, $R^{10}$, —$OR^{10}$, —$SR^{10}$, —$NR^3R^{10}$, =$NOR^{10}$, —$OCOR^{10}$, —$SCOR^{10}$, —$NR^3COR^{10}$, —$CO_2R^{10}$, —$COSR^{10}$, —$CONR^3R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals mentioned may in turn be substituted;

$R^8$ and $R^9$ together may furthermore form a $C_2$–$C_5$-alkylene or $C_2$–$C_5$-alkenylene chain which may be interrupted once or twice by a nitrogen or an oxygen atom;

$R^{10}$ is hydrogen, $C_1$–$C_6$-alkyl, $C_1$–$C_6$-haloalkyl, $C_2$–$C_6$-alkenyl, $C_2$–$C_6$-alkynyl, phenyl or phenyl-$C_1$–$C_6$-alkyl;
where the alkyl radicals mentioned may be partially or fully halogenated and/or may carry one to three of the following groups:
hydroxyl, mercapto, amino, cyano, $R^{10}$, —$OR^{10}$, —$SR^{10}$, —$NR^3R^{10}$, =$NOR^{10}$, —$OCOR^{10}$, —$SCOR^{10}$, —$NR^3COR^{10}$, —$CO_2R^{10}$, —$COSR^{10}$, —$CONR^3R^{10}$, $C_1$–$C_4$- alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, the last eight radicals mentioned may in turn be substituted;

$R^{17}$ is hydroxyl or a radical which can be removed by hydrolysis.

Examples of radicals which can be removed by hydrolysis are alkoxy, phenoxy, alkylthio and phenylthio radicals which can be substituted, halides, hetaryl radicals which are bonded via nitrogen, amino and imino radicals which can be substituted, etc.

Preference is given to benzoyl halides Va where L=halogen ($\hat{=}$V where $R^{17}$=halogen),

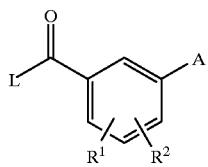

Va where the variables $R^1$, $R^2$, and A are each as defined under formula V and L is halogen, in particular chlorine or bromine.

Preference is also given to benzoic acids of the formula Vb ($\hat{=}$V where $R^{17}$=hydroxyl),

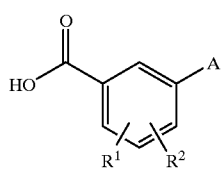

Vb where where [sic] the variables $R^1$, $R^2$, and A are each as defined under formula V.

Preference is also given to benzoic esters of the formula Vc ($\hat{=}$V where $R^{17}$=$C_1$–$C_6$-alkoxy),

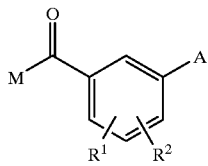

Vc where the variables $R^1$, $R^2$, and A are each as defined under formula V and M is $C_1$–$C_6$-alkoxy.

The compounds of the formula Va (where L=halogen) can be synthesized by methods similar to those known from the literature (cf. L. G. Fieser, M. Fieser "Reagents for Organic Synthesis", Vol. I, (1967) pp. 767–769) by reacting benzoic acids of the formula Vb with halogenating agents such as thionyl chloride, thionyl bromide, phosgene, diphosgene, triphosgene, oxalyl chloride and oxalyl bromide.

The benzoic acids of the formula Vb can be obtained, inter alia, by hydrolyzing the benzoic esters of the formula Vc (where M=$C_1$–$C_6$-alkoxy).

The benzoic esters of the formula Vc according to the invention can be synthesized by various methods known from the literature (for example a: G. Dittus in Houben-weyl, Methoden der Organischen Chemie, Volume VI/3, Oxygen Compounds I, 4th Edition, 1965, p. 493 ff., Georg Thieme Verlag; b: T. L. Gilchrist, Heterocyclenchemie, 2nd Edition, Verlag Chemie, 1995), as illustrated in the examples that follow.

Process A

Cyclization of 1,3-halohydrins of the formula VIIIa or VIIIb under alkaline reaction conditions to give the benzoic esters of the formula Vc according to the invention where the variables $R^1$, $R^2$ and M are each as defined under formula V, A is a group of the formula IIa or IIb and $L^2$ is a nucleophilically exchangeable leaving group, preferably iodine, bromine or chlorine.

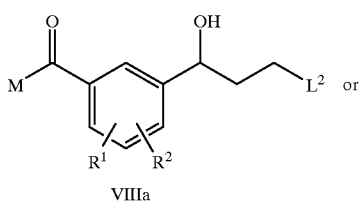

Suitable for use as eliminating agents are especially alkali metal and alkaline earth metal hydroxides, for example potassium hydroxide or sodium hydroxide, or organic bases, for example alkoxides such as sodium methoxide, or secondary amines such as diethylamine.

The elimination of hydrogen halide can be effected even by alkaline salts, for example by potassium fluoride (E. Gryszkiewics-Trochimowski, O. Gryszkiewics-Trochimowski, Bulletin de la Société Chimique de France, Mémoires 123 (1953)).

The cleaving agents may be employed in solution or neat, preferably in solution, for example methanolic sodium methoxide solution.

The cyclization is carried out in inert solvents, for example in alcohols such as methanol or ethanol.

Process B

Photochemical cycloadditions of aldehydes of the formula IX or ketones of the formula X with olefins XI, preferably with enol ethers of the formula XI (where $R^7$=$OR^{10}$), to give the benzoic esters of the formula Vc according to the invention where the variables $R^1$, $R^2$, $R^3$, $R^{10}$ and M are each as defined under formula V and A is a group of the formula IIa.

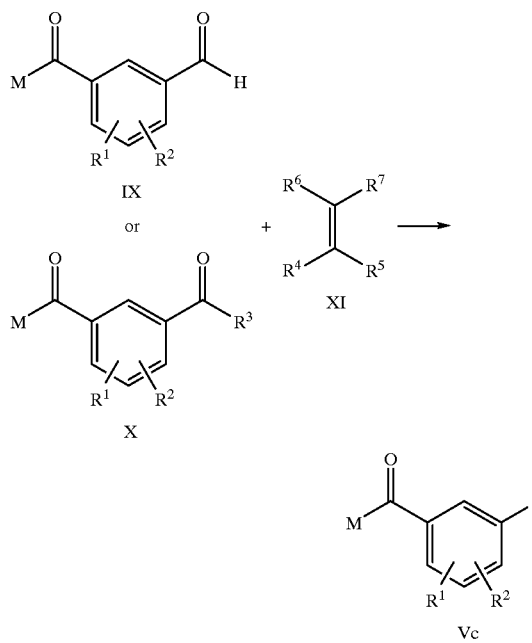

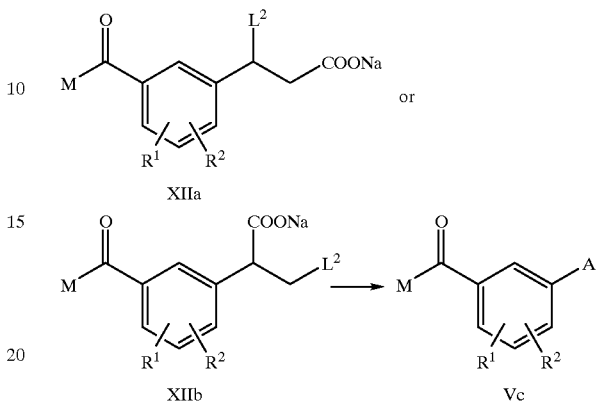

The photochemical cycloaddition is carried out in inert solvents which do not have any significant UV absorption in the spectral range used. Thus, for example, acetonitrile or aliphatic or aromatic hydrocarbons such as n-hexane or toluene can be used.

Suitable radiation sources are appropriate UV radiators, preferably low-pressure, medium-pressure or high-pressure mercury lamps (A. M. Braun, M. T. Maurette, E. Oliveros, Photochemical Technology, John Wiley & Sons Ltd 1991). Low-pressure mercury lamps emit at 189 and 253 nm, the emission at 189 nm being almost completely absorbed by oxygen, water or solvent, so that low-pressure mercury lamps virtually emit a monochromatic radiation at 253 nm.

Medium- and high-pressure mercury lamps are operated at pressures from 1 to 100 atm and emit, depending on pressure and temperature, in a wavelength range of from 200 to 600 nm, medium-pressure mercury lamps having a dominant emission line at 366 nm and high-pressure mercury lamps having two dominant emissions at 436 and 546 nm.

Furthermore, it is possible to employ medium- and high-pressure mercury lamps which are doped with metal salts such as thallium halides, indium halides, sodium halides or gallium halides. The doping causes a modification of the emission spectrum of the medium- and high-pressure mercury lamps and results in the emission of additional emission lines characteristic for the doping in question.

In addition, it is possible to use appropriate filters which suppress undesirable wavelength ranges.

Suitable photoreactors should not absorb in the UV range used, but should be transparent for the wavelengths which are emitted by an appropriate UV radiator.

Particularly suitable for this purpose is borosilicate glass, for example borosilicate BK7 (Schott) or Corning 7740 (Pyrex) or quartz glass, which is even more transparent than borosilicate glass in the UV range.

Preferred photoreactors are falling-film reactors.

Process C

Intramolecular cyclization of β-halofatty acids or their alkali metal salts of the formula XIIa or XIIb to give the benzoic esters of the formula Vc according to the invention where the variables $R^1$, $R^2$ and M are each as defined under formula V, A is a group of the formula IIa or IIb and $L^2$ is a nucleophilically displaceable leaving group, preferably iodine, bromine or chlorine.

The elimination of hydrogen halide from β-halofatty acids or salts thereof, such as the sodium salts, by aqueous solutions of alkali metal salts, for example sodium carbonate solution, leads to the formation of β-lactones (A. Einhorn, Chem. Ber. 16 (1883), 2208). Instead of sodium carbonate, silver oxide or silver salts are frequently successfully used for the elimination of hydrogen halide.

Owing to the lability of the β-lactones in the presence of aqueous alkali metal halides, it is necessary to prepare water-soluble β-lactones in the presence of solvents to remove the β-lactone formed as quickly as possible from the aqueous phase (Org. Reactions 8 (1954), 309). Suitable solvents include, for example, diethyl ether and chloroform.

Process D

Cycloaddition of aldehydes of the formula IX or ketones of the formula X with ketenes XIII to give the benzoic esters of the formula Vc according to the invention where the variables $R^1$, $R^2$, $R^3$, $R^4$, $R^5$ and M are each as defined under formula V and A is a group of the formula IIa or IIb.

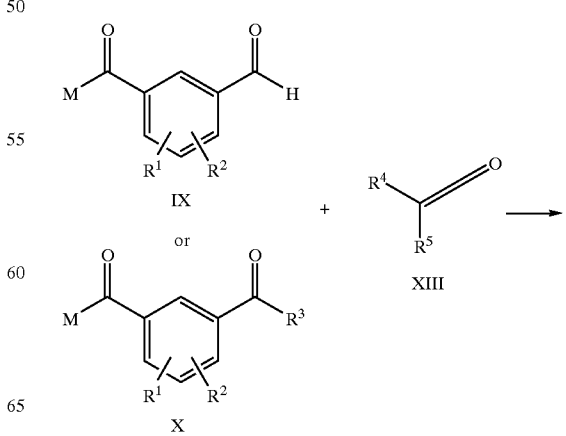

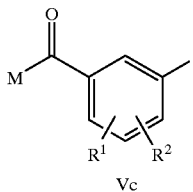

Vc

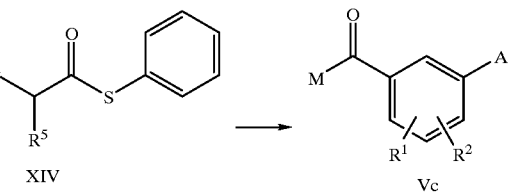

XIV → Vc

Depending on the kind of catalyst and the reaction conditions, ketenes react with carbonyl compounds at 20–100° C., preferably at 40–80° C., to form enol acetates or β-lactones (for example H. Kröper in Houben-Weyl, Methoden der Organischen Chemie, Volume VI/2, Oxygen Compounds I, Part 2, 4th Edition, 1965, p. 511 ff., Georg Thieme Verlag). The formation of β-lactones occurs after C-acetylation if basic catalysts such as tertiary amines or alkali metals or alkaline earth metals are employed (J. A. Spence, E. F. Degering, Chem. Abst. 43 (1949), 6654). In the presence of specific catalysts, aldehydes or ketones even condense at lower temperatures of from 0 to 10° C. with the most simple ketenes to form β-lactones. The choice of catalyst depends on the individual carbonyl compounds. Catalysts which are suitable for aromatic aldehydes are, for example, boric acid, triacetyl borate, zinc thiocyanate and zinc chloride, aluminum chloride, mercury(II) chloride, and activated alumina and silica.

The reaction must be carried out in an anhydrous medium in order to achieve high yields.

Suitable for use as solvents are ethers, for example diethyl ether, haloalkanes, for example methylene chloride or chloroform, and, owing to the tendency of the β-lactones to polymerize, preferably ketones.

Process E

Addition of thiol ester enolates XIV to aldehydes of the formula IX or ketones of the formula X by a method similar to processes known from the literature (R. L. Danheiser, J. S. Nowick, Journal of Organic Chemistry 56 (1991), 1176) to give the benzoic esters of the formula Vc according to the invention where the variables $R^1$, $R^2$, $R^3$, $R^4$, $R^5$ and M are each as defined under formula V and A is a group of the formula IIIa [sic] or IIIb [sic].

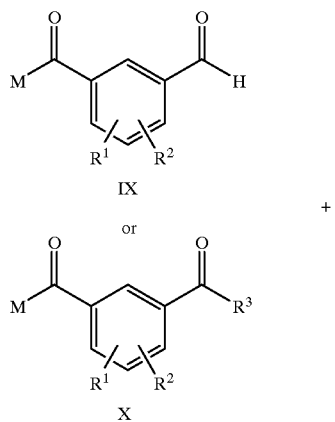

The thiol ester enolates XIV used as starting materials can be prepared in a simple one-step reaction from carboxylic acid derivatives (for example T. Mukaiyama, T. Takeda, K. Atsumi, Chemistry Letters 1974, 187).

The corresponding enolate, which forms the desired compounds of the formula Vc, in particular β-lactones, with aldehydes or ketones, is formed in the presence of an equivalent of a base, preferably a lithium base such as, for example, lithium diisopropylamide.

Process F

Cyclization of 1,2-halohydrins of the formula XVa or XVb under alkaline reaction conditions to give the benzoic esters of the formula Vc according to the invention where the variables $R^1$, $R^2$ and M are each as defined under formula V, A is a group of the formula III and $L^2$ is a nucleophilically displaceable leaving group, preferably iodine, bromine or chlorine.

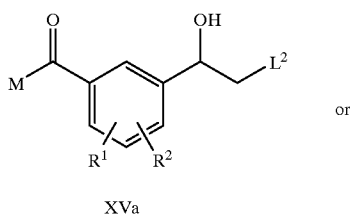

XVa or

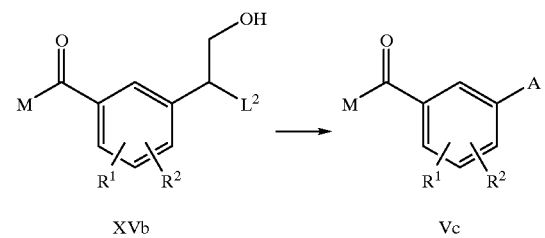

XVb → Vc

Instead of the 1,2-halohydrins, it is also possible to use their acetates as starting materials in a similar manner.

Related to the methods described is the preparation of benzoic esters of the formula Vc according to the invention by elimination of p-toluenesulfonic acid from 2-hydroxytoluenesulfonates (for example H. Ohle, L. v. Vargha, Chemische Berichte 62, (1929), 2440).

Particularly suitable eliminating agents are alkali metal hydroxides and alkaline earth metal hydroxides; organic bases, for example alkoxides, secondary amines or pyridine and its homologs such as collidine, are less frequently used. Preferred alkali metal hydroxides and alkaline earth metal hydroxides are for example potassium hydroxide, sodium hydroxide or calcium hydroxide.

In some instances, the elimination of hydrogen halide can be effected even by alkaline salts, for example potassium carbonate, barium carbonate or potassium fluoride. Furthermore, the use of aluminates, silicates and zincates (for example J. D. Zech, Chemical Abstracts, 46 (1952), 8672), lead(II) oxide, aluminum oxide, silver nitrate or alkaline ion exchangers has been described.

The cleaving agents can be employed in solution or neat, in some instances in powdered form, for example powdered potassium hydroxide.

Cyclization is carried out in inert solvents. Suitable for this purpose are open-chain or cyclic ethers, for example diethyl ether or dioxane, or aromatic hydrocarbons, for example benzene or toluene.

Process G

Epoxidation of olefins of the formula XVI to give the benzoic esters of the formula Vc according to the invention where the variables $R^1$, $R^2$ and M are each as defined under formula V and A is a group of the formula IIV [sic].

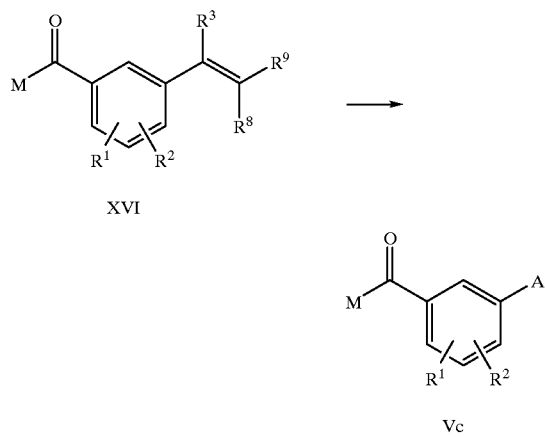

XVI

Vc

Similarly to processes known from the literature, the epoxidation is frequently carried out using peracids, for example perbenzoic acid, monoperphthalic acid, performic acid, peracetic acid, trifluoroperacetic acid or perpropionic acid (for example R. Criegee, Houben-Weyl, "Methoden der Organischen Chemie", Volume VIII, Oxygen Compounds III, 4th Edition, 1965, p. 40 ff., Georg Thieme Verlag), hydrogen peroxide or tert-butyl hydroperoxide in alkaline solution, preferably in aqueous sodium hydroxide solution, or using dioxiranes, for example dimethyldioxirane or derivatives thereof such as, for example, (trifluoromethyl) methyldioxirane (W. Adam, A. K. Smerz, Bulletin des Sociétés Chimiques Belges 105 (1996), 581).

The peracid epoxidation is carried out in inert solvents such as diethyl ether, chloroform, carbon tetrachloride, ethyl chloride or occasionally in glacial acetic acid, whereas dioxiranes are preferably employed in acetone or derivatives thereof such as, for example, trifluoromethyl methyl ketone.

Peracid, hydrogen peroxide, tert-butyl hydroperoxide or dioxirane is often employed for the reaction in a slight excess; however, an excess of olefin may be advantageous if the oxidizing agent is to be utilized fully.

Process H

Condensation of aldehydes of the formula IX with α-halofatty acid esters XVII or related α-halofatty acid derivatives, for example α-halofatty amides, nitriles or ketones in the presence of alkaline condensing agents by processes known from the literature (for example M. Ballester, Chemical Reviews 55 (1955), 283) to give the benzoic esters of the formula Vc according to the invention where the variables $R^1$, $R^2$, $R^{10}$ and M are each as defined under formula V and A is a group of the formula III.

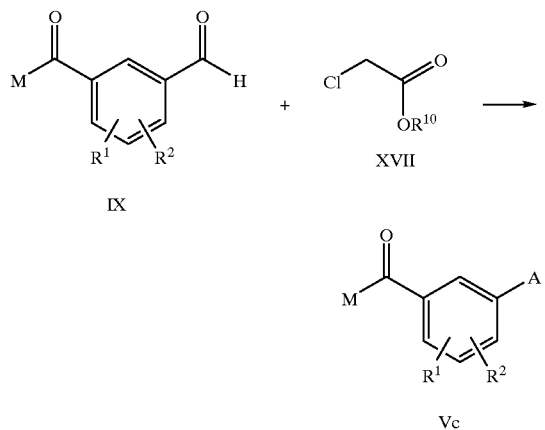

IX    XVII

Vc

Suitable condensing agents are inorganic or organic catalysts, for example sodium hydride in mineral oil, lithium hydride, tetraethylammonium ethoxide, sodium ethoxide, potassium tert-butoxide or diisopropylmagnesium bromide.

The reaction is carried out in inert solvents, for example in xylene, diethyl ether, methanol, ethanol or tert-butanol.

Emphasis is given to compounds of the formula I according to the invention where A is a group of the formula IIa or IIb and $R^4$–$R^7$ are each hydrogen, hydroxyl, mercapto, amino, halogen, $C_1$–$C_6$-alkyl, $C_3$–$C_6$-cycloalkyl, phenyl, —$OR^{10}$, —$S(O)_nR^{10}$, —$OS(O)_nR^{10}$, —$PO(OR^{10})_2$, —$NR^3R^{10}$, —$Si(R^{10})_3$ or —$OCOR^{10}$, where the alkyl and cycloalkyl radicals mentioned and $R^3$ and $R^{10}$ of the radicals —$OR^{10}$, —$S(O)_nR^{10}$, —$OS(O)_nR^{10}$, —$PO(OR^{10})_2$, —$NR^3R^{10}$, —$Si(R^{10})_3$, —$OCOR^{10}$ may be partially or fully halogenated and/or may carry one to three of the following groups:

hydroxyl, mercapto, amino, cyano, $R^{10}$, —$OR^{10}$, —$SR^{10}$, —$NR^3R^{10}$, =$NOR^{10}$, —$OCOR^{10}$, —$SCOR^{10}$, —$NR^3COR^{10}$, —$CO_2R^{10}$, —$COSR^{10}$, —$CONR^3R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals mentioned may in turn be substituted.

Additionally, emphasis is to be given to compounds of the formula I according to the invention where A is a group of the formula IIIa [sic] or IIIb [sic] and $R^4$ and $R^5$ together form a $C_2$–$C_5$-alkylene or $C_2$–$C_5$-alkenylene chain which may be interrupted once or twice by a nitrogen or an oxygen atom, or form a group =X, where X is an oxygen atom or a group $CR^3R^{10}$, $NR^{10}$ or $NOR^{10}$;

and/or $R^6$ and $R^7$ together form a $C_2$–$C_5$-alkylene or $C_2$–$C_5$-alkenylene chain which may be interrupted once or twice by a nitrogen or an oxygen atom, or form a group =X, where X is an oxygen atom or a group $CR^3R^{10}$, $NR^{10}$ or $NOR^{10}$.

Furthermore, emphasis is to be given to compounds of the formula I according to the invention where A is a group of the formula IIIa [sic] or IIIb [sic] and $R^5$ and $R^6$ together, if they are attached to adjacent carbon atoms and if $R^4$ and $R^7$ are each hydrogen, form a $C_3$–$C_4$-alkylene or $C_3$–$C_4$-alkenylene chain which may be interrupted by a nitrogen or an oxygen atom.

Moreover, emphasis is to be given to compounds of the formula I according to the invention where A is a group of the formula IVb and $R^8$ and $R^9$ are each hydrogen, nitro, halogen, cyano, $C_1$–$C_6$-alkyl, $C_3$–$C_6$-cycloalkyl, $C_5$–$C_6$-heterocyclyl, —$OR^{10}$, —$SR^{10}$, —$COR^{10}$, —$COOR^{10}$, —$CONR^3R^{10}$, phenyl, phenyl-$C_1$–$C_6$-alkyl and five- or six-membered hetaryl, where the alkyl and cycloalkyl radicals mentioned and $R^3$ and $R^{10}$ of the radicals —$OR^{10}$, —$SR^{10}$, —$COR^{10}$, —$COOR^{10}$, —$CONR^3R^{10}$ may be partially or fully halogenated and/or may carry one to three of the following groups:

hydroxyl, mercapto, amino, cyano, $R^{10}$, —$OR^{10}$, —$SR^{10}$, —$NR^3R^{10}$, =$NOR^{10}$, —$OCOR^{10}$, —$SCOR^{10}$, —$NR^3COR^{10}$, —$CO_2R^{10}$, —$COSR^{10}$, —$CONR^3R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals mentioned may in turn be substituted.

Additionally, emphasis is to be given to compounds of the formula I according to the invention where A is a group of the formula IVb and $R^8$ and $R^9$ together form a $C_2$–$C_5$-alkylene or $C_2$–$C_5$-alkenylene chain which may be interrupted once or twice by a nitrogen or an oxygen atom.

The organic moieties mentioned for the substituents $R^1$–$R^{16}$ or as radicals on phenyl, hetaryl and heterocyclyl rings are collective terms for individual enumerations of the individual group members. All hydrocarbon chains, ie. all alkyl, haloalkyl, cycloalkyl, alkoxyalkyl, alkoxy, haloalkoxy, alkyliminooxy, alkoxyamino, alkylsulfonyl, haloalkylsulfonyl, alkylcarbonyl, haloalkylcarbonyl, alkoxycarbonyl, alkoxyalkoxycarbonyl, alkenyl, cycloalkenyl, alkynyl moieties can be straight-chain or branched. Unless otherwise specified, halogenated substituents preferably have attached to them one to five identical or different halogen atoms, the meaning of halogen being in each case fluorine, chlorine, bromine or iodine.

Examples of other meanings are:

$C_1$–$C_4$-alkyl, and the alkyl moieties of $C_1$–$C_4$-alkylcarbonyl: methyl, ethyl, n-propyl, 1-methylethyl, butyl, 1-methylpropyl, 2-methylpropyl and 1,1-dimethylethyl;

$C_1$–$C_6$-alkyl, and the alkyl moieties of $C_1$–$C_6$-alkoxy-$C_1$–$C_6$-alkyl and $C_1$–$C_6$-alkylcarbonyl: $C_1$–$C_4$-alkyl as mentioned above, and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$–$C_4$-haloalkyl: a $C_1$–$C_4$-alkyl radical as mentioned above which is partially or fully substituted by fluorine, chlorine, bromine and/or iodine, ie. for example chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_6$-haloalkyl, and the haloalkyl moieties of $C_1$–$C_6$-haloalkylcarbonyl: $C_1$–$C_4$-haloalkyl as mentioned above, and also 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_1$–$C_4$-alkoxy, and the alkoxy moieties of $C_1$–$C_4$-alkoxyamino, $C_1$–$C_4$-alkoxy-$C_2$–$C_6$-alkoxycarbonyl and $C_1$–$C_4$-alkoxycarbonyl: methoxy, ethoxy, propoxy, 1-methylethoxy, butoxy, 1-methylpropoxy, 2-methylpropoxy and 1,1-dimethylethoxy;

$C_1$–$C_6$-alkoxy, and the alkoxy moieties of $C_1$–$C_6$-alkoxy-$C_1$–$C_6$-alkyl, $C_1$–$C_6$-alkoxy-$C_2$–$C_6$-alkyl, $C_1$–$C_4$-alkoxy-$C_2$–$C_6$-alkoxycarbonyl and $C_1$–$C_6$-alkoxycarbonyl: $C_1$–$C_4$-alkoxy as mentioned above, and also pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, ie. for example fluoromethoxy, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$–$C_4$-alkylsulfonyl ($C_1$–$C_4$-alkyl-S(=O)$_2$—): methylsulfonyl, ethylsulfonyl, propylsulfonyl, 1-methylethylsulfonyl, butylsulfonyl, 1-methylpropylsulfonyl, 2-methylpropylsulfonyl and 1,1-dimethylethylsulfonyl;

$C_1$–$C_6$-alkylsulfonyl: $C_1$–$C_4$-alkylsulfonyl as mentioned above, and also pentylsulfonyl, 1-methylbutylsulfonyl, 2-methylbutylsulfonyl, 3-methylbutylsulfonyl, 2,2-dimethylpropylsulfonyl, 1-ethylpropylsulfonyl, 1,1-dimethylpropylsulfonyl, 1,2-dimethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_1$–$C_6$-haloalkylsulfonyl: a $C_1$–$C_6$-alkylsulfonyl radical as mentioned above which is partially or fully substituted by fluorine, chlorine, bromine and/or iodine, ie. fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2,2,2-trichloroethylsulfonyl, 2-chloro-2-fluoroethylsulfonyl, 2-chloro-2,2-difluoroethylsulfonyl, 2,2-dichloro-2-fluoroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(choromethyl)-2-chloroethylsulfonyl [sic], 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl and dodecafluorohexylsulfonyl;

$C_1$–$C_4$-alkyliminooxy: methyliminooxy, ethyliminooxy, 1-propyliminooxy, 2-propyliminooxy, 1-butyliminooxy and 2-butyliminooxy;

$C_3$–$C_6$-alkenyl: prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl, 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl;

$C_2$–$C_6$-alkenyl: $C_3$–$C_6$-alkenyl as mentioned above, and also ethenyl;

$C_3$–$C_6$-alkynyl: prop-1-yn-1-yl, prop-2-yn-1-yl, but-1-yn-1-yl, but-1-yn-3-yl, but-1-yn-4-yl, but-2-yn-1-yl, pent-1-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-1-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl;

$C_2$–$C_6$-alkynyl: $C_3$–$C_6$-alkynyl as mentioned above, and also ethynyl:

$C_3$–$C_6$-cycloalkyl: cyclopropyl, cyclobutyl, cyclopentyl and cyclohexyl;

$C_4$–$C_6$-cycloalkenyl: cyclobuten-1-yl, cyclobuten-3-yl, cyclopenten-1-yl, cyclopenten-3-yl, cyclopenten-4-yl, cyclohexen-1-yl, cyclohexen-3-yl and cyclohexen-4-yl;

heterocyclyl, and also the heterocyclyl radicals in heterocyclyloxy: three- to seven-membered saturated or partially unsaturated mono- or polycyclic heterocycles which contain one to three hetero atoms selected from a group consisting of oxygen, nitrogen and sulfur, such as oxiranyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofuran-2-yl, 2,3-dihydrofuran-3-yl, 2,3-dihydrofuran-4-yl, 2,3-dihydrofuran-5-yl, 2,5-dihydrofuran-2-yl, 2,5-dihydrofuran-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroxazol-5-yl, 2,3-dihydroisothiazol-3-yl, 2,3-dihydroisothiazol-4-yl, 2,3- dihydroisothiazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydropyrazol-3-yl, 2,3-dihydropyrazol-4-yl, 2,3-dihydropyrazol-5-yl, 4,5-dihydropyrazol-3-yl, 4,5-dihydropyrazol-4-yl, 4,5-dihydropyrazol-5-yl, 2,5-dihydropyrazol-3-yl, 2,5-dihydropyrazol-4-yl, 2,5-dihydropyrazol-5-yl, 2,3-dihydrooxazol-2-yl, 2,3-dihydrooxazol-4-yl, 2,3-dihydrooxazol-5-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 3-tetrahydropyranyl, 4-tetrahydropyranyl, 2-tetrahydrothiopyranyl, 3-tetrahydrothiopyranyl, 4-tetrahydrothiopyranyl, 1,3-dioxolan-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, hetaryl, and also the hetaryl radicals in hetaryloxy: aromatic mono- or polycyclic radicals which, besides carbon ring members, may additionally contain one to four nitrogen atoms or one to three nitrogen atoms and one oxygen or one sulfur atom or one oxygen or one sulfur atom, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4,5-tetrazin-3-yl, and also the corresponding benzo-fuzed derivatives.

All phenyl, hetaryl and heterocyclyl rings are preferably unsubstituted or have attached to them one to three halogen atoms and/or one or two radicals selected from the following group: nitro, cyano, methyl, trifluoromethyl, methoxy, trifluoromethoxy or methoxycarbonyl.

With a view to the use of the compounds of the formula I according to the invention as herbicides, the variables preferably have the following meanings, viz. in each case alone or in combination:

$R^1$ is nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^5$ or —$S(O)_nR^7$;
  especially preferably nitro, halogen, such as fluorine, chlorine or bromine, $C_1$–$C_6$-haloalkyl, —$OR^5$ or —$SO_2R^7$;

$R^2$ is hydrogen, nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^5$ or —$S(O)_nR^7$;
  especially preferably hydrogen, nitro, halogen, such as fluorine, chlorine or bromine, $C_1$–$C_6$-alkyl, $C_1$–$C_6$-haloalkyl, —$OR^5$ or —$SO_2R^7$;

$R^4$–$R^7$ are each hydrogen, hydroxyl, mercapto, amino, halogen, $C_1$–$C_4$-alkyl, $C_5$–$C_6$-cycloalkyl, $C_5$–$C_6$-cycloalkenyl, phenyl, —$OR^{10}$, —$S(O)_nR^{10}$, —$OS(O)_nR^{10}$, —$PO(OR^{10})_2$, —$NR^3R^{10}$, —$Si(R^{10})_3$ or —$OCOR^{10}$,
  where the alkyl and cycloalkyl radicals mentioned and $R^3$ and $R^{10}$ of the radicals —$OR^{10}$, —$S(O)_nR^{10}$, —$OS(O)_nR^{10}$, —$PO(OR^{10})_2$, —$NR^3R^{10}$, —$Si(R^{10})_3$, —$OCOR^{10}$ may be partially or fully halogenated and/or may carry one to three of the following groups:
    nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl;
    especially preferably hydrogen, hydroxyl, mercapto, halogen, for example fluorine, chlorine or bromine, $C_1$–$C_4$-alkyl, —$OSO_2R^{10}$, —$OPO_3R^{10}$, —$Si(CH_3)_3$;

$R^4$ and $R^5$ together preferably form a $C_2$–$C_5$-alkylene or $C_2$–$C_5$-alkenylene chain which may be interrupted once or twice by an oxygen atom, or form a group =X, where X is preferably an oxygen atom or $NR^{10}$;
  especially preferably $R^4$ and $R^5$ form a group =X, where =X is preferably an oxygen atom;

$R^6$ and $R^7$ together preferably form a $C_2$–$C_5$-alkylene or $C_2$–$C_5$-alkenylene chain which may be interrupted once or twice by an oxygen atom, or form a group =X, where X is preferably an oxygen atom or $NR^{10}$;
  especially preferably $R^4$ [sic] and $R^5$ [sic] form a group =X, where =X is preferably an oxygen atom;

n is two;

$R^5$ and $R^6$ together, if they are attached to adjacent carbon atoms and if $R^4$ and $R^7$ are each hydrogen, preferably form a $C_3$–$C_4$-alkylene or $C_3$–$C_4$-alkenylene chain which may be interrupted by a nitrogen or an oxygen atom;

$R^8$ and $R^9$ are each hydrogen, nitro, halogen, cyano, $C_1$–$C_4$-alkyl, $C_5$–$C_6$-cycloalkyl, $C_5$–$C_6$-cycloalkenyl, $C_5$–$C_6$-heterocyclyl, —$OR^{10}$, —$SR^{10}$, —$COR^{10}$, —$COOR^{10}$, —$CONR^3R^{10}$, phenyl, phenyl-$C_1$–$C_4$-alkyl and five- or six-membered hetaryl,
  where the alkyl and cycloalkyl radicals mentioned and $R^3$ and $R^{10}$ of the radicals —$OR^{10}$, —$SR^{10}$, —$COR^{10}$, —$COOR^{10}$, —$CONR^3R^{10}$ may be partially or fully halogenated and/or may carry one to three of the following groups:
    nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl;

$R^{10}$ is hydrogen, $C_1$–$C_4$-alkyl, $C_1$–$C_4$-haloalkyl, $C_2$–$C_4$-alkenyl, phenyl or phenyl-$C_1$–$C_4$-alkyl, where the phenyl radical mentioned may be partially or fully halogenated and/or may carry one to three of the following groups:
  nitro, cyano, $C_1$–$C_4$-alkyl, $C_1$–$C_4$-haloalkyl, $C_1$–$C_4$-alkoxy, $C_1$–$C_4$-haloalkoxy, $C_1$–$C_4$-alkoxycarbonyl;

$R^{11}$, $R^{12}$, $R^{14}$ and $R^{16}$ are each hydrogen or $C_1$–$C_4$-alkyl; particularly preferably hydrogen, methyl or ethyl;

$R^{13}$ is hydrogen, $C_1$–$C_4$-alkyl, $C_3$–$C_4$-cycloalkyl, where the last two radicals mentioned may carry one to three of the following substituents: halogen, $C_1$–$C_4$-alkoxy or $C_1$–$C_4$-alkylthio;

tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, 1,3-dioxolan-2-yl, 1,3-dioxan-2-yl, 1,3-oxathiolan-2-yl, 1,3-oxathian-2-yl, 1,3-dithian-2-yl or 1,3-dithiolan-2-yl, where the last six groups mentioned may in each case carry one to three $C_1$–$C_4$-alkyl radicals;

particularly preferably hydrogen, methyl, ethyl, cyclopropyl, di(methoxy)methyl, di(ethoxy)methyl, 2-ethylthiopropyl, tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, 1,3-dioxolan-2-yl, 1,3-dioxan-2-yl, 5,5-dimethyl-1,3-dioxan-2-yl, 1,3-oxathiolan-2-yl, 1,3-oxathian-2-yl, 1,3-dithiolan-2-yl, 5,5-dimethyl-1,3-dithian-2-yl or 1-methylthiocyclopropyl;

$R^{15}$ is hydrogen, $C_1$–$C_4$-alkyl or $C_1$–$C_4$-alkoxycarbonyl; particularly preferably hydrogen, methyl or methoxycarbonyl.

It may also be advantageous for $R^{13}$ and $R^{16}$ to form a π bond, thus generating a double bond system.

The $CR^{13}R^{14}$ unit may also be advantageously replaced by C=O.

Particular preference is given to the compounds of the formula Ia, where $R^1$ is attached in position 2 and $R^2$ is attached in position 4 of the phenyl ring.

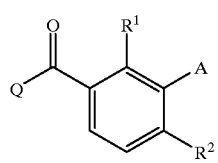

Ia

Most particularly preferred are the compounds of the formula Ia where the substituents $R^1$, $R^2$ and Q are each as defined above, A is a group of the formula IIIa [sic] or IIIb [sic] and $R^4$–$R^7$ are each hydrogen, hydroxyl, amino, halogen, $C_1$–$C_4$-alkyl, $C_5$–$C_6$-cycloalkyl, phenyl, —$OR^{10}$, —$SO_2R^{10}$, —$OSO_2R^{10}$, $PO_3(R^{10})_2$, —$OPO_3(R^{10})_2$, —$NR^3R^{10}$ or —$OCOR^{10}$, where the alkyl and cycloalkyl radicals mentioned and $R^3$ and $R^{10}$ of the radicals —$OR^{10}$, —$SO_2R^{10}$, —$OSO_2R^{10}$, —$PO_3(R^{10})_2$, —$OPO_3(R^{10})_2$, —$NR^3R^{10}$, —$OCOR^{10}$ may be partially or fully halogenated and/or may carry one to three of the following groups:

hydroxyl, amino, cyano, $R^{10}$, —$OR^{10}$, —$NR^3R^{10}$, —$OCOR^{10}$, —$CO_2R^{10}$, $C_1$–$C_4$-alkylcarbonyl, $C_1$–$C_4$-alkylsulfonyl, phenyl, benzyl, phenoxy and benzyloxy, where the last four radicals mentioned may in turn be substituted.

Additionally, those compounds of the formula Ia according to the invention are most particularly preferred where the substituents $R^1$, $R^2$ and Q are each as defined above, A is a group of the formula IIIa [sic] or IIIb [sic] and $R^4$ and $R^5$ together form a $C_2$–$C_5$-alkylene or $C_2$–$C_5$-alkenylene chain which may be interrupted once or twice by an oxygen atom, or form a group =X, where X is preferably an oxygen atom;
and/or $R^6$ and $R^7$ together form a $C_2$–$C_5$-alkylene or $C_2$–$C_5$-alkenylene chain which may be interrupted once or twice by an oxygen atom, or form a group =X, where X is preferably an oxygen atom.

Furthermore, those compounds of the [lacuna] Ia according to the invention are most particularly preferred where the variables $R^1$, $R^2$ and Q are each as defined above, A is a group of the formula IIIa [sic] or IIIb [sic] and $R^5$ and $R^6$ together, if they are attached to adjacent carbon atoms and if $R^4$ and $R^7$ are each hydrogen, form a $C_3$–$C_4$-alkylene or $C_3$–$C_4$-alkenylene chain which may be interrupted by a nitrogen or an oxygen atom.

Most particularly preferred are those compounds of the formula Ia where the variables $R^1$, $R^2$ and Q are each as defined above, A is a group of the formula IVb and $R^8$ and $R^9$ are each hydrogen, nitro, halogen, cyano, $C_1$–$C_4$-alkyl, $C_5$–$C_6$-cycloalkyl, $C_5$–$C_6$-cycloalkenyl, $C_5$–$C_6$-heterocyclyl, —$OR^{10}$, —$COR^{10}$, —$COOR^{10}$, —$CONR^3R^{10}$, phenyl, phenyl-$C_1$–$C_4$-alkyl and five- or six-membered hetaryl, where the alkyl and cycloalkyl radicals mentioned and $R^3$ and $R^{10}$ of the radicals —$OR^{10}$, —$COR^{10}$, —$COOR^{10}$, —$CONR^3R^{10}$ may be partially or fully halogenated and/or may carry one to three of the following groups:

hydroxyl, amino, cyano, $R^{10}$, —$OR^{10}$, —$NR^3R^{10}$, —$OCOR^{10}$, —$CO_2R^{10}$, $C_1$–$C_4$-alkylcarbonyl, $C_1$–$C_4$-alkylsulfonyl, phenyl, benzyl, phenoxy and benzyloxy, where the last four radicals mentioned may in turn be substituted.

Additionally, those compounds of the formula Ia according to the invention are most particularly preferred where the variables $R^1$, $R^2$ and Q are each as defined above, A is a group of the formula IVb and $R^8$ and $R^9$ together form a $C_2$–$C_5$-alkylene or $C_2$–$C_5$-alkenylene chain which may be interrupted once or twice by an oxygen atom.

Very particularly preferred are the compounds Ib of Tables 1 to 36.

TABLE A

| No. | $R^3$ | $R^4$ | $R^5$ | $R^6$ | $R^7$ |
|---|---|---|---|---|---|
| 1 | H | OH | H | H | H |
| 2 | H | OH | —$CH_3$ | H | H |
| 3 | H | OH | —$C_2H_5$ | H | H |
| 4 | H | OH | —$C_3H_7$ | H | H |
| 5 | H | OH | —$C_4H_9$ | H | H |
| 6 | H | OH | —CH=$CH_2$ | H | H |
| 7 | H | OH | —$CH_2$CH=$CH_2$ | H | H |
| 8 | H | OH | —$CH_2$CH=CHPh | H | H |
| 9 | H | OH | —$CH_2$CH=$CHCH_3$ | H | H |
| 10 | H | OH | —C≡CH | H | H |
| 11 | H | OH | —C≡$CCH_3$ | H | H |
| 12 | H | OH | —C≡CPh | H | H |
| 13 | H | OH | Ph | H | H |
| 14 | H | OH | —$CH_2$Ph | H | H |
| 15 | H | OH | cyclopropyl | H | H |
| 16 | H | OH | cyclobutyl | H | H |
| 17 | H | OH | cyclopentyl | H | H |
| 18 | H | OH | cyclohexyl | H | H |
| 19 | H | OH | OH | H | H |
| 20 | H | OH | —$OCH_3$ | H | H |
| 21 | H | OH | —$OC_2H_5$ | H | H |
| 22 | H | OH | —$OC_3H_7$ | H | H |
| 23 | H | OH | —$OC_4H_9$ | H | H |
| 24 | H | OH | —$OCH_2$CH=$CH_2$ | H | H |
| 25 | H | OH | —OPh | H | H |
| 26 | H | OH | —$OCH_2$Ph | H | H |
| 27 | H | OH | —Ocyclopropyl | H | H |

TABLE A-continued

| No. | R³ | R⁴ | R⁵ | R⁶ | R⁷ |
|---|---|---|---|---|---|
| 28 | H | OH | —Ocyclobutyl | H | H |
| 29 | H | OH | —Ocyclopentyl | H | H |
| 30 | H | OH | —Ocyclohexyl | H | H |
| 31 | H | OH | SH | H | H |
| 32 | H | OH | —SCH₃ | H | H |
| 33 | H | OH | —SC₂H₅ | H | H |
| 34 | H | OH | —SC₃H₇ | H | H |
| 35 | H | OH | —SC₄H₉ | H | H |
| 36 | H | OH | —SCH₂CH=CH₂ | H | H |
| 37 | H | OH | —SPh | H | H |
| 38 | H | OH | —SCH₂Ph | H | H |
| 39 | H | OH | —Scyclopropyl | H | H |
| 40 | H | OH | —Scyclobutyl | H | H |
| 41 | H | OH | —Scyclopentyl | H | H |
| 42 | H | OH | —Scyclohexyl | H | H |
| 43 | H | OH | NH₂ | H | H |
| 44 | H | OH | —NHCH₃ | H | H |
| 45 | H | OH | —NHC₂H₅ | H | H |
| 46 | H | OH | —NHC₃H₇ | H | H |
| 47 | H | OH | —NHC₄H₉ | H | H |
| 48 | H | OH | —NHCH₂CH=CH₂ | H | H |
| 49 | H | OH | —NHPh | H | H |
| 50 | H | OH | —NHCH₂Ph | H | H |
| 51 | H | OH | —NHcyclopropyl | H | H |
| 52 | H | OH | —NHcyclobutyl | H | H |
| 53 | H | OH | —NHcyclopentyl | H | H |
| 54 | H | OH | —NHcyclohexyl | H | H |
| 55 | H | OH | —N(CH₃)₂ | H | H |
| 56 | H | OH | —N(CH₃)(C₂H₅) | H | H |
| 57 | H | OH | —N(C₂H₅)₂ | H | H |
| 58 | H | OH | —N(CH₃)(C₃H₇) | H | H |
| 59 | H | OH | —N(CH₃)C₄H₉ | H | H |
| 60 | H | OH | —N(CH₃)(CH₂CH=CH₂) | H | H |
| 61 | H | OH | —N(CH₃)Ph | H | H |
| 62 | H | OH | —N(C₂H₅)Ph | H | H |
| 63 | H | OH | —N(Ph)₂ | H | H |
| 64 | H | OH | —N(C₂H₅)(CH₂Ph) | H | H |
| 65 | H | OH | —N(CH₂Ph)₂ | H | H |
| 66 | H | OH | —N(CH₃)(CH₂Ph) | H | H |
| 67 | H | OH | —N(CH₃)cyclopropyl | H | H |
| 68 | H | OH | —N(CH₃)cyclobutyl | H | H |
| 69 | H | OH | —N(CH₃)cyclopentyl | H | H |
| 70 | H | OH | —N(CH₃)cyclohexyl | H | H |
| 71 | H | —OSi(CH₃)₃ | H | H | H |
| 72 | H | —OSi(CH₃)₃ | —CH₃ | H | H |
| 73 | H | —OSi(CH₃)₃ | —C₂H₅ | H | H |
| 74 | H | —OSi(CH₃)₃ | —C₃H₇ | H | H |
| 75 | H | —OSi(CH₃)₃ | —C₄H₉ | H | H |
| 76 | H | —OSi(CH₃)₃ | —CH=CH₂ | H | H |
| 77 | H | —OSi(CH₃)₃ | —CH₂CH=CH₂ | H | H |
| 78 | H | —OSi(CH₃)₃ | —CH₂CH=CHPh | H | H |
| 79 | H | —OSi(CH₃)₃ | —CH₂CH=CHCH₃ | H | H |
| 80 | H | —OSi(CH₃)₃ | —C≡H | H | H |
| 81 | H | —OSi(CH₃)₃ | —C≡CCH₃ | H | H |
| 82 | H | —OSi(CH₃)₃ | —C≡CPh | H | H |
| 83 | H | —OSi(CH₃)₃ | Ph | H | H |
| 84 | H | —OSi(CH₃)₃ | —CH₂Ph | H | H |
| 85 | H | —OSi(CH₃)₃ | cyclopropyl | H | H |
| 86 | H | —OSi(CH₃)₃ | cyclobutyl | H | H |
| 87 | H | —OSi(CH₃)₃ | cyclopentyl | H | H |
| 88 | H | —OSi(CH₃)₃ | cyclohexyl | H | H |
| 89 | H | —OSi(CH₃)₃ | OH | H | H |
| 90 | H | —OSi(CH₃)₃ | —OCH₃ | H | H |
| 91 | H | —OSi(CH₃)₃ | —OC₂H₅ | H | H |
| 92 | H | —OSi(CH₃)₃ | —OC₃H₇ | H | H |
| 93 | H | —OSi(CH₃)₃ | —OC₄H₉ | H | H |
| 94 | H | —OSi(CH₃)₃ | —OCH₂CH=CH₂ | H | H |
| 95 | H | —OSi(CH₃)₃ | —OPh | H | H |
| 96 | H | —OSi(CH₃)₃ | —OCH₂Ph | H | H |
| 97 | H | —OSi(CH₃)₃ | —Ocyclopropyl | H | H |
| 98 | H | —OSi(CH₃)₃ | —Ocyclobutyl | H | H |
| 99 | H | —OSi(CH₃)₃ | —Ocyclopentyl | H | H |
| 100 | H | —OSi(CH₃)₃ | —Ocyclohexyl | H | H |
| 101 | H | —OSi(CH₃)₃ | SH | H | H |
| 102 | H | —OSi(CH₃)₃ | —SCH₃ | H | H |
| 103 | H | —OSi(CH₃)₃ | —SC₂H₅ | H | H |
| 104 | H | —OSi(CH₃)₃ | —SC₃H₇ | H | H |
| 105 | H | —OSi(CH₃)₃ | —SC₄H₉ | H | H |
| 106 | H | —OSi(CH₃)₃ | —SCH₂CH=CH₂ | H | H |
| 107 | H | —OSi(CH₃)₃ | —SPh | H | H |
| 108 | H | —OSi(CH₃)₃ | —SCH₂Ph | H | H |
| 109 | H | —OSi(CH₃)₃ | —Scyclopropyl | H | H |
| 110 | H | —OSi(CH₃)₃ | —Scyclobutyl | H | H |
| 111 | H | —OSi(CH₃)₃ | —Scyclopentyl | H | H |
| 112 | H | —OSi(CH₃)₃ | —Scyclohexyl | H | H |
| 113 | H | —OSi(CH₃)₃ | NH₂ | H | H |
| 114 | H | —OSi(CH₃)₃ | —NHCH₃ | H | H |
| 115 | H | —OSi(CH₃)₃ | —NHC₂H₅ | H | H |
| 116 | H | —OSi(CH₃)₃ | —NHC₃H₇ | H | H |
| 117 | H | —OSi(CH₃)₃ | —NHC₄H₉ | H | H |
| 118 | H | —OSi(CH₃)₃ | —NHCH₂CH=CH₂ | H | H |
| 119 | H | —OSi(CH₃)₃ | —NHPh | H | H |
| 120 | H | —OSi(CH₃)₃ | —NHCH₂Ph | H | H |
| 121 | H | —OSi(CH₃)₃ | —NHcyclopropyl | H | H |
| 122 | H | —OSi(CH₃)₃ | —NHcyclobutyl | H | H |
| 123 | H | —OSi(CH₃)₃ | —NHcyclopentyl | H | H |
| 124 | H | —OSi(CH₃)₃ | —NHcyclohexyl | H | H |
| 125 | H | —OSi(CH₃)₃ | —N(CH₃)₂ | H | H |
| 126 | H | —OSi(CH₃)₃ | —N(CH₃)(C₂H₅) | H | H |
| 127 | H | —OSi(CH₃)₃ | —N(C₂H₅)₂ | H | H |
| 128 | H | —OSi(CH₃)₃ | —N(CH₃)(C₃H₇) | H | H |
| 129 | H | —OSi(CH₃)₃ | —N(CH₃)C₄H₉ | H | H |
| 130 | H | —OSi(CH₃)₃ | —N(CH₃)(CH₂CH=CH₂) | H | H |
| 131 | H | —OSi(CH₃)₃ | —N(CH₃)Ph | H | H |
| 132 | H | —OSi(CH₃)₃ | —N(C₂H₅)Ph | H | H |
| 133 | H | —OSi(CH₃)₃ | —N(Ph)₂ | H | H |
| 134 | H | —OSi(CH₃)₃ | —N(C₂H₅)(CH₂Ph) | H | H |
| 135 | H | —OSi(CH₃)₃ | —N(CH₂Ph)₂ | H | H |
| 136 | H | —OSi(CH₃)₃ | —N(CH₃)(CH₂Ph) | H | H |
| 137 | H | —OSi(CH₃)₃ | —N(CH₃)cyclopropyl | H | H |
| 138 | H | —OSi(CH₃)₃ | —N(CH₃)cyclobutyl | H | H |
| 139 | H | —OSi(CH₃)₃ | —N(CH₃)cyclopentyl | H | H |
| 140 | H | —OSi(CH₃)₃ | —N(CH₃)cyclohexyl | H | H |
| 141 | H | —OCH₃ | H | H | H |
| 142 | H | —OCH₃ | —CH₃ | H | H |
| 143 | H | —OCH₃ | —C₂H₅ | H | H |
| 144 | H | —OCH₃ | —C₃H₇ | H | H |
| 145 | H | —OCH₃ | —C₄H₉ | H | H |
| 146 | H | —OCH₃ | —CH=CH₂ | H | H |
| 147 | H | —OCH₃ | —CH₂CH=CH₂ | H | H |
| 148 | H | —OCH₃ | —CH₂CH=CHPh | H | H |
| 149 | H | —OCH₃ | —CH₂CH=CHCH₃ | H | H |
| 150 | H | —OCH₃ | —C≡CH | H | H |
| 151 | H | —OCH₃ | —C≡CCH₃ | H | H |
| 152 | H | —OCH₃ | —C≡CPh | H | H |
| 153 | H | —OCH₃ | Ph | H | H |
| 154 | H | —OCH₃ | —CH₂Ph | H | H |
| 155 | H | —OCH₃ | cyclopropyl | H | H |
| 156 | H | —OCH₃ | cyclobutyl | H | H |
| 157 | H | —OCH₃ | cyclopentyl | H | H |
| 158 | H | —OCH₃ | cyclohexyl | H | H |
| 159 | H | —OCH₃ | OH | H | H |
| 160 | H | —OCH₃ | —OCH₃ | H | H |
| 161 | H | —OCH₃ | —OC₂H₅ | H | H |
| 162 | H | —OCH₃ | —OC₃H₇ | H | H |
| 163 | H | —OCH₃ | —OC₄H₉ | H | H |
| 164 | H | —OCH₃ | —OCH₂CH=CH₂ | H | H |
| 165 | H | —OCH₃ | —OPh | H | H |
| 166 | H | —OCH₃ | —OCH₂Ph | H | H |
| 167 | H | —OCH₃ | —Ocyclopropyl | H | H |
| 168 | H | —OCH₃ | —Ocyclobutyl | H | H |
| 169 | H | —OCH₃ | —Ocyclopentyl | H | H |
| 170 | H | —OCH₃ | —Ocyclohexyl | H | H |
| 171 | H | —OCH₃ | SH | H | H |
| 172 | H | —OCH₃ | —SCH₃ | H | H |
| 173 | H | —OCH₃ | —SC₂H₅ | H | H |
| 174 | H | —OCH₃ | —SC₃H₇ | H | H |
| 175 | H | —OCH₃ | —SC₄H₉ | H | H |
| 176 | H | —OCH₃ | —SCH₂CH=CH₂ | H | H |
| 177 | H | —OCH₃ | —SPh | H | H |
| 178 | H | —OCH₃ | —SCH₂Ph | H | H |
| 179 | H | —OCH₃ | —Scyclopropyl | H | H |
| 180 | H | —OCH₃ | —Scyclobutyl | H | H |
| 181 | H | —OCH₃ | —Scyclopentyl | H | H |

TABLE A-continued

| No. | R³ | R⁴ | R⁵ | R⁶ | R⁷ |
|---|---|---|---|---|---|
| 182 | H | —OCH₃ | —Scyclohexyl | H | H |
| 183 | H | —OCH₃ | NH₂ | H | H |
| 184 | H | —OCH₃ | —NHCH₃ | H | H |
| 185 | H | —OCH₃ | —NHC₂H₅ | H | H |
| 186 | H | —OCH₃ | —NHC₃H₇ | H | H |
| 187 | H | —OCH₃ | —NHC₄H₉ | H | H |
| 188 | H | —OCH₃ | —NHCH₂CH=CH₂ | H | H |
| 189 | H | —OCH₃ | —NHPh | H | H |
| 190 | H | —OCH₃ | —NHCH₂Ph | H | H |
| 191 | H | —OCH₃ | —NHcyclopropyl | H | H |
| 192 | H | —OCH₃ | —NHcyclobutyl | H | H |
| 193 | H | —OCH₃ | —NHcyclopentyl | H | H |
| 194 | H | —OCH₃ | —NHcyclohexyl | H | H |
| 195 | H | —OCH₃ | —N(CH₃)₂ | H | H |
| 196 | H | —OCH₃ | —N(CH₃)(C₂H₅) | H | H |
| 197 | H | —OCH₃ | —N(C₂H₅)₂ | H | H |
| 198 | H | —OCH₃ | —N(CH₃)(C₃H₇) | H | H |
| 199 | H | —OCH₃ | —N(CH₃)C₄H₉ | H | H |
| 200 | H | —OCH₃ | —N(CH₃)(CH₂CH=CH₂) | H | H |
| 201 | H | —OCH₃ | —N(CH₃)Ph | H | H |
| 202 | H | —OCH₃ | —N(C₂H₅)Ph | H | H |
| 203 | H | —OCH₃ | —N(Ph)₂ | H | H |
| 204 | H | —OCH₃ | —N(C₂H₅)(CH₂Ph) | H | H |
| 205 | H | —OCH₃ | —N(CH₂Ph)₂ | H | H |
| 206 | H | —OCH₃ | —N(CH₃)(CH₂Ph) | H | H |
| 207 | H | —OCH₃ | —N(CH₃)cyclopropyl | H | H |
| 208 | H | —OCH₃ | —N(CH₃)cyclobutyl | H | H |
| 209 | H | —OCH₃ | —N(CH₃)cyclopentyl | H | H |
| 210 | H | —OCH₃ | —N(CH₃)cyclohexyl | H | H |
| 211 | H | —OSO₂CH₃ | H | H | H |
| 212 | H | —OSO₂CH₃ | —CH₃ | H | H |
| 213 | H | —OSO₂CH₃ | —C₂H₅ | H | H |
| 214 | H | —OSO₂CH₃ | —C₃H₇ | H | H |
| 215 | H | —OSO₂CH₃ | —C₄H₉ | H | H |
| 216 | H | —OSO₂CH₃ | —CH=CH₂ | H | H |
| 217 | H | —OSO₂CH₃ | —CH₂CH=CH₂ | H | H |
| 218 | H | —OSO₂CH₃ | —CH₂CH=CHPh | H | H |
| 219 | H | —OSO₂CH₃ | —CH₂CH=CHCH₃ | H | H |
| 220 | H | —OSO₂CH₃ | —C≡CH | H | H |
| 221 | H | —OSO₂CH₃ | —C≡CCH₃ | H | H |
| 222 | H | —OSO₂CH₃ | —C≡CPh | H | H |
| 223 | H | —OSO₂CH₃ | Ph | H | H |
| 224 | H | —OSO₂CH₃ | —CH₂Ph | H | H |
| 225 | H | —OSO₂CH₃ | cyclopropyl | H | H |
| 226 | H | —OSO₂CH₃ | cyclobutyl | H | H |
| 227 | H | —OSO₂CH₃ | cyclopentyl | H | H |
| 228 | H | —OSO₂CH₃ | cyclohexyl | H | H |
| 229 | H | —OSO₂CH₃ | OH | H | H |
| 230 | H | —OSO₂CH₃ | —OCH₃ | H | H |
| 231 | H | —OSO₂CH₃ | —OC₂H₅ | H | H |
| 232 | H | —OSO₂CH₃ | —OC₃H₇ | H | H |
| 233 | H | —OSO₂CH₃ | —OC₄H₉ | H | H |
| 234 | H | —OSO₂CH₃ | —OCH₂CH=CH₂ | H | H |
| 235 | H | —OSO₂CH₃ | —OPh | H | H |
| 236 | H | —OSO₂CH₃ | —OCH₂Ph | H | H |
| 237 | H | —OSO₂CH₃ | —Ocyclopropyl | H | H |
| 238 | H | —OSO₂CH₃ | —Ocyclobutyl | H | H |
| 239 | H | —OSO₂CH₃ | —Ocyclopentyl | H | H |
| 240 | H | —OSO₂CH₃ | —Ocyclohexyl | H | H |
| 241 | H | —OSO₂CH₃ | SH | H | H |
| 242 | H | —OSO₂CH₃ | —SCH₃ | H | H |
| 243 | H | —OSO₂CH₃ | —SC₂H₅ | H | H |
| 244 | H | —OSO₂CH₃ | —SC₃H₇ | H | H |
| 245 | H | —OSO₂CH₃ | —SC₄H₉ | H | H |
| 246 | H | —OSO₂CH₃ | —SCH₂CH=CH₂ | H | H |
| 247 | H | —OSO₂CH₃ | —SPh | H | H |
| 248 | H | —OSO₂CH₃ | —SCH₂Ph | H | H |
| 249 | H | —OSO₂CH₃ | —Scyclopropyl | H | H |
| 250 | H | —OSO₂CH₃ | —Scyclobutyl | H | H |
| 251 | H | —OSO₂CH₃ | —Scyclopentyl | H | H |
| 252 | H | —OSO₂CH₃ | —Scyclohexyl | H | H |
| 253 | H | —OSO₂CH₃ | NH₂ | H | H |
| 254 | H | —OSO₂CH₃ | —NHCH₃ | H | H |
| 255 | H | —OSO₂CH₃ | —NHC₂H₅ | H | H |
| 256 | H | —OSO₂CH₃ | —NHC₃H₇ | H | H |
| 257 | H | —OSO₂CH₃ | —NHC₄H₉ | H | H |
| 258 | H | —OSO₂CH₃ | —NHCH₂CH=CH₂ | H | H |
| 259 | H | —OSO₂CH₃ | —NHPh | H | H |
| 260 | H | —OSO₂CH₃ | —NHCH₂Ph | H | H |
| 261 | H | —OSO₂CH₃ | —NHcyclopropyl | H | H |
| 262 | H | —OSO₂CH₃ | —NHcyclobutyl | H | H |
| 263 | H | —OSO₂CH₃ | —NHcyclopentyl | H | H |
| 264 | H | —OSO₂CH₃ | —NHcyclohexyl | H | H |
| 265 | H | —OSO₂CH₃ | —N(CH₃)₂ | H | H |
| 266 | H | —OSO₂CH₃ | —N(CH₃)(C₂H₅) | H | H |
| 267 | H | —OSO₂CH₃ | —N(C₂H₅)₂ | H | H |
| 268 | H | —OSO₂CH₃ | —N(CH₃)(C₃H₇) | H | H |
| 269 | H | —OSO₂CH₃ | —N(CH₃)C₄H₉ | H | H |
| 270 | H | —OSO₂CH₃ | —N(CH₃)(CH₂CH=CH₂) | H | H |
| 271 | H | —OSO₂CH₃ | —N(CH₃)Ph | H | H |
| 272 | H | —OSO₂CH₃ | —N(C₂H₅)Ph | H | H |
| 273 | H | —OSO₂CH₃ | —N(Ph)₂ | H | H |
| 274 | H | —OSO₂CH₃ | —N(C₂H₅)(CH₂Ph) | H | H |
| 275 | H | —OSO₂CH₃ | —N(CH₂Ph)₂ | H | H |
| 276 | H | —OSO₂CH₃ | —N(CH₃)(CH₂Ph) | H | H |
| 277 | H | —OSO₂CH₃ | —N(CH₃)cyclopropyl | H | H |
| 278 | H | —OSO₂CH₃ | —N(CH₃)cyclobutyl | H | H |
| 279 | H | —OSO₂CH₃ | —N(CH₃)cyclopentyl | H | H |
| 280 | H | —OSO₂CH₃ | —N(CH₃)cyclohexyl | H | H |
| 281 | —CH₃ | OH | H | H | H |
| 282 | —CH₃ | OH | —CH₃ | H | H |
| 283 | —CH₃ | OH | —C₂H₅ | H | H |
| 284 | —CH₃ | OH | —C₃H₇ | H | H |
| 285 | —CH₃ | OH | —C₄H₉ | H | H |
| 286 | —CH₃ | OH | —CH=CH₂ | H | H |
| 287 | —CH₃ | OH | —CH₂CH=CH₂ | H | H |
| 288 | —CH₃ | OH | —CH₂CH=CHPh | H | H |
| 289 | —CH₃ | OH | —CH₂CH=CHCH₃ | H | H |
| 290 | —CH₃ | OH | —C≡CH | H | H |
| 291 | —CH₃ | OH | —C≡CCH₃ | H | H |
| 292 | —CH₃ | OH | —C≡CPh | H | H |
| 293 | —CH₃ | OH | Ph | H | H |
| 294 | —CH₃ | OH | —CH₂Ph | H | H |
| 295 | —CH₃ | OH | cyclopropyl | H | H |
| 296 | —CH₃ | OH | cyclobutyl | H | H |
| 297 | —CH₃ | OH | cyclopentyl | H | H |
| 298 | —CH₃ | OH | cyclohexyl | H | H |
| 299 | —CH₃ | OH | OH | H | H |
| 300 | —CH₃ | OH | —OCH₃ | H | H |
| 301 | —CH₃ | OH | —OC₂H₅ | H | H |
| 302 | —CH₃ | OH | —OC₃H₇ | H | H |
| 303 | —CH₃ | OH | —OC₄H₉ | H | H |
| 304 | —CH₃ | OH | —OCH₂CH=CH₂ | H | H |
| 305 | —CH₃ | OH | —OPh | H | H |
| 306 | —CH₃ | OH | —OCH₂Ph | H | H |
| 307 | —CH₃ | OH | —Ocyclopropyl | H | H |
| 308 | —CH₃ | OH | —Ocyclobutyl | H | H |
| 309 | —CH₃ | OH | —Ocyclopentyl | H | H |
| 310 | —CH₃ | OH | —Ocyclohexyl | H | H |
| 311 | —CH₃ | OH | SH | H | H |
| 312 | —CH₃ | OH | —SCH₃ | H | H |
| 313 | —CH₃ | OH | —SC₂H₅ | H | H |
| 314 | —CH₃ | OH | —SC₃H₇ | H | H |
| 315 | —CH₃ | OH | —SC₄H₉ | H | H |
| 316 | —CH₃ | OH | —SCH₂CH=CH₂ | H | H |
| 317 | —CH₃ | OH | —SPh | H | H |
| 318 | —CH₃ | OH | —SCH₂Ph | H | H |
| 319 | —CH₃ | OH | —Scyclopropyl | H | H |
| 320 | —CH₃ | OH | —Scyclobutyl | H | H |
| 321 | —CH₃ | OH | —Scyclopentyl | H | H |
| 322 | —CH₃ | OH | —Scyclohexyl | H | H |
| 323 | —CH₃ | OH | NH₂ | H | H |
| 324 | —CH₃ | OH | —NHCH₃ | H | H |
| 325 | —CH₃ | OH | —NHC₂H₅ | H | H |
| 326 | —CH₃ | OH | —NHC₃H₇ | H | H |
| 327 | —CH₃ | OH | —NHC₄H₉ | H | H |
| 328 | —CH₃ | OH | —NHCH₂CH=CH₂ | H | H |
| 329 | —CH₃ | OH | —NHPh | H | H |
| 330 | —CH₃ | OH | —NHCH₂Ph | H | H |
| 331 | —CH₃ | OH | —NHcyclopropyl | H | H |
| 332 | —CH₃ | OH | —NHcyclobutyl | H | H |
| 333 | —CH₃ | OH | —NHcyclopentyl | H | H |
| 334 | —CH₃ | OH | —NHcyclohexyl | H | H |
| 335 | —CH₃ | OH | —N(CH₃)₂ | H | H |

TABLE A-continued

| No. | R³ | R⁴ | R⁵ | R⁶ | R⁷ |
|---|---|---|---|---|---|
| 336 | —CH₃ | OH | —N(CH₃)(C₂H₅) | H | H |
| 337 | —CH₃ | OH | —N(C₂H₅)₂ | H | H |
| 338 | —CH₃ | OH | —N(CH₃)(C₃H₇) | H | H |
| 339 | —CH₃ | OH | —N(CH₃)C₄H₉ | H | H |
| 340 | —CH₃ | OH | —N(CH₃)(CH₂CH=CH₂) | H | H |
| 341 | —CH₃ | OH | —N(CH₃)Ph | H | H |
| 342 | —CH₃ | OH | —N(C₂H₅)Ph | H | H |
| 343 | —CH₃ | OH | —N(Ph)₂ | H | H |
| 344 | —CH₃ | OH | —N(C₂H₅)(CH₂Ph) | H | H |
| 345 | —CH₃ | OH | —N(CH₂Ph)₂ | H | H |
| 346 | —CH₃ | OH | —N(CH₃)(CH₂Ph) | H | H |
| 347 | —CH₃ | OH | —N(CH₃)cyclopropyl | H | H |
| 348 | —CH₃ | OH | —N(CH₃)cyclobutyl | H | H |
| 349 | —CH₃ | OH | —N(CH₃)cyclopentyl | H | H |
| 350 | —CH₃ | OH | —N(CH₃)cyclohexyl | H | H |
| 351 | H | OH | H | —CH₃ | H |
| 352 | H | OH | —CH₃ | —CH₃ | H |
| 353 | H | OH | —C₂H₅ | —CH₃ | H |
| 354 | H | OH | —C₃H₇ | —CH₃ | H |
| 355 | H | OH | —C₄H₉ | —CH₃ | H |
| 356 | H | OH | —CH=CH₂ | —CH₃ | H |
| 357 | H | OH | —CH₂CH=CH₂ | —CH₃ | H |
| 358 | H | OH | —CH₂CH=CHPh | —CH₃ | H |
| 359 | H | OH | —CH₂CH=CHCH₃ | —CH₃ | H |
| 360 | H | OH | —C≡CH | —CH₃ | H |
| 361 | H | OH | —C≡CCH₃ | —CH₃ | H |
| 362 | H | OH | —C≡CPh | —CH₃ | H |
| 363 | H | OH | Ph | —CH₃ | H |
| 364 | H | OH | —CH₂Ph | —CH₃ | H |
| 365 | H | OH | cyclopropyl | —CH₃ | H |
| 366 | H | OH | cyclobutyl | —CH₃ | H |
| 367 | H | OH | cyclopentyl | —CH₃ | H |
| 368 | H | OH | cyclohexyl | —CH₃ | H |
| 369 | H | OH | OH | —CH₃ | H |
| 370 | H | OH | —OCH₃ | —CH₃ | H |
| 371 | H | OH | —OC₂H₅ | —CH₃ | H |
| 372 | H | OH | —OC₃H₇ | —CH₃ | H |
| 373 | H | OH | —OC₄H₉ | —CH₃ | H |
| 374 | H | OH | —OCH₂CH=CH₂ | —CH₃ | H |
| 375 | H | OH | —OPh | —CH₃ | H |
| 376 | H | OH | —OCH₂Ph | —CH₃ | H |
| 377 | H | OH | —Ocyclopropyl | —CH₃ | H |
| 378 | H | OH | —Ocyclobutyl | —CH₃ | H |
| 379 | H | OH | —Ocyclopentyl | —CH₃ | H |
| 380 | H | OH | —Ocyclohexyl | —CH₃ | H |
| 381 | H | OH | SH | —CH₃ | H |
| 382 | H | OH | —SCH₃ | —CH₃ | H |
| 383 | H | OH | —SC₂H₅ | —CH₃ | H |
| 384 | H | OH | —SC₃H₇ | —CH₃ | H |
| 385 | H | OH | —SC₄H₉ | —CH₃ | H |
| 386 | H | OH | —SCH₂CH=CH₂ | —CH₃ | H |
| 387 | H | OH | —SPh | —CH₃ | H |
| 388 | H | OH | —SCH₂Ph | —CH₃ | H |
| 389 | H | OH | —Scyclopropyl | —CH₃ | H |
| 390 | H | OH | —Scyclobutyl | —CH₃ | H |
| 391 | H | OH | —Scyclopentyl | —CH₃ | H |
| 392 | H | OH | —Scyclohexyl | —CH₃ | H |
| 393 | H | OH | NH₂ | —CH₃ | H |
| 394 | H | OH | —NHCH₃ | —CH₃ | H |
| 395 | H | OH | —NHC₂H₅ | —CH₃ | H |
| 396 | H | OH | —NHC₃H₇ | —CH₃ | H |
| 397 | H | OH | —NHC₄H₉ | —CH₃ | H |
| 398 | H | OH | —NHCH₂CH=CH₂ | —CH₃ | H |
| 399 | H | OH | —NHPh | —CH₃ | H |
| 400 | H | OH | —NHCH₂Ph | —CH₃ | H |
| 401 | H | OH | —NHcyclopropyl | —CH₃ | H |
| 402 | H | OH | —NHcyclobutyl | —CH₃ | H |
| 403 | H | OH | —NHcyclopentyl | —CH₃ | H |
| 404 | H | OH | —NHcyclohexyl | —CH₃ | H |
| 405 | H | OH | —N(CH₃)₂ | —CH₃ | H |
| 406 | H | OH | —N(CH₃)(C₂H₅) | —CH₃ | H |
| 407 | H | OH | —N(C₂H₅)₂ | —CH₃ | H |
| 408 | H | OH | —N(CH₃)(C₃H₇) | —CH₃ | H |
| 409 | H | OH | —N(CH₃)C₄H₉ | —CH₃ | H |
| 410 | H | OH | —N(CH₃)(CH₂CH=CH₂) | —CH₃ | H |
| 411 | H | OH | —N(CH₃)Ph | —CH₃ | H |
| 412 | H | OH | —N(C₂H₅)Ph | —CH₃ | H |
| 413 | H | OH | —N(Ph)₂ | —CH₃ | H |
| 414 | H | OH | —N(C₂H₅)(CH₂Ph) | —CH₃ | H |
| 415 | H | OH | —N(CH₂Ph)₂ | —CH₃ | H |
| 416 | H | OH | —N(CH₃)(CH₂Ph) | —CH₃ | H |
| 417 | H | OH | —N(CH₃)cyclopropyl | —CH₃ | H |
| 418 | H | OH | —N(CH₃)cyclobutyl | —CH₃ | H |
| 419 | H | OH | —N(CH₃)cyclopentyl | —CH₃ | H |
| 420 | H | OH | —N(CH₃)cyclohexyl | —CH₃ | H |
| 421 | H | OH | H | Ph | H |
| 422 | H | OH | —CH₃ | Ph | H |
| 423 | H | OH | —C₂H₅ | Ph | H |
| 424 | H | OH | —C₃H₇ | Ph | H |
| 425 | H | OH | —C₄H₉ | Ph | H |
| 426 | H | OH | —CH=CH₂ | Ph | H |
| 427 | H | OH | —CH₂CH=CH₂ | Ph | H |
| 428 | H | OH | —CH₂CH=CHPh | Ph | H |
| 429 | H | OH | —CH₂CH=CHCH₃ | Ph | H |
| 430 | H | OH | —C≡H | Ph | H |
| 431 | H | OH | —C≡CCH₃ | Ph | H |
| 432 | H | OH | —C≡CPh | Ph | H |
| 433 | H | OH | Ph | Ph | H |
| 434 | H | OH | —CH₂Ph | Ph | H |
| 435 | H | OH | cyclopropyl | Ph | H |
| 436 | H | OH | cyclobutyl | Ph | H |
| 437 | H | OH | cyclopentyl | Ph | H |
| 438 | H | OH | cyclohexyl | Ph | H |
| 439 | H | OH | OH | Ph | H |
| 440 | H | OH | —OCH₃ | Ph | H |
| 441 | H | OH | —OC₂H₅ | Ph | H |
| 442 | H | OH | —OC₃H₇ | Ph | H |
| 443 | H | OH | —OC₄H₉ | Ph | H |
| 444 | H | OH | —OCH₂CH=CH₂ | Ph | H |
| 445 | H | OH | —OPh | Ph | H |
| 446 | H | OH | —OCH₂Ph | Ph | H |
| 447 | H | OH | —Ocyclopropyl | Ph | H |
| 448 | H | OH | —Ocyclobutyl | Ph | H |
| 449 | H | OH | —Ocyclopentyl | Ph | H |
| 450 | H | OH | —Ocyclohexyl | Ph | H |
| 451 | H | OH | SH | Ph | H |
| 452 | H | OH | —SCH₃ | Ph | H |
| 453 | H | OH | —SC₂H₅ | Ph | H |
| 454 | H | OH | —SC₃H₇ | Ph | H |
| 455 | H | OH | —SC₄H₉ | Ph | H |
| 456 | H | OH | —SCH₂CH=CH₂ | Ph | H |
| 457 | H | OH | —SPh | Ph | H |
| 458 | H | OH | —SCH₂Ph | Ph | H |
| 459 | H | OH | —Scyclopropyl | Ph | H |
| 460 | H | OH | —Scyclobutyl | Ph | H |
| 461 | H | OH | —Scyclopentyl | Ph | H |
| 462 | H | OH | —Scyclohexyl | Ph | H |
| 463 | H | OH | NH₂ | Ph | H |
| 464 | H | OH | —NHCH₃ | Ph | H |
| 465 | H | OH | —NHC₂H₅ | Ph | H |
| 466 | H | OH | —NHC₃H₇ | Ph | H |
| 467 | H | OH | —NHC₄H₉ | Ph | H |
| 468 | H | OH | —NHCH₂CH=CH₂ | Ph | H |
| 469 | H | OH | —NHPh | Ph | H |
| 470 | H | OH | —NHCH₂Ph | Ph | H |
| 471 | H | OH | —NHcyclopropyl | Ph | H |
| 472 | H | OH | —NHcyclobutyl | Ph | H |
| 473 | H | OH | —NHcyclopentyl | Ph | H |
| 474 | H | OH | —NHcyclohexyl | Ph | H |
| 475 | H | OH | —N(CH₃)₂ | Ph | H |
| 476 | H | OH | —N(CH₃)(C₂H₅) | Ph | H |
| 477 | H | OH | —N(C₂H₅)₂ | Ph | H |
| 478 | H | OH | —N(CH₃)(C₃H₇) | Ph | H |
| 479 | H | OH | —N(CH₃)C₄H₉ | Ph | H |
| 480 | H | OH | —N(CH₃)(CH₂CH=CH₂) | Ph | H |
| 481 | H | OH | —N(CH₃)Ph | Ph | H |
| 482 | H | OH | —N(C₂H₅)Ph | Ph | H |
| 483 | H | OH | —N(Ph)₂ | Ph | H |
| 484 | H | OH | —N(C₂H₅)(CH₂Ph) | Ph | H |
| 485 | H | OH | —N(CH₂Ph)₂ | Ph | H |
| 486 | H | OH | —N(CH₃)(CH₂Ph) | Ph | H |
| 487 | H | OH | —N(CH₃)cyclopropyl | Ph | H |
| 488 | H | OH | —N(CH₃)cyclobutyl | Ph | H |
| 489 | H | OH | —N(CH₃)cyclopentyl | Ph | H |

TABLE A-continued

| No. | $R^3$ | $R^4$ | $R^5$ | $R^6$ | $R^7$ |
|---|---|---|---|---|---|
| 490 | H | OH | —N(CH$_3$)cyclohexyl | Ph | H |
| 491 | H | H | —OCH$_2$CH$_2$— | | H |
| 492 | CH$_3$ | H | —OCH$_2$CH$_2$— | | H |
| 493 | H | H | —CH$_2$CH$_2$O— | | H |
| 494 | CH$_3$ | H | —CH$_2$CH$_2$O— | | H |
| 495 | H | H | —OCH=CH— | | H |
| 496 | CH$_3$ | H | —OCH=CH— | | H |
| 497 | H | H | —CH=CHO— | | H |
| 498 | CH$_3$ | H | —CH=CHO— | | H |
| 499 | H | H | —OCH$_2$CH$_2$CH$_2$— | | H |
| 500 | CH$_3$ | H | —OCH$_2$CH$_2$CH$_2$— | | H |
| 501 | H | H | —CH$_2$CH$_2$CH$_2$O— | | H |
| 502 | CH$_3$ | H | —CH$_2$CH$_2$CH$_2$O— | | H |
| 503 | H | H | —NHCH$_2$CH$_2$— | | H |
| 504 | CH$_3$ | H | —NHCH$_2$CH$_2$— | | H |
| 505 | H | H | —CH$_2$CH$_2$NH— | | H |
| 506 | CH$_3$ | H | —CH$_2$CH$_2$NH— | | H |
| 507 | H | H | —NHCH=CH— | | H |
| 508 | CH$_3$ | H | —NHCH=CH— | | H |
| 509 | H | H | —CH=CHNH— | | H |
| 510 | CH$_3$ | H | —CH=CHNH— | | H |
| 511 | H | H | —NHCH$_2$CH$_2$CH$_2$— | | H |
| 512 | CH$_3$ | H | —NHCH$_2$CH$_2$CH$_2$— | | H |
| 513 | H | H | —CH$_2$CH$_2$CH$_2$NH— | | H |
| 514 | CH$_3$ | H | —CH$_2$CH$_2$CH$_2$NH— | | H |

The Tables 1–36 below are based on the 2-benzoylcyclohexane-1,3-diones of the formula Ib:

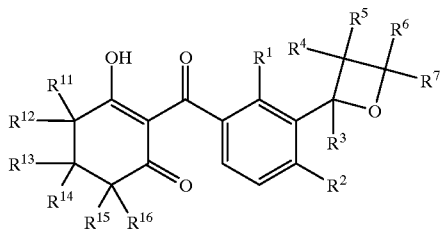

Ib

Table 1: Compounds 1.1–1.514

Compounds of the formula Ib, where $R^1$ is chlorine, $R^2$ is methylsulfonyl, $R^{11}$, $R^{12}$, $R^{13}$, $R^{14}$, $R^{15}$ and $R^{16}$ are each hydrogen and where for each individual compound the substituents $R^3$ to $R^7$ each correspond to one line of Table A.

Table 2: Compounds 2.1–2.514

Compounds of the formula Ib, where $R^1$ and $R^2$ are each chlorine, $R^{11}$, $R^{12}$, $R^{13}$, $R^{14}$, $R^{15}$ and $R^{16}$ are each hydrogen and where for each individual compound the substituents $R^3$ to $R^7$ each correspond to one line of Table A.

Table 3: Compounds 3.1–3.514

Compounds of the formula Ib, where $R^1$ is chlorine, $R^2$ is trifluoromethyl, $R^{11}$, $R^{12}$, $R^{13}$, $R^{14}$, $R^{15}$ and $R^{16}$ are each hydrogen and where for each individual compound the substituents $R^3$ to $R^7$ each correspond to one line of Table A.

Table 4: Compounds 4.1–4.514

Compounds of the formula Ib, where $R^1$ is methyl, $R^2$ is chlorine, $R^{11}$, $R^{12}$, $R^{13}$, $R^{14}$, $R^{15}$ and $R^{16}$ are each hydrogen and where for each individual compound the substituents $R^3$ to $R^7$ each correspond to one line of Table A.

Table 5: Compounds 5.1–5.514

Compounds of the formula Ib, where $R^1$ is methyl, $R^2$ is methylsulfonyl, $R^{11}$, $R^{12}$, $R^{13}$, $R^{14}$, $R^{15}$ and $R^{16}$ are each hydrogen and where for each individual compound the substituents $R^3$ to $R^7$ each correspond to one line of Table A.

Table 6: Compounds 6.1–6.514

Compounds of the formula Ib, where $R^1$ is methyl, $R^2$ is trifluoromethyl, $R^{11}$, $R^{12}$, $R^{13}$, $R^{14}$, $R^{15}$ and $R^{16}$ are each hydrogen and where for each individual compound the substituents $R^3$ to $R^7$ each correspond to one line of Table A.

Table 7: Compounds 7.1–7.514

Compounds of the formula Ib, where $R^1$ is chlorine, $R^2$ is methylsulfonyl, $R^{11}$, $R^{12}$, $R^{15}$ and $R^{16}$ are each hydrogen, $R^{13}$ and $R^{14}$ are each methyl and where for each individual compound the substituents $R^3$ to $R^7$ each correspond to one line of Table A.

Table 8: Compounds 8.1–8.514

Compounds of the formula Ib, where $R^1$ and $R^2$ are each chlorine, $R^{11}$, $R^{12}$, $R^{15}$ and $R^{16}$ are each hydrogen, $R^{13}$ and $R^{14}$ are each methyl and where for each individual compound the substituents $R^3$ to $R^7$ each correspond to one line of Table A.

Table 9: Compounds 9.1–9.514

Compounds of the formula Ib, where $R^1$ is chlorine, $R^2$ is trifluoromethyl, $R^{11}$, $R^{12}$, $R^{15}$ and $R^{16}$ are each hydrogen, $R^{13}$ and $R^{14}$ are each methyl and where for each individual compound the substituents $R^3$ to $R^7$ each correspond to one line of Table A.

Table 10: Compounds 10.1–10.514

Compounds of the formula Ib, where $R^1$ is methyl, $R^2$ is chlorine, $R^{11}$, $R^{12}$, $R^{15}$ and $R^{16}$ are each hydrogen, $R^{13}$ and $R^{14}$ are each methyl and where for each individual compound the substituents $R^3$ to $R^7$ each correspond to one line of Table A.

Table 11: Compounds 11.1–11.514

Compounds of the formula Ib, where $R^1$ is methyl, $R^2$ is methylsulfonyl, $R^{11}$, $R^{12}$, $R^{15}$ and $R^{16}$ are each hydrogen, $R^{13}$ and $R^{14}$ are each methyl and where for each individual compound the substituents $R^3$ to $R^7$ each correspond to one line of Table A.

Table 12: Compounds 12.1–12.514

Compounds of the formula Ib, where $R^1$ is methyl, $R^2$ is trifluoromethyl, $R^{11}$, $R^{12}$, $R^{15}$ and $R^{16}$ are each hydrogen, $R^{13}$ and $R^{14}$ are each methyl and where for each individual compound the substituents $R^3$ to $R^7$ each correspond to one line of Table A.

Table 13: Compounds 13.1–13.514

Compounds of the formula Ib, where $R^1$ is chlorine, $R^2$ is methylsulfonyl, $R^{11}$, $R^{12}$, $R^{13}$ and $R^{14}$ are each hydrogen, $R^{15}$ and $R^{16}$ are each methyl and where for each individual compound the substituents $R^3$ to $R^7$ each correspond to one line of Table A.

Table 14: Compounds 14.1–14.514

Compounds of the formula Ib, where $R^1$ and $R^2$ are each chlorine, $R^{11}$, $R^{12}$, $R^{13}$ and $R^{14}$ are each hydrogen, $R^{15}$ and $R^{16}$ are each methyl and where for each individual compound the substituents $R^3$ to $R^7$ each correspond to one line of Table A.

Table 15: Compounds 15.1–15.514

Compounds of the formula Ib, where $R^1$ is chlorine, $R^2$ is trifluoromethyl, $R^{11}$, $R^{12}$, $R^{13}$ and $R^{14}$ are each hydrogen, $R^{15}$ and $R^{16}$ are each methyl and where for each individual compound the substituents $R^3$ to $R^7$ each correspond to one line of Table A.

Table 16: Compounds 16.1–16.514

Compounds of the formula Ib, where $R^1$ is methyl, $R^2$ is chlorine, $R^{11}$, $R^{12}$, $R^{13}$ and $R^{14}$ are each hydrogen, $R^{15}$ and $R^{16}$ are each methyl and where for each individual compound the substituents $R^3$ to $R^7$ each correspond to one line of Table A.

Table 17: Compounds 17.1–17.514

Compounds of the formula Ib, where $R^1$ is methyl, $R^2$ is methylsulfonyl, $R^{11}$, $R^{12}$, $R^{13}$ and $R^{14}$ are each hydrogen, $R^{15}$ and $R^{16}$ are each methyl and where for each individual compound the substituents $R^3$ to $R^7$ each correspond to one line of Table A.

Table 18: Compounds 18.1–18.514

Compounds of the formula Ib, where $R^1$ is methyl, $R^2$ is trifluoromethyl, $R^{11}$, $R^{12}$, $R^{13}$ and $R^{14}$ are each hydrogen, $R^{15}$ and $R^{16}$ are each methyl and where for each individual compound the substituents $R^3$ to $R^7$ each correspond to one line of Table A.

Table 19: Compounds 19.1–19.514

Compounds of the formula Ib, where $R^1$ is chlorine, $R^2$ is methylsulfonyl, $R^{11}$, $R^{12}$, $R^{15}$ and $R^{16}$ are each methyl, the $CR^{13}R^{14}$ unit forms a group C=O and where for each individual compound the substituents $R^3$ to $R^7$ each correspond to one line of Table A.

Table 20: Compounds 20.1–20.514

Compounds of the formula Ib, where $R^1$ and $R^2$ are each chlorine, $R^{11}$, $R^{12}$, $R^{15}$ and $R^{16}$ are each methyl, the $CR^{13}R^{14}$ unit forms a group C=O and where for each individual compound the substituents $R^3$ to $R^7$ each correspond to one line of Table A.

Table 21: Compounds 21.1–21.514

Compounds of the formula Ib, where $R^1$ is chlorine, $R^2$ is trifluoromethyl, $R^{11}$, $R^{12}$, $R^{15}$ and $R^{16}$ are each methyl, the $CR^{13}R^{14}$ unit forms a group C=O and where for each individual compound the substituents $R^3$ to $R^7$ each correspond to one line of Table A.

Table 22: Compounds 22.1–22.514

Compounds of the formula Ib, where $R^1$ is methyl, $R^2$ is chlorine, $R^{11}$, $R^{12}$, $R^{15}$ and $R^{16}$ are each methyl, the $CR^{13}R^{14}$ unit forms a group C=O and where for each individual compound the substituents $R^3$ to $R^7$ each correspond to one line of Table A.

Table 23: Compounds 23.1–23.514

Compounds of the formula Ib, where $R^1$ is methyl, $R^2$ is methylsulfonyl, $R^{11}$, $R^{12}$, $R^{15}$ and $R^{16}$ are each methyl, the $CR^{13}R^{14}$ unit forms a group C=O and where for each individual compound the substituents $R^3$ to $R^7$ each correspond to one line of Table A.

Table 24: Compounds 24.1–24.514

Compounds of the formula Ib, where $R^1$ is methyl, $R^2$ is trifluoromethyl, $R^{11}$, $R^{12}$, $R^{15}$ and $R^{16}$ are each methyl, the $CR^{13}R^{14}$ unit forms a group C=O and where for each individual compound the substituents $R^3$ to $R^7$ each correspond to one line of Table A.

Table 25: Compounds 25.1–25.514

Compounds of the formula Ib, where $R^1$ is methylsulfonyl, $R^{11}$, $R^{12}$, $R^{13}$, $R^{15}$ and $R^{16}$ are each hydrogen, $R^{14}$ is methyl and where for each individual compound the substituents $R^3$ to $R^7$ each correspond to one line of Table A.

Table 26: Compounds 26.1–26.514

Compounds of the formula Ib, where $R^1$ and $R^2$ are each chlorine, $R^{11}$, $R^{12}$, $R^{13}$, $R^{15}$ and $R^{16}$ are each hydrogen, $R^{14}$ is methyl and where for each individual compound the substituents $R^3$ to $R^7$ each correspond to one line of Table A.

Table 27: Compounds 27.1–27.514

Compounds of the formula Ib, where $R^1$ is chlorine, $R^2$ is trifluoromethyl, $R^{11}$, $R^{12}$, $R^{13}$, $R^{15}$ and $R^{16}$ are each hydrogen, $R^{14}$ is methyl and where for each individual compound the substituents $R^3$ to $R^7$ each correspond to one line of Table A.

Table 28: Compounds 28.1–28.514

Compounds of the formula Ib, where $R^1$ is methyl, $R^2$ is chlorine, $R^{11}$, $R^{12}$, $R^{13}$, $R^{15}$ and $R^{16}$ are each hydrogen, $R^{14}$ is methyl and where for each individual compound the substituents $R^3$ to $R^7$ each correspond to one line of Table A.

Table 29: Compounds 29.1–29.514

Compounds of the formula Ib, where $R^1$ is methyl, $R^2$ is methylsulfonyl, $R^{11}$, $R^{12}$, $R^{13}$, $R^{15}$ and $R^{16}$ are each hydrogen, $R^{14}$ is methyl and where for each individual compound the substituents $R^3$ to $R^7$ each correspond to one line of Table A.

Table 30: Compounds 30.1–30.514

Compounds of the formula Ib, where $R^1$ is methyl, $R^2$ is trifluoromethyl, $R^{11}$, $R^{12}$, $R^{13}$, $R^{15}$ and $R^{16}$ are each hydrogen, $R^{14}$ is methyl and where for each individual compound the substituents $R^3$ to $R^7$ each correspond to one line of Table A.

Table 31: Compounds 31.1–31.514

Compounds of the formula Ib, where $R^1$ is chlorine, $R^2$ is methylsulfonyl, $R^{11}$, $R^{12}$, $R^{14}$ and $R^{15}$ are each hydrogen, $R^{13}$ and $R^{16}$ together form a methylene group and where for each individual compound the substituents $R^3$ to $R^7$ each correspond to one line of Table A.

Table 32: Compounds 32.1–32.514

Compounds of the formula Ib, where $R^1$ and $R^2$ are each chlorine, $R^{11}$, $R^{12}$, $R^{14}$ and $R^{15}$ are each hydrogen, $R^{13}$ and $R^{16}$ together form a methylene group and where for each individual compound the substituents $R^3$ to $R^7$ each correspond to one line of Table A.

Table 33: Compounds 33.1–33.514

Compounds of the formula Ib, where $R^1$ is chlorine, $R^2$ is trifluoromethyl, $R^{11}$, $R^{12}$, $R^{14}$ and $R^{15}$ are each hydrogen, $R^{13}$ and $R^{16}$ together form a methylene group and where for each individual compound the substituents $R^3$ to $R^7$ each correspond to one line of Table A.

Table 34: Compounds 34.1–34.514

Compounds of the formula Ib, where $R^1$ is methyl, $R^2$ is chlorine, $R^{11}$, $R^{12}$, $R^{14}$ and $R^{15}$ are each hydrogen, $R^{13}$ and $R^{16}$ together form a methylene group and where for each individual compound the substituents $R^3$ to $R^7$ each correspond to one line of Table A.

Table 35: Compounds 35.1–35.514

Compounds of the formula Ib, where $R^1$ is methyl, $R^2$ is methylsulfonyl, $R^{11}$, $R^{12}$, $R^{14}$ and $R^{15}$ are each hydrogen, $R^{13}$ and $R^{16}$ together form a methylene group and where for each individual compound the substituents $R^3$ to $R^7$ each correspond to one line of Table A.

Table 36: Compounds 36.1–36.514

Compounds of the formula Ib, where $R^1$ is methyl, $R^2$ is trifluoromethyl, $R^{11}$, $R^{12}$, $R^{14}$ and $R^{15}$ are each hydrogen, $R^{13}$ and $R^{16}$ together form a methylene group and where for each individual compound the substituents $R^3$ to $R^7$ each correspond to one line of Table A.

TABLE B

| No. | $R^3$ | $R^4$ | $R^5$ |
|---|---|---|---|
| 1 | H | OH | H |
| 2 | H | OH | —CH$_3$ |
| 3 | H | OH | —C$_2$H$_5$ |
| 4 | H | OH | —C$_3$H$_7$ |
| 5 | H | OH | —C$_4$H$_9$ |
| 6 | H | OH | —CH=CH$_2$ |
| 7 | H | OH | —CH$_2$CH=CH$_2$ |
| 8 | H | OH | —CH$_2$CH=CHPh |
| 9 | H | OH | —CH$_2$CH=CHCH$_3$ |
| 10 | H | OH | —C≡CH |
| 11 | H | OH | —C≡CCH$_3$ |
| 12 | H | OH | —C≡CPh |
| 13 | H | OH | Ph |
| 14 | H | OH | —CH$_2$Ph |
| 15 | H | OH | cyclopropyl |
| 16 | H | OH | cyclobutyl |
| 17 | H | OH | cyclopentyl |
| 18 | H | OH | cyclohexyl |
| 19 | H | OH | OH |
| 20 | H | OH | —OCH$_3$ |

TABLE B-continued

| No. | R³ | R⁴ | R⁵ |
|---|---|---|---|
| 21 | H | OH | —OC₂H₅ |
| 22 | H | OH | —OC₃H₇ |
| 23 | H | OH | —OC₄H₉ |
| 24 | H | OH | —OCH₂CH=CH₂ |
| 25 | H | OH | —OPh |
| 26 | H | OH | —OCH₂Ph |
| 27 | H | OH | —Ocyclopropyl |
| 28 | H | OH | —Ocyclobutyl |
| 29 | H | OH | —Ocyclopentyl |
| 30 | H | OH | —Ocyclohexyl |
| 31 | H | OH | SH |
| 32 | H | OH | —SCH₃ |
| 33 | H | OH | —SC₂H₅ |
| 34 | H | OH | —SC₃H₇ |
| 35 | H | OH | —SC₄H₉ |
| 36 | H | OH | —SCH₂CH=CH₂ |
| 37 | H | OH | —SPh |
| 38 | H | OH | —SCH₂Ph |
| 39 | H | OH | —Scyclopropyl |
| 40 | H | OH | —Scyclobutyl |
| 41 | H | OH | —Scyclopentyl |
| 42 | H | OH | —Scyclohexyl |
| 43 | H | OH | NH₂ |
| 44 | H | OH | —NHCH₃ |
| 45 | H | OH | —NHC₂H₅ |
| 46 | H | OH | —NHC₃H₇ |
| 47 | H | OH | —NHC₄H₉ |
| 48 | H | OH | —NHCH₂CH=CH₂ |
| 49 | H | OH | —NHPh |
| 50 | H | OH | —NHCH₂Ph |
| 51 | H | OH | —NHcyclopropyl |
| 52 | H | OH | —NHcyclobutyl |
| 53 | H | OH | —NHcyclopentyl |
| 54 | H | OH | —NHcyclohexyl |
| 55 | H | OH | —N(CH₃)₂ |
| 56 | H | OH | —N(CH₃)(C₂H₅) |
| 57 | H | OH | —N(C₂H₅)₂ |
| 58 | H | OH | —N(CH₃)(C₃H₇) |
| 59 | H | OH | —N(CH₃)C₄H₉ |
| 60 | H | OH | —N(CH₃)(CH₂CH=CH₂) |
| 61 | H | OH | —N(CH₃)Ph |
| 62 | H | OH | —N(C₂H₅)Ph |
| 63 | H | OH | —N(Ph)₂ |
| 64 | H | OH | —N(C₂H₅)(CH₂Ph) |
| 65 | H | OH | —N(CH₂Ph)₂ |
| 66 | H | OH | —N(CH₃)(CH₂Ph) |
| 67 | H | OH | —N(CH₃)cyclopropyl |
| 68 | H | OH | —N(CH₃)cyclobutyl |
| 69 | H | OH | —N(CH₃)cyclopentyl |
| 70 | H | OH | —N(CH₃)cyclohexyl |
| 71 | H | —OSi(CH₃)₃ | H |
| 72 | H | —OSi(CH₃)₃ | —CH₃ |
| 73 | H | —OSi(CH₃)₃ | —C₂H₅ |
| 74 | H | —OSi(CH₃)₃ | —C₃H₇ |
| 75 | H | —OSi(CH₃)₃ | —C₄H₉ |
| 76 | H | —OSi(CH₃)₃ | —CH=CH₂ |
| 77 | H | —OSi(CH₃)₃ | —CH₂CH=CH₂ |
| 78 | H | —OSi(CH₃)₃ | —CH₂CH=CHPh |
| 79 | H | —OSi(CH₃)₃ | —CH₂CH=CHCH₃ |
| 80 | H | —OSi(CH₃)₃ | —C≡CH |
| 81 | H | —OSi(CH₃)₃ | —C≡CCH₃ |
| 82 | H | —OSi(CH₃)₃ | —C≡CPh |
| 83 | H | —OSi(CH₃)₃ | Ph |
| 84 | H | —OSi(CH₃)₃ | —CH₂Ph |
| 85 | H | —OSi(CH₃)₃ | cyclopropyl |
| 86 | H | —OSi(CH₃)₃ | cyclobutyl |
| 87 | H | —OSi(CH₃)₃ | cyclopentyl |
| 88 | H | —OSi(CH₃)₃ | cyclohexyl |
| 89 | H | —OSi(CH₃)₃ | OH |
| 90 | H | —OSi(CH₃)₃ | —OCH₃ |
| 91 | H | —OSi(CH₃)₃ | —OC₂H₅ |
| 92 | H | —OSi(CH₃)₃ | —OC₃H₇ |
| 93 | H | —OSi(CH₃)₃ | —OC₄H₉ |
| 94 | H | —OSi(CH₃)₃ | —OCH₂CH=CH₂ |
| 95 | H | —OSi(CH₃)₃ | —OPh |
| 96 | H | —OSi(CH₃)₃ | —OCH₂Ph |
| 97 | H | —OSi(CH₃)₃ | —Ocyclopropyl |
| 98 | H | —OSi(CH₃)₃ | —Ocyclobutyl |
| 99 | H | —OSi(CH₃)₃ | —Ocyclopentyl |
| 100 | H | —OSi(CH₃)₃ | —Ocyclohexyl |
| 101 | H | —OSi(CH₃)₃ | SH |
| 102 | H | —OSi(CH₃)₃ | —SCH₃ |
| 103 | H | —OSi(CH₃)₃ | —SC₂H₅ |
| 104 | H | —OSi(CH₃)₃ | —SC₃H₇ |
| 105 | H | —OSi(CH₃)₃ | —SC₄H₉ |
| 106 | H | —OSi(CH₃)₃ | —SCH₂CH=CH₂ |
| 107 | H | —OSi(CH₃)₃ | —SPh |
| 108 | H | —OSi(CH₃)₃ | —SCH₂Ph |
| 109 | H | —OSi(CH₃)₃ | —Scyclopropyl |
| 110 | H | —OSi(CH₃)₃ | —Scyclobutyl |
| 111 | H | —OSi(CH₃)₃ | —Scyclopentyl |
| 112 | H | —OSi(CH₃)₃ | —Scyclohexyl |
| 113 | H | —OSi(CH₃)₃ | NH₂ |
| 114 | H | —OSi(CH₃)₃ | —NHCH₃ |
| 115 | H | —OSi(CH₃)₃ | —NHC₂H₅ |
| 116 | H | —OSi(CH₃)₃ | —NHC₃H₇ |
| 117 | H | —OSi(CH₃)₃ | —NHC₄H₉ |
| 118 | H | —OSi(CH₃)₃ | —NHCH₂CH=CH₂ |
| 119 | H | —OSi(CH₃)₃ | —NHPh |
| 120 | H | —OSi(CH₃)₃ | —NHCH₂Ph |
| 121 | H | —OSi(CH₃)₃ | —NHcyclopropyl |
| 122 | H | —OSi(CH₃)₃ | —NHcyclobutyl |
| 123 | H | —OSi(CH₃)₃ | —NHcyclopentyl |
| 124 | H | —OSi(CH₃)₃ | —NHcyclohexyl |
| 125 | H | —OSi(CH₃)₃ | —N(CH₃)₂ |
| 126 | H | —OSi(CH₃)₃ | —N(CH₃)(C₂H₅) |
| 127 | H | —OSi(CH₃)₃ | —N(C₂H₅)₂ |
| 128 | H | —OSi(CH₃)₃ | —N(CH₃)(C₃H₇) |
| 129 | H | —OSi(CH₃)₃ | —N(CH₃)C₄H₉ |
| 130 | H | —OSi(CH₃)₃ | —N(CH₃)(CH₂CH=CH₂) |
| 131 | H | —OSi(CH₃)₃ | —N(CH₃)Ph |
| 132 | H | —OSi(CH₃)₃ | —N(C₂H₅)Ph |
| 133 | H | —OSi(CH₃)₃ | —N(Ph)₂ |
| 134 | H | —OSi(CH₃)₃ | —N(C₂H₅)(CH₂Ph) |
| 135 | H | —OSi(CH₃)₃ | —N(CH₂Ph)₂ |
| 136 | H | —OSi(CH₃)₃ | —N(CH₃)(CH₂Ph) |
| 137 | H | —OSi(CH₃)₃ | —N(CH₃)cyclopropyl |
| 138 | H | —OSi(CH₃)₃ | —N(CH₃)cyclobutyl |
| 139 | H | —OSi(CH₃)₃ | —N(CH₃)cyclopentyl |
| 140 | H | —OSi(CH₃)₃ | —N(CH₃)cyclohexyl |
| 141 | H | —OCH₃ | H |
| 142 | H | —OCH₃ | —CH₃ |
| 143 | H | —OCH₃ | —C₂H₅ |
| 144 | H | —OCH₃ | —C₃H₇ |
| 145 | H | —OCH₃ | —C₄H₉ |
| 146 | H | —OCH₃ | —CH=CH₂ |
| 147 | H | —OCH₃ | —CH₂CH=CH₂ |
| 148 | H | —OCH₃ | —CH₂CH=CHPh |
| 149 | H | —OCH₃ | —CH₂CH=CHCH₃ |
| 150 | H | —OCH₃ | —C≡CH |
| 151 | H | —OCH₃ | —C≡CCH₃ |
| 152 | H | —OCH₃ | —C≡CPh |
| 153 | H | —OCH₃ | Ph |
| 154 | H | —OCH₃ | —CH₂Ph |
| 155 | H | —OCH₃ | cyclopropyl |
| 156 | H | —OCH₃ | cyclobutyl |
| 157 | H | —OCH₃ | cyclopentyl |
| 158 | H | —OCH₃ | cyclohexyl |
| 159 | H | —OCH₃ | OH |
| 160 | H | —OCH₃ | —OCH₃ |
| 161 | H | —OCH₃ | —OC₂H₅ |
| 162 | H | —OCH₃ | —OC₃H₇ |
| 163 | H | —OCH₃ | —OC₄H₉ |
| 164 | H | —OCH₃ | —OCH₂CH=CH₂ |
| 165 | H | —OCH₃ | —OPh |
| 166 | H | —OCH₃ | —OCH₂Ph |
| 167 | H | —OCH₃ | —Ocyclopropyl |
| 168 | H | —OCH₃ | —Ocyclobutyl |
| 169 | H | —OCH₃ | —Ocyclopentyl |
| 170 | H | —OCH₃ | —Ocyclohexyl |
| 171 | H | —OCH₃ | SH |
| 172 | H | —OCH₃ | —SCH₃ |
| 173 | H | —OCH₃ | —SC₂H₅ |
| 174 | H | —OCH₃ | —SC₃H₇ |

TABLE B-continued

| No. | R³ | R⁴ | R⁵ |
|---|---|---|---|
| 175 | H | —OCH₃ | —SC₄H₉ |
| 176 | H | —OCH₃ | —SCH₂CH=CH₂ |
| 177 | H | —OCH₃ | —SPh |
| 178 | H | —OCH₃ | —SCH₂Ph |
| 179 | H | —OCH₃ | —Scyclopropyl |
| 180 | H | —OCH₃ | —Scyclobutyl |
| 181 | H | —OCH₃ | —Scyclopentyl |
| 182 | H | —OCH₃ | —Scyclohexyl |
| 183 | H | —OCH₃ | NH₂ |
| 184 | H | —OCH₃ | —NHCH₃ |
| 185 | H | —OCH₃ | —NHC₂H₅ |
| 186 | H | —OCH₃ | —NHC₃H₇ |
| 187 | H | —OCH₃ | —NHC₄H₉ |
| 188 | H | —OCH₃ | —NHCH₂CH=CH₂ |
| 189 | H | —OCH₃ | —NHPh |
| 190 | H | —OCH₃ | —NHCH₂Ph |
| 191 | H | —OCH₃ | —NHcyclopropyl |
| 192 | H | —OCH₃ | —NHcyclobutyl |
| 193 | H | —OCH₃ | —NHcyclopentyl |
| 194 | H | —OCH₃ | —NHcyclohexyl |
| 195 | H | —OCH₃ | —N(CH₃)₂ |
| 196 | H | —OCH₃ | —N(CH₃)(C₂H₅) |
| 197 | H | —OCH₃ | —N(C₂H₅)₂ |
| 198 | H | —OCH₃ | —N(CH₃)(C₃H₇) |
| 199 | H | —OCH₃ | —N(CH₃)C₄H₉ |
| 200 | H | —OCH₃ | —N(CH₃)(CH₂CH=CH₂) |
| 201 | H | —OCH₃ | —N(CH₃)Ph |
| 202 | H | —OCH₃ | —N(C₂H₅)Ph |
| 203 | H | —OCH₃ | —N(Ph)₂ |
| 204 | H | —OCH₃ | —N(C₂H₅)(CH₂Ph) |
| 205 | H | —OCH₃ | —N(CH₂Ph)₂ |
| 206 | H | —OCH₃ | —N(CH₃)(CH₂Ph) |
| 207 | H | —OCH₃ | —N(CH₃)cyclopropyl |
| 208 | H | —OCH₃ | —N(CH₃)cyclobutyl |
| 209 | H | —OCH₃ | —N(CH₃)cyclopentyl |
| 210 | H | —OCH₃ | —N(CH₃)cyclohexyl |
| 211 | H | —OSO₂CH₃ | H |
| 212 | H | —OSO₂CH₃ | —CH₃ |
| 213 | H | —OSO₂CH₃ | —C₂H₅ |
| 214 | H | —OSO₂CH₃ | —C₃H₇ |
| 215 | H | —OSO₂CH₃ | —C₄H₉ |
| 216 | H | —OSO₂CH₃ | —CH=CH₂ |
| 217 | H | —OSO₂CH₃ | —CH₂CH=CH₂ |
| 218 | H | —OSO₂CH₃ | —CH₂CH=CHPh |
| 219 | H | —OSO₂CH₃ | —CH₂CH=CHCH₃ |
| 220 | H | —OSO₂CH₃ | —C≡CH |
| 221 | H | —OSO₂CH₃ | —C≡CCH₃ |
| 222 | H | —OSO₂CH₃ | —C≡CPh |
| 223 | H | —OSO₂CH₃ | Ph |
| 224 | H | —OSO₂CH₃ | —CH₂Ph |
| 225 | H | —OSO₂CH₃ | cyclopropyl |
| 226 | H | —OSO₂CH₃ | cyclobutyl |
| 227 | H | —OSO₂CH₃ | cyclopentyl |
| 228 | H | —OSO₂CH₃ | cyclohexyl |
| 229 | H | —OSO₂CH₃ | OH |
| 230 | H | —OSO₂CH₃ | —OCH₃ |
| 231 | H | —OSO₂CH₃ | —OC₂H₅ |
| 232 | H | —OSO₂CH₃ | —OC₃H₇ |
| 233 | H | —OSO₂CH₃ | —OC₄H₉ |
| 234 | H | —OSO₂CH₃ | —OCH₂CH=CH₂ |
| 235 | H | —OSO₂CH₃ | —OPh |
| 236 | H | —OSO₂CH₃ | —OCH₂Ph |
| 237 | H | —OSO₂CH₃ | —Ocyclopropyl |
| 238 | H | —OSO₂CH₃ | —Ocyclobutyl |
| 239 | H | —OSO₂CH₃ | —Ocyclopentyl |
| 240 | H | —OSO₂CH₃ | —Ocyclohexyl |
| 241 | H | —OSO₂CH₃ | SH |
| 242 | H | —OSO₂CH₃ | —SCH₃ |
| 243 | H | —OSO₂CH₃ | —SC₂H₅ |
| 244 | H | —OSO₂CH₃ | —SC₃H₇ |
| 245 | H | —OSO₂CH₃ | —SC₄H₉ |
| 246 | H | —OSO₂CH₃ | —SCH₂CH=CH₂ |
| 247 | H | —OSO₂CH₃ | —SPh |
| 248 | H | —OSO₂CH₃ | —SCH₂Ph |
| 249 | H | —OSO₂CH₃ | —Scyclopropyl |
| 250 | H | —OSO₂CH₃ | —Scyclobutyl |
| 251 | H | —OSO₂CH₃ | —Scyclopentyl |
| 252 | H | —OSO₂CH₃ | —Scyclohexyl |
| 253 | H | —OSO₂CH₃ | NH₂ |
| 254 | H | —OSO₂CH₃ | —NHCH₃ |
| 255 | H | —OSO₂CH₃ | —NHC₂H₅ |
| 256 | H | —OSO₂CH₃ | —NHC₃H₇ |
| 257 | H | —OSO₂CH₃ | —NHC₄H₉ |
| 258 | H | —OSO₂CH₃ | —NHCH₂CH=CH₂ |
| 259 | H | —OSO₂CH₃ | —NHPh |
| 260 | H | —OSO₂CH₃ | —NHCH₂Ph |
| 261 | H | —OSO₂CH₃ | —NHcyclopropyl |
| 262 | H | —OSO₂CH₃ | —NHcyclobutyl |
| 263 | H | —OSO₂CH₃ | —NHcyclopentyl |
| 264 | H | —OSO₂CH₃ | —NHcyclohexyl |
| 265 | H | —OSO₂CH₃ | —N(CH₃)₂ |
| 266 | H | —OSO₂CH₃ | —N(CH₃)(C₂H₅) |
| 267 | H | —OSO₂CH₃ | —N(C₂H₅)₂ |
| 268 | H | —OSO₂CH₃ | —N(CH₃)(C₃H₇) |
| 269 | H | —OSO₂CH₃ | —N(CH₃)C₄H₉ |
| 270 | H | —OSO₂CH₃ | —N(CH₃)(CH₂CH=CH₂) |
| 271 | H | —OSO₂CH₃ | —N(CH₃)Ph |
| 272 | H | —OSO₂CH₃ | —N(C₂H₅)Ph |
| 273 | H | —OSO₂CH₃ | —N(Ph)₂ |
| 274 | H | —OSO₂CH₃ | —N(C₂H₅)(CH₂Ph) |
| 275 | H | —OSO₂CH₃ | —N(CH₂Ph)₂ |
| 276 | H | —OSO₂CH₃ | —N(CH₃)(CH₂Ph) |
| 277 | H | —OSO₂CH₃ | —N(CH₃)cyclopropyl |
| 278 | H | —OSO₂CH₃ | —N(CH₃)cyclobutyl |
| 279 | H | —OSO₂CH₃ | —N(CH₃)cyclopentyl |
| 280 | H | —OSO₂CH₃ | —N(CH₃)cyclohexyl |
| 281 | —CH₃ | OH | H |
| 282 | —CH₃ | OH | —CH₃ |
| 283 | —CH₃ | OH | —C₂H₅ |
| 284 | —CH₃ | OH | —C₃H₇ |
| 285 | —CH₃ | OH | —C₄H₉ |
| 286 | —CH₃ | OH | —CH=CH₂ |
| 287 | —CH₃ | OH | —CH₂CH=CH₂ |
| 288 | —CH₃ | OH | —CH₂CH=CHPh |
| 289 | —CH₃ | OH | —CH₂CH=CHCH₃ |
| 290 | —CH₃ | OH | —C≡CH |
| 291 | —CH₃ | OH | —C≡CCH₃ |
| 292 | —CH₃ | OH | —C≡CPh |
| 293 | —CH₃ | OH | Ph |
| 294 | —CH₃ | OH | —CH₂Ph |
| 295 | —CH₃ | OH | cyclopropyl |
| 296 | —CH₃ | OH | cyclobutyl |
| 297 | —CH₃ | OH | cyclopentyl |
| 298 | —CH₃ | OH | cyclohexyl |
| 299 | —CH₃ | OH | OH |
| 300 | —CH₃ | OH | —OCH₃ |
| 301 | —CH₃ | OH | —OC₂H₅ |
| 302 | —CH₃ | OH | —OC₃H₇ |
| 303 | —CH₃ | OH | —OC₄H₉ |
| 304 | —CH₃ | OH | —OCH₂CH=CH₂ |
| 305 | —CH₃ | OH | —OPh |
| 306 | —CH₃ | OH | —OCH₂Ph |
| 307 | —CH₃ | OH | —Ocyclopropyl |
| 308 | —CH₃ | OH | —Ocyclobutyl |
| 309 | —CH₃ | OH | —Ocyclopentyl |
| 310 | —CH₃ | OH | —Ocyclohexyl |
| 311 | —CH₃ | OH | SH |
| 312 | —CH₃ | OH | —SCH₃ |
| 313 | —CH₃ | OH | —SC₂H₅ |
| 314 | —CH₃ | OH | —SC₃H₇ |
| 315 | —CH₃ | OH | —SC₄H₉ |
| 316 | —CH₃ | OH | —SCH₂CH=CH₂ |
| 317 | —CH₃ | OH | —SPh |
| 318 | —CH₃ | OH | —SCH₂Ph |
| 319 | —CH₃ | OH | —Scyclopropyl |
| 320 | —CH₃ | OH | —Scyclobutyl |
| 321 | —CH₃ | OH | —Scyclopentyl |
| 322 | —CH₃ | OH | —Scyclohexyl |
| 323 | —CH₃ | OH | NH₂ |
| 324 | —CH₃ | OH | —NHCH₃ |
| 325 | —CH₃ | OH | —NHC₂H₅ |
| 326 | —CH₃ | OH | —NHC₃H₇ |
| 327 | —CH₃ | OH | —NHC₄H₉ |
| 328 | —CH₃ | OH | —NHCH₂CH=CH₂ |

TABLE B-continued

| No. | R³ | R⁴ | R⁵ |
|---|---|---|---|
| 329 | —CH₃ | OH | —NHPh |
| 330 | —CH₃ | OH | —NHCH₂Ph |
| 331 | —CH₃ | OH | —NHcyclopropyl |
| 332 | —CH₃ | OH | —NHcyclobutyl |
| 333 | —CH₃ | OH | —NHcyclopentyl |
| 334 | —CH₃ | OH | —NHcyclohexyl |
| 335 | —CH₃ | OH | —N(CH₃)₂ |
| 336 | —CH₃ | OH | —N(CH₃)(C₂H₅) |
| 337 | —CH₃ | OH | —N(C₂H₅)₂ |
| 338 | —CH₃ | OH | —N(CH₃)(C₃H₇) |
| 339 | —CH₃ | OH | —N(CH₃)C₄H₉ |
| 340 | —CH₃ | OH | —N(CH₃)(CH₂CH=CH₂) |
| 341 | —CH₃ | OH | —N(CH₃)Ph |
| 342 | —CH₃ | OH | —N(C₂H₅)Ph |
| 343 | —CH₃ | OH | —N(Ph)₂ |
| 344 | —CH₃ | OH | —N(C₂H₅)(CH₂Ph) |
| 345 | —CH₃ | OH | —N(CH₂Ph)₂ |
| 346 | —CH₃ | OH | —N(CH₃)(CH₂Ph) |
| 347 | —CH₃ | OH | —N(CH₃)cyclopropyl |
| 348 | —CH₃ | OH | —N(CH₃)cyclobutyl |
| 349 | —CH₃ | OH | —N(CH₃)cyclopentyl |
| 350 | —CH₃ | OH | —N(CH₃)cyclohexyl |
| 351 | H | OH | H |
| 352 | H | OH | —CH₃ |
| 353 | H | OH | —C₂H₅ |
| 354 | H | OH | —C₃H₇ |
| 355 | H | OH | —C₄H₉ |
| 356 | H | OH | —CH=CH₂ |
| 357 | H | OH | —CH₂CH=CH₂ |
| 358 | H | OH | —CH₂CH=CHPh |
| 359 | H | OH | —CH₂CH=CHCH₃ |
| 360 | H | OH | —C≡CH |
| 361 | H | OH | —C≡CCH₃ |
| 362 | H | OH | —C≡CPh |
| 363 | H | OH | Ph |
| 364 | H | OH | —CH₂Ph |
| 365 | H | OH | cyclopropyl |
| 366 | H | OH | cyclobutyl |
| 367 | H | OH | cyclopentyl |
| 368 | H | OH | cyclohexyl |
| 369 | H | OH | OH |
| 370 | H | OH | —OCH₃ |
| 371 | H | OH | —OC₂H₅ |
| 372 | H | OH | —OC₃H₇ |
| 373 | H | OH | —OC₄H₉ |
| 374 | H | OH | —OCH₂CH=CH₂ |
| 375 | H | OH | —OPh |
| 376 | H | OH | —OCH₂Ph |
| 377 | H | OH | —Ocyclopropyl |
| 378 | H | OH | —Ocyclobutyl |
| 379 | H | OH | —Ocyclopentyl |
| 380 | H | OH | —Ocyclohexyl |
| 381 | H | OH | SH |
| 382 | H | OH | —SCH₃ |
| 383 | H | OH | —SC₂H₅ |
| 384 | H | OH | —SC₃H₇ |
| 385 | H | OH | —SC₄H₉ |
| 386 | H | OH | —SCH₂CH=CH₂ |
| 387 | H | OH | —SPh |
| 388 | H | OH | —SCH₂Ph |
| 389 | H | OH | —Scyclopropyl |
| 390 | H | OH | —Scyclobutyl |
| 391 | H | OH | —Scyclopentyl |
| 392 | H | OH | —Scyclohexyl |
| 393 | H | OH | NH₂ |
| 394 | H | OH | —NHCH₃ |
| 395 | H | OH | —NHC₂H₅ |
| 396 | H | OH | —NHC₃H₇ |
| 397 | H | OH | —NHC₄H₉ |
| 398 | H | OH | —NHCH₂CH=CH₂ |
| 399 | H | OH | —NHPh |
| 400 | H | OH | —NHCH₂Ph |
| 401 | H | OH | —NHcyclopropyl |
| 402 | H | OH | —NHcyclobutyl |
| 403 | H | OH | —NHcyclopentyl |
| 404 | H | OH | —NHcyclohexyl |
| 405 | H | OH | —N(CH₃)₂ |
| 406 | H | OH | —N(CH₃)(C₂H₅) |
| 407 | H | OH | —N(C₂H₅)₂ |
| 408 | H | OH | —N(CH₃)(C₃H₇) |
| 409 | H | OH | —N(CH₃)C₄H₉ |
| 410 | H | OH | —N(CH₃)(CH₂CH=CH₂) |
| 411 | H | OH | —N(CH₃)Ph |
| 412 | H | OH | —N(C₂H₅)Ph |
| 413 | H | OH | —N(Ph)₂ |
| 414 | H | OH | —N(C₂H₅)(CH₂Ph) |
| 415 | H | OH | —N(CH₂Ph)₂ |
| 416 | H | OH | —N(CH₃)(CH₂Ph) |
| 417 | H | OH | —N(CH₃)cyclopropyl |
| 418 | H | OH | —N(CH₃)cyclobutyl |
| 419 | H | OH | —N(CH₃)cyclopentyl |
| 420 | H | OH | —N(CH₃)cyclohexyl |
| 421 | H | OH | H |
| 422 | H | OH | —CH₃ |
| 423 | H | OH | —C₂H₅ |
| 424 | H | OH | —C₃H₇ |
| 425 | H | OH | —C₄H₉ |
| 426 | H | OH | —CH=CH₂ |
| 427 | H | OH | —CH₂CH=CH₂ |
| 428 | H | OH | —CH₂CH=CHPh |
| 429 | H | OH | —CH₂CH=CHCH₃ |
| 430 | H | OH | —C≡CH |
| 431 | H | OH | —C≡CCH₃ |
| 432 | H | OH | —C≡CPh |
| 433 | H | OH | Ph |
| 434 | H | OH | —CH₂Ph |
| 435 | H | OH | cyclopropyl |
| 436 | H | OH | cyclobutyl |
| 437 | H | OH | cyclopentyl |
| 438 | H | OH | cyclohexyl |
| 439 | H | OH | OH |
| 440 | H | OH | —OCH₃ |
| 441 | H | OH | —OC₂H₅ |
| 442 | H | OH | —OC₃H₇ |
| 443 | H | OH | —OC₄H₉ |
| 444 | H | OH | —OCH₂CH=CH₂ |
| 445 | H | OH | —OPh |
| 446 | H | OH | —OCH₂Ph |
| 447 | H | OH | —Ocyclopropyl |
| 448 | H | OH | —Ocyclobutyl |
| 449 | H | OH | —Ocyclopentyl |
| 450 | H | OH | —Ocyclohexyl |
| 451 | H | OH | SH |
| 452 | H | OH | —SCH₃ |
| 453 | H | OH | —SC₂H₅ |
| 454 | H | OH | —SC₃H₇ |
| 455 | H | OH | —SC₄H₉ |
| 456 | H | OH | —SCH₂CH=CH₂ |
| 457 | H | OH | —SPh |
| 458 | H | OH | —SCH₂Ph |
| 459 | H | OH | —Scyclopropyl |
| 460 | H | OH | —Scyclobutyl |
| 461 | H | OH | —Scyclopentyl |
| 462 | H | OH | —Scyclohexyl |
| 463 | H | OH | NH₂ |
| 464 | H | OH | —NHCH₃ |
| 465 | H | OH | —NHC₂H₅ |
| 466 | H | OH | —NHC₃H₇ |
| 467 | H | OH | —NHC₄H₉ |
| 468 | H | OH | —NHCH₂CH=CH₂ |
| 469 | H | OH | —NHPh |
| 470 | H | OH | —NHCH₂Ph |
| 471 | H | OH | —NHcyclopropyl |
| 472 | H | OH | —NHcyclobutyl |
| 473 | H | OH | —NHcyclopentyl |
| 474 | H | OH | —NHcyclohexyl |
| 475 | H | OH | —N(CH₃)₂ |
| 476 | H | OH | —N(CH₃)(C₂H₅) |
| 477 | H | OH | —N(C₂H₅)₂ |
| 478 | H | OH | —N(CH₃)(C₃H₇) |
| 479 | H | OH | —N(CH₃)C₄H₉ |
| 480 | H | OH | —N(CH₃)(CH₂CH=CH₂) |
| 481 | H | OH | —N(CH₃)Ph |
| 482 | H | OH | —N(C₂H₅)Ph |

TABLE B-continued

| No. | R³ | R⁴ | R⁵ |
|---|---|---|---|
| 483 | H | OH | —N(Ph)₂ |
| 484 | H | OH | —N(C₂H₅)(CH₂Ph) |
| 485 | H | OH | —N(CH₂Ph)₂ |
| 486 | H | OH | —N(CH₃)(CH₂Ph) |
| 487 | H | OH | —N(CH₃)cyclopropyl |
| 488 | H | OH | —N(CH₃)cyclobutyl |
| 489 | H | OH | —N(CH₃)cyclopentyl |
| 490 | H | OH | —N(CH₃)cyclohexyl |
| 491 | H | H | —OCH₂CH₂— |
| 492 | CH₃ | H | —OCH₂CH₂— |
| 493 | H | H | —CH₂CH₂O— |
| 494 | CH₃ | H | —CH₂CH₂O— |
| 495 | H | H | —OCH═CH— |
| 496 | CH₃ | H | —OCH═CH— |
| 497 | H | H | —CH═CHO— |
| 498 | CH₃ | H | —CH═CHO— |
| 499 | H | H | —OCH₂CH₂CH₂— |
| 500 | CH₃ | H | —OCH₂CH₂CH₂— |
| 501 | H | H | —CH₂CH₂CH₂O— |
| 502 | CH₃ | H | —CH₂CH₂CH₂O— |
| 503 | H | H | —NHCH₂CH₂— |
| 504 | CH₃ | H | —NHCH₂CH₂— |
| 505 | H | H | —CH₂CH₂NH— |
| 506 | CH₃ | H | —CH₂CH₂NH— |
| 507 | H | H | —NHCH═CH— |
| 508 | CH₃ | H | —NHCH═CH— |
| 509 | H | H | —CH═CHNH— |
| 510 | CH₃ | H | —CH═CHNH— |
| 511 | H | H | —NHCH₂CH₂CH₂— |
| 512 | CH₃ | H | —NHCH₂CH₂CH₂— |
| 513 | H | H | —CH₂CH₂CH₂NH— |
| 514 | CH₃ | H | —CH₂CH₂CH₂NH— |

The Tables 37 to 72 below are based on the 2-benzoylcyclohexane-1,3-diones of the formula Ic:

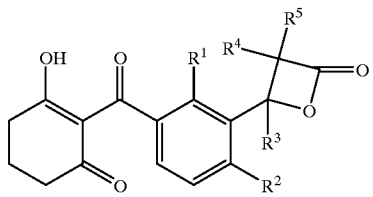

Table 37: Compounds 37.1–37.514

Compounds of the formula Ic, where $R^1$ is chlorine, $R^2$ is methylsulfonyl, $R^{11}$, $R^{12}$, $R^{13}$, $R^{14}$, $R^{15}$ and $R^{16}$ are each hydrogen and where for each individual compound the substituents $R^3$ to $R^7$ each correspond to one line of Table B.

Table 38: Compounds 38.1–38.514

Compounds of the formula Ic, where $R^1$ and $R^2$ are each chlorine, $R^{11}$, $R^{12}$, $R^{13}$, $R^{14}$, $R^{15}$ and $R^{16}$ are each hydrogen and where for each individual compound the substituents $R^3$ to $R^7$ each correspond to one line of Table B.

Table 39: Compounds 39.1–39.514

Compounds of the formula Ic, where $R^1$ is chlorine, $R^2$ is trifluoromethyl, $R^{11}$, $R^{12}$, $R^{13}$, $R^{14}$, $R^{15}$ and $R^{16}$ are each hydrogen and where for each individual compound the substituents $R^3$ to $R^7$ each correspond to one line of Table B.

Table 40: Compounds 40.1–40.514

Compounds of the formula Ic, where $R^1$ is methyl, $R^2$ is chlorine, $R^{11}$, $R^{12}$, $R^{13}$, $R^{14}$, $R^{15}$ and $R^{16}$ are each hydrogen and where for each individual compound the substituents $R^3$ to $R^7$ each correspond to one line of Table B.

Table 41: Compounds 41.1–41.514

Compounds of the formula Ic, where $R^1$ is methyl, $R^2$ is methylsulfonyl, $R^{11}$, $R^{12}$, $R^{13}$, $R^{14}$, $R^{15}$ and $R^{16}$ are each hydrogen and where for each individual compound the substituents $R^3$ to $R^7$ each correspond to one line of Table B.

Table 42: Compounds 42.1–42.514

Compounds of the formula Ic, where $R^1$ is methyl, $R^2$ is trifluoromethyl, $R^{11}$, $R^{12}$, $R^{13}$, $R^{14}$, $R^{15}$ and $R^{16}$ are each hydrogen and where for each individual compound the substituents $R^3$ to $R^7$ each correspond to one line of Table B.

Table 43: Compounds 43.1–43.514

Compounds of the formula Ic, where $R^1$ is chlorine, $R^2$ is methylsulfonyl, $R^{11}$, $R^{12}$, $R^{15}$ and $R^{16}$ are each hydrogen, $R^{13}$ and $R^{14}$ are each methyl and where for each individual compound the substituents $R^3$ to $R^7$ each correspond to one line of Table B.

Table 44: Compounds 44.1–44.514

Compounds of the formula Ic, where $R^1$ and $R^2$ are each chlorine, $R^{11}$, $R^{12}$, $R^{15}$ and $R^{16}$ are each hydrogen, $R^{13}$ and $R^{14}$ are each methyl and where for each individual compound the substituents $R^3$ to $R^7$ each correspond to one line of Table B.

Table 45: Compounds 45.1–45.514

Compounds of the formula Ic, where $R^1$ is chlorine, $R^2$ is trifluoromethyl, $R^{11}$, $R^{12}$, $R^{15}$ and $R^{16}$ are each hydrogen, $R^{13}$ and $R^{14}$ are each methyl and where for each individual compound the substituents $R^3$ to $R^7$ each correspond to one line of Table B.

Table 46: Compounds 46.1–46.514

Compounds of the formula Ic, where $R^1$ is methyl, $R^2$ is chlorine, $R^{11}$, $R^{12}$, $R^{15}$ and $R^{16}$ are each hydrogen, $R^{13}$ and $R^{14}$ are each methyl and where for each individual compound the substituents $R^3$ to $R^7$ each correspond to one line of Table B.

Table 47: Compounds 47.1–47.514

Compounds of the formula Ic, where $R^1$ is methyl, $R^2$ is methylsulfonyl, $R^{11}$, $R^{12}$, $R^{15}$ and $R^{16}$ are each hydrogen, $R^{13}$ and $R^{14}$ are each methyl and where for each individual compound the substituents $R^3$ to $R^7$ each correspond to one line of Table B.

Table 48: Compounds 48.1–48.514

Compounds of the formula Ic, where $R^1$ is methyl, $R^2$ is trifluoromethyl, $R^{11}$, $R^{12}$, $R^{15}$ and $R^{16}$ are each hydrogen, $R^{13}$ and $R^{14}$ are each methyl and where for each individual compound the substituents $R^3$ to $R^7$ each correspond to one line of Table B.

Table 49: Compounds 49.1–49.514

Compounds of the formula Ic, where $R^1$ is chlorine, $R^2$ is methylsulfonyl, $R^{11}$, $R^{12}$, $R^{13}$ and $R^{14}$ are each hydrogen, $R^{15}$ and $R^{16}$ are each methyl and where for each individual compound the substituents $R^3$ to $R^7$ each correspond to one line of Table B.

Table 50: Compounds 50.1–50.514

Compounds of the formula Ic, where $R^1$ and $R^2$ are each chlorine, $R^{11}$, $R^{12}$, $R^{13}$ and $R^{14}$ are each hydrogen, $R^{15}$ and $R^{16}$ are each methyl and where for each individual compound the substituents $R^3$ to $R^7$ each correspond to one line of Table B.

Table 51: Compounds 51.1–51.514

Compounds of the formula Ic, where $R^1$ is chlorine, $R^2$ is trifluoromethyl, $R^{11}$, $R^{12}$, $R^{13}$ and $R^{14}$ are each hydrogen, $R^{15}$ and $R^{16}$ are each methyl and where for each individual compound the substituents $R^3$ to $R^7$ each correspond to one line of Table B.

Table 52: Compounds 52.1–52.514

Compounds of the formula Ic, where $R^1$ is methyl, $R^2$ is chlorine, $R^{11}$, $R^{12}$, $R^{13}$ and $R^{14}$ are each hydrogen, $R^{15}$ and $R^{16}$ are each methyl and where for each individual compound the substituents $R^3$ to $R^7$ each correspond to one line of Table B.

Table 53: Compounds 53.1–53.514
Compounds of the formula Ic, where $R^1$ is methyl, $R^2$ is methylsulfonyl, $R^{11}$, $R^{12}$, $R^{13}$ and $R^{14}$ are each hydrogen, $R^{15}$ and $R^{16}$ are each methyl and where for each individual compound the substituents $R^3$ to $R^7$ each correspond to one line of Table B.

Table 54: Compounds 54.1–54.514
Compounds of the formula Ic, where $R^1$ is methyl, $R^2$ is trifluoromethyl, $R^{11}$, $R^{12}$, $R^{13}$ and $R^{14}$ are each hydrogen, $R^{15}$ and $R^{16}$ are each methyl and where for each individual compound the substituents $R^3$ to $R^7$ each correspond to one line of Table B.

Table 55: Compounds 55.1–55.514
Compounds of the formula Ic, where $R^1$ is chlorine, $R^2$ is methylsulfonyl, $R^{11}$, $R^{12}$, $R^{15}$ and $R^{16}$ are each methyl, the $CR^{13}R^{14}$ unit forms a group C=O and where for each individual compound the substituents $R^3$ to $R^7$ each correspond to one line of Table B.

Table 56: Compounds 56.1–56.514
Compounds of the formula Ic, where $R^1$ and $R^2$ are each chlorine, $R^{11}$, $R^{12}$, $R^{15}$ and $R^{16}$ are each methyl, the $CR^{13}R^{14}$ unit forms a group C=O and where for each individual compound the substituents $R^3$ to $R^7$ each correspond to one line of Table B.

Table 57: Compounds 57.1–57.514
Compounds of the formula Ic, where $R^1$ is chlorine, $R^2$ is trifluoromethyl, $R^{11}$, $R^{12}$, $R^{15}$ and $R^{16}$ are each methyl, the $CR^{13}R^{14}$ unit forms a group C=O and where for each individual compound the substituents $R^3$ to $R^7$ each correspond to one line of Table B.

Table 58: Compounds 58.1–58.514
Compounds of the formula Ic, where $R^1$ is methyl, $R^2$ is chlorine, $R^{11}$, $R^{12}$, $R^{15}$ and $R^{16}$ are each methyl, the $CR^{13}R^{14}$ unit forms a group C=O and where for each individual compound the substituents $R^3$ to $R^7$ each correspond to one line of Table B.

Table 59: Compounds 59.1–59.514
Compounds of the formula Ic, where $R^1$ is methyl, $R^2$ is methylsulfonyl, $R^{11}$, $R^{12}$, $R^{15}$ and $R^{16}$ are each methyl, the $CR^{13}R^{14}$ unit forms a group C=O and where for each individual compound the substituents $R^3$ to $R^7$ each correspond to one line of Table B.

Table 60: Compounds 60.1–60.514
Compounds of the formula Ic, where $R^1$ is methyl, $R^2$ is trifluoromethyl, $R^{11}$, $R^{12}$, $R^{15}$ and $R^{16}$ are each methyl, the $CR^{13}R^{14}$ unit forms a group C=O and where for each individual compound the substituents $R^3$ to $R^7$ each correspond to one line of Table B.

Table 61: Compounds 61.1–61.514
Compounds of the formula Ic, where $R^1$ is methylsulfonyl, $R^{11}$, $R^{12}$, $R^{13}$, $R^{15}$ and $R^{16}$ are each hydrogen, $R^{14}$ is methyl and where for each individual compound the substituents $R^3$ to $R^7$ each correspond to one line of Table B.

Table 62: Compounds 62.1–62.514
Compounds of the formula Ic, where $R^1$ and $R^2$ are each chlorine, $R^{11}$, $R^{12}$, $R^{13}$, $R^{15}$ and $R^{16}$ are each hydrogen, $R^{14}$ is methyl and where for each individual compound the substituents $R^3$ to $R^7$ each correspond to one line of Table B.

Table 63: Compounds 63.1–63.514
Compounds of the formula Ic, where $R^1$ is chlorine, $R^2$ is trifluoromethyl, $R^{11}$, $R^{12}$, $R^{13}$, $R^{15}$ and $R^{16}$ are each hydrogen, $R^{14}$ is methyl and where for each individual compound the substituents $R^3$ to $R^7$ each correspond to one line of Table B.

Table 64: Compounds 64.1–64.514
Compounds of the formula Ic, where $R^1$ is methyl, $R^2$ is chlorine, $R^{11}$, $R^{12}$, $R^{13}$, $R^{15}$ and $R^{16}$ are each hydrogen, $R^{14}$ is methyl and where for each individual compound the substituents $R^3$ to $R^7$ each correspond to one line of Table B.

Table 65: Compounds 65.1–65.514
Compounds of the formula Ic, where $R^1$ is methyl, $R^2$ is methylsulfonyl, $R^{11}$, $R^{12}$, $R^{13}$, $R^{15}$ and $R^{16}$ are each hydrogen, $R^{14}$ is methyl and where for each individual compound the substituents $R^3$ to $R^7$ each correspond to one line of Table B.

Table 66: Compounds 66.1–66.514
Compounds of the formula Ic, where $R^1$ is methyl, $R^2$ is trifluoromethyl, $R^{11}$, $R^{12}$, $R^{13}$, $R^{15}$ and $R^{16}$ are each hydrogen, $R^{14}$ is methyl and where for each individual compound the substituents $R^3$ to $R^7$ each correspond to one line of Table B.

Table 67: Compounds 67.1–67.514
Compounds of the formula Ic, where $R^1$ is chlorine, $R^2$ is methylsulfonyl, $R^{11}$, $R^{12}$, $R^{14}$ and $R^{15}$ are each hydrogen, $R^{13}$ and $R^{16}$ together form a methylene group and where for each individual compound the substituents $R^3$ to $R^7$ each correspond to one line of Table B.

Table 68: Compounds 68.1–68.514
Compounds of the formula Ic, where $R^1$ and $R^2$ are each chlorine, $R^{11}$, $R^{12}$, $R^{14}$ and $R^{15}$ are each hydrogen, $R^{13}$ and $R^{16}$ together form a methylene group and where for each individual compound the substituents $R^3$ to $R^7$ each correspond to one line of Table B.

Table 69: Compounds 69.1–69.514
Compounds of the formula Ic, where $R^1$ is chlorine, $R^2$ is trifluoromethyl, $R^{11}$, $R^{12}$, $R^{14}$ and $R^{15}$ are each hydrogen, $R^{13}$ and $R^{16}$ together form a methylene group and where for each individual compound the substituents $R^3$ to $R^7$ each correspond to one line of Table B.

Table 70: Compounds 70.1–70.514
Compounds of the formula Ic, where $R^1$ is methyl, $R^2$ is chlorine, $R^{11}$, $R^{12}$, $R^{14}$ and $R^{15}$ are each hydrogen, $R^{13}$ and $R^{16}$ together form a methylene group and where for each individual compound the substituents $R^3$ to $R^7$ each correspond to one line of Table B.

Table 71: Compounds 71.1–71.514
Compounds of the formula Ic, where $R^1$ is methyl, $R^2$ is methylsulfonyl, $R^{11}$, $R^{12}$, $R^{14}$ and $R^{15}$ are each hydrogen, $R^{13}$ and $R^{16}$ together form a methylene group and where for each individual compound the substituents $R^3$ to $R^7$ each correspond to one line of Table B.

Table 72: Compounds 72.1–72.514
Compounds of the formula Ic, where $R^1$ is methyl, $R^2$ is trifluoromethyl, $R^{11}$, $R^{12}$, $R^{14}$ and $R^{15}$ are each hydrogen, $R^{13}$ and $R^{16}$ together form a methylene group and where for each individual compound the substituents $R^3$ to $R^7$ each correspond to one line of Table B.

TABLE C

| No. | $R^3$ | $R^8$ | $R^9$ |
|---|---|---|---|
| 1 | H | H | H |
| 2 | H | $CH_3$ | H |
| 3 | H | $C_2H_5$ | H |
| 4 | H | $C_3H_7$ | H |
| 5 | H | $C_4H_9$ | H |
| 6 | H | $CH(CH_3)_2$ | H |
| 7 | H | cy-$C_3H_5$ | H |
| 8 | H | cy-$C_4H_7$ | H |
| 9 | H | cy-$C_5H_9$ | H |
| 10 | H | cy-$C_6$-$H_{11}$ | H |
| 11 | H | $C_6H_5$ | H |
| 12 | H | $CH_2$-$C_6H_5$ | H |
| 13 | H | 2-furyl | H |
| 14 | H | 3-furyl | H |

TABLE C-continued

| No. | R³ | R⁸ | R⁹ |
|---|---|---|---|
| 15 | H | 2-thienyl | H |
| 16 | H | 3-thienyl | H |
| 17 | H | 2-dioxanyl | H |
| 18 | H | CHO | H |
| 19 | H | COCH₃ | H |
| 20 | H | COOCH₃ | H |
| 21 | H | COOC₂H₅ | H |
| 22 | H | OCH₃ | H |
| 23 | H | CN | H |
| 24 | H | SCH₃ | H |
| 25 | H | COCF₃ | H |
| 26 | H | COC₆H₅ | H |
| 27 | H | CH=NOCH₃ | H |
| 28 | H | CH=NOC₂H₅ | H |
| 29 | H | C(CH₃)=NOCH₃ | H |
| 30 | H | CH₃ | CH₃ |
| 31 | H | C₂H₅ | CH₃ |
| 32 | H | C₃H₇ | CH₃ |
| 33 | H | C₄H₉ | CH₃ |
| 34 | H | CHO | CH₃ |
| 35 | H | COCH₃ | CH₃ |
| 36 | H | COOCH₃ | CH₃ |
| 37 | H | OCH₃ | CH₃ |
| 38 | H | C₆H₅ | CH₃ |
| 39 | H | CH₂-CHO | H |
| 40 | H | COOCH₂C₆H₅ | H |
| 41 | Cl | CH₃ | H |
| 42 | CH₃ | CH₃ | H |
| 43 | C₂H₅ | CH₃ | H |
| 44 | CF₃ | CH₃ | H |
| 45 | OCH₃ | CH₃ | H |
| 46 | OC₂H₅ | CH₃ | H |
| 47 | CH₂-C≡CH | CH₃ | H |
| 48 | CH₂-CH=CH₂ | CH₃ | H |
| 49 | Cl | CH₃ | H |
| 50 | CH₃ | CH₃ | H |
| 51 | CF₃ | CH₃ | H |
| 52 | OCH₃ | CH₃ | H |
| 53 | OC₂H₅ | CH₃ | H |
| 54 | CH₂-CH=CH₂ | CH₃ | H |
| 55 | CH₂-C≡CH | CH₃ | H |
| 56 | H | CH₃ | Ph |
| 57 | H | C₂H₅ | Ph |
| 58 | H | C₃H₇ | Ph |
| 59 | H | C₄H₉ | Ph |
| 60 | H | CHO | Ph |
| 61 | H | COCH₃ | Ph |
| 62 | H | COOCH₃ | Ph |
| 63 | H | OCH₃ | Ph |
| 64 | H | C₆H₅ | Ph |
| 65 | H | CH=NOCH₃ | Ph |
| 66 | H | C(CH₃)=NOCH₃ | Ph |
| 67 | CH₃ | 2-Cl-C₆H₄ | H |
| 68 | CH₃ | 3-Br-C₆H₄ | H |
| 69 | CH₃ | 4-F-C₆H₄ | H |
| 70 | CH₃ | 2,4-Cl₂-C₆H₃ | H |
| 71 | CH₃ | 2-NO₂-C₆H₄ | H |
| 72 | CH₃ | 3-CN-C₆H₄ | H |
| 73 | CH₃ | 4-Me-C₆H₄ | H |
| 74 | CH₃ | 2-OMe-C₆H₄ | H |
| 75 | CH₃ | 3-CF₃-C₆H₄ | H |
| 76 | CH₃ | 4-OCF₃-C₆H₄ | H |
| 77 | CH₃ | 2-Me-C₆H₄ | H |
| 78 | CH₃ | 3-Me-C₆H₄ | H |
| 79 | CH₃ | 2-SMe-C₆H₄ | H |
| 80 | CH₃ | 3-COOMe-C₆H₄ | H |
| 81 | CH₃ | 4-CF₃-C₆H₄ | H |
| 82 | CH₃ | 2-CF₃-C₆H₄ | H |
| 83 | CH₃ | 3-OMe-C₆H₄ | H |
| 84 | CH₃ | 4-OMe-C₆H₄ | H |
| 85 | H | 2-furyl | CH₃ |
| 86 | H | 3-furyl | CH₃ |
| 87 | H | 2-thienyl | CH₃ |
| 88 | H | 3-thienyl | CH₃ |
| 89 | H | 2-pyridyl | CH₃ |
| 90 | H | 3-pyridyl | CH₃ |
| 91 | H | 4-pyridyl | CH₃ |
| 92 | H | 2-thiazolyl | CH₃ |
| 93 | H | 4-thiazolyl | CH₃ |
| 94 | H | 5-thiazolyl | CH₃ |
| 95 | H | 2-pyrrolyl | CH₃ |
| 96 | H | 3-pyrrolyl | CH₃ |
| 97 | H | 4-pyrrolyl | CH₃ |
| 98 | H | 3-isoxazolyl | CH₃ |
| 99 | H | 4-isoxazolyl | CH₃ |
| 100 | H | 5-isoxazolyl | CH₃ |
| 101 | H | 2-oxazolyl | CH₃ |
| 102 | H | 4-oxazolyl | CH₃ |

The tables 73–108 below are based on the 2-benzoylcyclohexane-1,3-diones of the formula Id:

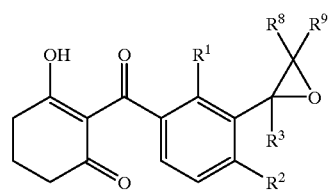

Table 73: Compounds 73.1–73.102

Compounds of the formula Id, where $R^1$ is chlorine, $R^2$ is methylsulfonyl, $R^{11}$, $R^{12}$, $R^{13}$, $R^{14}$, $R^{15}$ and $R^{16}$ are each hydrogen and where for each individual compound the substituents $R^3$ to $R^7$ each correspond to one line of Table C.

Table 74: Compounds 74.1–74.102

Compounds of the formula Id, where $R^1$ and $R^2$ are each chlorine, $R^{11}$, $R^{12}$, $R^{13}$, $R^{14}$, $R^{15}$ and $R^{16}$ are each hydrogen and where for each individual compound the substituents $R^3$ to $R^7$ each correspond to one line of Table C.

Table 75: Compounds 75.1–75.102

Compounds of the formula Id, where $R^1$ is chlorine, $R^2$ is trifluoromethyl, $R^{11}$, $R^{12}$, $R^{13}$, $R^{14}$, $R^{15}$ and $R^{16}$ are each hydrogen and where for each individual compound the substituents $R^3$ to $R^7$ each correspond to one line of Table C.

Table 76: Compounds 76.1–76.102

Compounds of the formula Id, where $R^1$ is methyl, $R^2$ is chlorine, $R^{11}$, $R^{12}$, $R^{13}$, $R^{14}$, $R^{15}$ and $R^{16}$ are each hydrogen and where for each individual compound the substituents $R^3$ to $R^7$ each correspond to one line of Table C.

Table 77: Compounds 77.1–77.102

Compounds of the formula Id, where $R^1$ is methyl, $R^2$ is methylsulfonyl, $R^{11}$, $R^{12}$, $R^{13}$, $R^{14}$, $R^{15}$ and $R^{16}$ are each hydrogen and where for each individual compound the substituents $R^3$ to $R^7$ each correspond to one line of Table C.

Table 78: Compounds 78.1–78.102

Compounds of the formula Id, where $R^1$ is methyl, $R^2$ is trifluoromethyl, $R^{11}$, $R^{12}$, $R^{13}$, $R^{14}$, $R^{15}$ and $R^{16}$ are each hydrogen and where for each individual compound the substituents $R^3$ to $R^7$ each correspond to one line of Table C.

Table 79: Compounds 79.1–79.102

Compounds of the formula Id, where $R^1$ is chlorine, $R^2$ is methylsulfonyl, $R^{11}$, $R^{12}$, $R^{15}$ and $R^{16}$ are each hydrogen, $R^{13}$ and $R^{14}$ are each methyl and where for each individual compound the substituents $R^3$ to $R^7$ each correspond to one line of Table C.

Table 80: Compounds 80.1–80.102

Compounds of the formula Id, where $R^1$ and $R^2$ are each chlorine, $R^{11}$, $R^{12}$, $R^{15}$ and $R^{16}$ are each hydrogen, $R^{13}$ and $R^{14}$ are each methyl and where for each individual compound the substituents $R^3$ to $R^7$ each correspond to one line of Table C.

Table 81: Compounds 81.1–81.102

Compounds of the formula Id, where $R^1$ is chlorine, $R^2$ is trifluoromethyl, $R^{11}$, $R^{12}$, $R^{15}$ and $R^{16}$ are each hydrogen, $R^{13}$ and $R^{14}$ are each methyl and where for each individual compound the substituents $R^3$ to $R^7$ each correspond to one line of Table C.

Table 82: Compounds 82.1–82.102

Compounds of the formula Id, where $R^1$ is methyl, $R^2$ is chlorine, $R^{11}$, $R^{12}$, $R^{15}$ and $R^{16}$ are each hydrogen, $R^{13}$ and $R^{14}$ are each methyl and where for each individual compound the substituents $R^3$ to $R^7$ each correspond to one line of Table C.

Table 83: Compounds 83.1–83.102

Compounds of the formula Id, where $R^1$ is methyl, $R^2$ is methylsulfonyl, $R^{11}$, $R^{12}$, $R^{15}$ and $R^{16}$ are each hydrogen, $R^{13}$ and $R^{14}$ are each methyl and where for each individual compound the substituents $R^3$ to $R^7$ each correspond to one line of Table C.

Table 84: Compounds 84.1–84.102

Compounds of the formula Id, where $R^1$ is methyl, $R^2$ is trifluoromethyl, $R^{11}$, $R^{12}$, $R^{15}$ and $R^{16}$ are each hydrogen, $R^{13}$ and $R^{14}$ are each methyl and where for each individual compound the substituents $R^3$ to $R^7$ each correspond to one line of Table C.

Table 85: Compounds 85.1–85.102

Compounds of the formula Id, where $R^1$ is chlorine, $R^2$ is methylsulfonyl, $R^{11}$, $R^{12}$, $R^{13}$ and $R^{14}$ are each hydrogen, $R^{15}$ and $R^{16}$ are each methyl and where for each individual compound the substituents $R^3$ to $R^7$ each correspond to one line of Table C.

Table 86: Compounds 86.1–86.102

Compounds of the formula Id, where $R^1$ and $R^2$ are each chlorine, $R^{11}$, $R^{12}$, $R^{13}$ and $R^{14}$ are each hydrogen, $R^{15}$ and $R^{16}$ are each methyl and where for each individual compound the substituents $R^3$ to $R^7$ each correspond to one line of Table C.

Table 87: Compounds 87.1–87.102

Compounds of the formula Id, where $R^1$ is chlorine, $R^2$ is trifluoromethyl, $R^{11}$, $R^{12}$, $R^{13}$ and $R^{14}$ are each hydrogen, $R^{15}$ and $R^{16}$ are each methyl and where for each individual compound the substituents $R^3$ to $R^7$ each correspond to one line of Table C.

Table 88: Compounds 88.1–88.102

Compounds of the formula Id, where $R^1$ is methyl, $R^2$ is chlorine, $R^{11}$, $R^{12}$, $R^{13}$ and $R^{14}$ are each hydrogen, $R^{15}$ and $R^{16}$ are each methyl and where for each individual compound the substituents $R^3$ to $R^7$ each correspond to one line of Table C.

Table 89: Compounds 89.1–89.102

Compounds of the formula Id, where $R^1$ is methyl, $R^2$ is methylsulfonyl, $R^{11}$, $R^{12}$, $R^{13}$ and $R^{14}$ are each hydrogen, $R^{15}$ and $R^{16}$ are each methyl and where for each individual compound the substituents $R^3$ to $R^7$ each correspond to one line of Table C.

Table 90: Compounds 90.1–90.102

Compounds of the formula Id, where $R^1$ is methyl, $R^2$ is trifluoromethyl, $R^{11}$, $R^{12}$, $R^{13}$ and $R^{14}$ are each hydrogen, $R^{15}$ and $R^{16}$ are each methyl and where for each individual compound the substituents $R^3$ to $R^7$ each correspond to one line of Table C.

Table 91: Compounds 91.1–91.102

Compounds of the formula Id, where $R^1$ is chlorine, $R^2$ is methylsulfonyl, $R^{11}$, $R^{12}$ $R^{15}$ and $R^{16}$ are each methyl, the $CR^{13}R^{14}$ unit forms a group C=O and where for each individual compound the substituents $R^3$ to $R^7$ each correspond to one line of Table C.

Table 92: Compounds 92.1–92.102

Compounds of the formula Id, where $R^1$ and $R^2$ are each chlorine, $R^{11}$, $R^{12}$, $R^{15}$ and $R^{16}$ are each methyl, the $CR^{13}R^{14}$ unit forms a group C=O and where for each individual compound the substituents $R^3$ to $R^7$ each correspond to one line of Table C.

Table 93: Compounds 93.1–93.102

Compounds of the formula Id, where $R^1$ is chlorine, $R^2$ is trifluoromethyl, $R^{11}$, $R^{12}$, $R^{15}$ and $R^{16}$ are each methyl, the $CR^{13}R^{14}$ unit forms a group C=O and where for each individual compound the substituents $R^3$ to $R^7$ each correspond to one line of Table C.

Table 94: Compounds 94.1–94.102

Compounds of the formula Id, where $R^1$ is methyl, $R^2$ is chlorine, $R^{11}$, $R^{12}$, $R^{15}$ and $R^{16}$ are each methyl, the $CR^{13}R^{14}$ unit forms a group C=O and where for each individual compound the substituents $R^3$ to $R^7$ each correspond to one line of Table C.

Table 95: Compounds 95.1–95.102

Compounds of the formula Id, where $R^1$ is methyl, $R^2$ is methylsulfonyl, $R^{11}$, $R^{12}$, $R^{15}$ and $R^{16}$ are each methyl, the $CR^{13}R^{14}$ unit forms a group C=O and where for each individual compound the substituents $R^3$ to $R^7$ each correspond to one line of Table C.

Table 96: Compounds 96.1–96.102

Compounds of the formula Id, where $R^1$ is methyl, $R^2$ is trifluoromethyl, $R^{11}$, $R^{12}$, $R^{15}$ and $R^{16}$ are each methyl, the $CR^{13}R^{14}$ unit forms a group C=O and where for each individual compound the substituents $R^3$ to $R^7$ each correspond to one line of Table C.

Table 97: Compounds 97.1–97.102

Compounds of the formula Id, where $R^1$ is methylsulfonyl, $R^{11}$, $R^{12}$, $R^{13}$, $R^{15}$ and $R^{16}$ are each hydrogen, $R^{14}$ is methyl and where for each individual compound the substituents $R^3$ to $R^7$ each correspond to one line of Table C.

Table 98: Compounds 98.1–98.102

Compounds of the formula Id, where $R^1$ and $R^2$ are each chlorine, $R^{11}$, $R^{12}$, $R^{13}$, $R^{15}$ and $R^{16}$ are each hydrogen, $R^{14}$ is methyl and where for each individual compound the substituents $R^3$ to $R^7$ each correspond to one line of Table C.

Table 99: Compounds 99.1–99.102

Compounds of the formula Id, where $R^1$ is chlorine, $R^2$ is trifluoromethyl, $R^{11}$, $R^{12}$, $R^{13}$, $R^{15}$ and $R^{16}$ are each hydrogen, $R^{14}$ is methyl and where for each individual compound the substituents $R^3$ to $R^7$ each correspond to one line of Table C.

Table 100: Compounds 100.1–100.102

Compounds of the formula Id, where $R^1$ is methyl, $R^2$ is chlorine, $R^{11}$, $R^{12}$, $R^{13}$, $R^{15}$ and $R^{16}$ are each hydrogen, $R^{14}$ is methyl and where for each individual compound the substituents $R^3$ to $R^7$ each correspond to one line of Table C.

Table 101: Compounds 101.1–101.102

Compounds of the formula Id, where $R^1$ is methyl, $R^2$ is methylsulfonyl, $R^{11}$, $R^{12}$, $R^{13}$, $R^{15}$ and $R^{16}$ are each hydrogen, $R^{14}$ is methyl and where for each individual compound the substituents $R^3$ to $R^7$ each correspond to one line of Table C.

Table 102: Compounds 102.1–102.102

Compounds of the formula Id, where $R^1$ is methyl, $R^2$ is trifluoromethyl, $R^{11}$, $R^{12}$, $R^{13}$, $R^{15}$ and $R^{16}$ are each hydrogen, $R^{14}$ is methyl and where for each individual compound the substituents $R^3$ to $R^7$ each correspond to one line of Table C.

Table 103: Compounds 103.1–103.102

Compounds of the formula Id, where $R^1$ is chlorine, $R^2$ is methylsulfonyl, $R^{11}$, $R^{12}$, $R^{14}$ and $R^{15}$ are each hydrogen, $R^{13}$ and $R^{16}$ together form a methylene group and where for each individual compound the substituents $R^3$ to $R^7$ each correspond to one line of Table C.

Table 104: Compounds 104.1–104.102

Compounds of the formula Id, where $R^1$ and $R^2$ are each chlorine, $R^{11}$, $R^{12}$, $R^{14}$ and $R^{15}$ are each hydrogen, $R^{13}$ and $R^{16}$ together form a methylene group and where for each individual compound the substituents $R^3$ to $R^7$ each correspond to one line of Table C.

Table 105: Compounds 105.1–105.102

Compounds of the formula Id, where $R^1$ is chlorine, $R^2$ is trifluoromethyl, $R^{11}$, $R^{12}$, $R^{14}$ and $R^{15}$ are each hydrogen, $R^{13}$ and $R^{16}$ together form a methylene group and where for each individual compound the substituents $R^3$ to $R^7$ each correspond to one line of Table C.

Table 106: Compounds 106.1–106.102

Compounds of the formula Id, where $R^1$ is methyl, $R^2$ is chlorine, $R^{11}$, $R^{12}$, $R^{14}$ and $R^{15}$ are each hydrogen, $R^{13}$ and $R^{16}$ together form a methylene group and where for each individual compound the substituents $R^3$ to $R^7$ each correspond to one line of Table C.

Table 107: Compounds 107.1–107.102

Compounds of the formula Id, where $R^1$ is methyl, $R^2$ is methylsulfonyl, $R^{11}$, $R^{12}$, $R^{14}$ and $R^{15}$ are each hydrogen, $R^{13}$ and $R^{16}$ together form a methylene group and where for each individual compound the substituents $R^3$ to $R^7$ each correspond to one line of Table C.

Table 108: Compounds 108.1–108.102

Compounds of the formula Id, where $R^1$ is methyl, $R^2$ is trifluoromethyl, $R^{11}$, $R^{12}$, $R^{14}$ and $R^{15}$ are each hydrogen, $R^{13}$ and $R^{16}$ together form a methylene group and where for each individual compound the substituents $R^3$ to $R^7$ each correspond to one line of Table C.

The compounds I and their agriculturally useful salts are suitable, both in the form of isomer mixtures and in the form of the pure isomers, as herbicides. The herbicidal compositions comprising I control vegetation on non-crop areas very efficiently, especially at high rates of application. They act against broad-leaved weeds and grass weeds in crops such as wheat, rice, maize, soybean and cotton without causing any significant damage to the crop plants. This effect is mainly observed at low rates of application.

Depending on the application method used, the compounds I, or the compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus var. napus, Brassica napus var. napobrassica, Brassica rapa var. silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N.rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylestre* [sic], *Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays.*

In addition, the compounds I may also be used in crops which tolerate the action of herbicides owing to breeding, including genetic engineering methods.

The herbicidal compositions or the active compounds can be applied pre- or post-emergence. If the active compounds are less well tolerated by certain crop plants, application techniques may be used in which the herbicidal compositions are sprayed, with the aid of the spraying equipment, in such a way that they come into contact as little as possible, if at all, with the leaves of the sensitive crop plants, while the active compounds reach the leaves of undesirable plants growing underneath, or the bare soil surface (post-directed, lay-by).

The compounds I, or the herbicidal compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for broadcasting, or granules, by means of spraying, atomizing, dusting, broadcasting or watering. The use forms depend on the intended aims; in any case, they should guarantee a very fine distribution of the active compounds according to the invention.

Essentially, suitable inert auxiliaries include: mineral oil fractions of medium to high boiling point, such as kerosene and diesel oil, furthermore coal tar oils and oils of vegetable or animal origin, aliphatic, cyclic and aromatic hydrocarbons, eg. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, or strongly polar solvents, eg. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the substituted 2-benzoylcyclohexane-1,3-diones, either as such or dissolved in an oil or solvent, can be homogenized in water by means of a wetting agent, tackifier, dispersant or emulsifier. Alternatively, it is possible to prepare concentrates comprising active compound, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for broadcasting and dusts can be prepared by mixing or grinding the active compounds together with a solid carrier.

Granules, eg. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentrations of the active compounds I in the ready-to-use preparations can be varied within wide ranges. In general, the formulations comprise from 0.001 to 98% by weight, preferably 0.01 to 95% by weight of at least one active compound. The active compounds are employed in a purity of from 90% to 100%, preferably 90% [sic] to 100% (according to the NMR spectrum). The compounds I according to the invention can be formulated for example as follows:

I 20 parts by weight of the compound No. 110.1 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II 20 parts by weight of the compound No. 110.1 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III 20 parts by weight of the active compound No. 110.1 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV 20 parts by weight of the active compound No. 110.1 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V 3 parts by weight of the active compound No. 110.1 are mixed with 97 parts by weight of finely divided kaolin. This gives a dust which comprises 3% by weight of active compound.

VI 20 parts by weight of the active compound No. 110.1 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII 1 part by weight of the compound No. 110.1 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII 1 part by weight of the compound No. 110.1 is dissolved in a mixture composed of 80 parts by weight of cyclohexanone and 20 parts by weight of Wettol® EM 31 (nonionic emulsifier based on ethoxylated castor oil). This gives a stable emulsion concentrate.

To widen the activity spectrum and to achieve synergistic effects, the substituted 2-benzoylcyclohexane-1,3-diones I may be mixed with a large number of representatives of other herbicidal or growth-regulating active compound groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-aroyl-1,3-cyclohexanediones, hetarylaryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or else concomitantly in combination with other herbicides, even in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

The active compound application rates are from 0.001 to 3.0, preferably 0.01 to 1.0 kg/ha of active substance (a.s.), depending on the control target, the season, the target plants and the growth stage.

The syntheses of some starting materials are given below:
2,4-dichloro-3-(3'-hydroxy-3'-methyl-2'-oxetanyl)benzoic acid (Compound 5.03)
Step a: Methyl 2,4-dichloro-3-(3'-trimethylsilyloxy-3'-methyl-2'-oxetanyl)benzoate (Compound 5.01)

A solution of 10 g (0.043 mol) of methyl 2,4-dichloro-3-formylbenzoate and 8.4 g (0.065 mol) of 2-trimethylsilyloxypropene in 1.0 l of n-hexane was irradiated at room temperature with a UV radiator (Heraeus, TQ 150W) for 24 h. The solvent was subsequently distilled off under reduced pressure and the residue was purified over 100 g of silica gel (0.04–0.06 mm) using mixtures of cyclohexane and ethyl acetate of from 100:1 to 5:1 (v/v). 6.8 g of methyl 2,4-dichloro-3-(3'-trimethylsilyloxy-3'-methyl-2'-oxetanyl)benzoate were obtained.

1H NMR (CDCl$_3$) δ [ppm]: 1.3 (t, 3H), 3.9 (dd, 3H), 4.6 (m, 2H), 6.4 (d, 1H), 7.0 (s, 1H), 7.3 (m, 2H).

Step b: Methyl 2,4-dichloro-3-(3'-hydroxy-3'-methyl-2'-oxetanyl)benzoate (Compound 5.02)

A solution of 14 g (0.039 mol) of methyl 2,4-dichloro-3-(3'-trimethylsilyloxy-3'-methyl-2'-oxetanyl)benzoate and 14 g of ion exchanger (Dowex 50 WX2, Serva) was stirred in 100 ml of methanol at room temperature for 12 h. The solvent was subsequently distilled off under reduced pressure and the residue was purified over 100 g of silica gel (0.04–0.06 mm) using mixtures of cyclohexane and ethyl acetate of from 100:1 to 2:1 (v/v). 6.1 g of methyl 2,4-dichloro-3-(3'-hydroxy-3'-methyl-2'-oxetanyl)benzoate were obtained.

1H NMR (CDCl$_3$) δ [ppm]: 1.7 (s, 3H), 3.9 (s, 3H), 4.6 (d, 1H), 4.8 (d, 1H), 6.3 (s, 1H), 7.4 (d, 1H), 7.6 (d, 1H).

alternatively:

Step c: Methyl 2,4-dichloro-3-(3'-hydroxy-3'-methyl-2'-oxetanyl)benzoate (Compound 5.02)

A solution of 1 g (0.003 mol) of methyl 2,4-dichloro-3-(3'-trimethylsilyloxy-3'-methyl-2'-oxetanyl)benzoate and 5 ml of a 10% strength methanolic solution of hydrogen chloride was stirred in 30 ml of methanol at room temperature for 12 h. The solvent was subsequently distilled off under reduced pressure and the residue was taken up in diethyl ether. This ether solution was washed neutral with water, dried with sodium sulfate and filtered and the solvent was distilled off under reduced pressure. 0.7 g of methyl 2,4-dichloro-3-(3'-hydroxy-3'-methyl-2'-oxetanyl)benzoate was obtained.

1H NMR (CDCl$_3$) δ [ppm]: 1.7 (s, 3H), 3.9 (s, 3H), 4.6 (d, 1H), 4.8 (d, 1H), 6.3 (s, 1H), 7.4 (d, 1H), 7.6 (d, 1H).

Step d: 2,4-Dichloro-3-(3'-hydroxy-3'-methyl-2'-oxetanyl)benzoic acid (Compound 5.03)

A solution of 4.9 g (0.013 mol) of methyl 2,4-dichloro-3-(3'-hydroxy-3'-methyl-2'-oxetanyl)benzoate and 0.5 g (0.020 mol) of lithium hydroxide was stirred at 0° C. in a mixture of 20 ml of tetrahydrofuran and 20 ml of water for 12 h. The solution was subsequently adjusted to pH 1–2 using 10% strength aqueous hydrochloric acid and extracted with diethyl ether. The combined organic phases were subsequently dried with sodium sulfate and filtered and the solvent was distilled off under reduced pressure. 3.5 g of 2,4-dichloro-3-(3'-hydroxy-3'-methyl-2'-oxetanyl)benzoic acid were obtained.

1H-NMR (CDCl$_3$) δ [ppm]: 2.5 (s, 3H), 4.7 (d, 1H), 4.9 (d, 1H), 6.4 (s. 1H), 7.4 (d, 1H), 7.7 (d, 1H), 8.6 (broad s, 1H).

In addition to the above compounds, further benzoic acid derivatives of the formula Vd which were prepared or are preparable in a similar manner are listed in Table 109 below.

TABLE 109

Vd

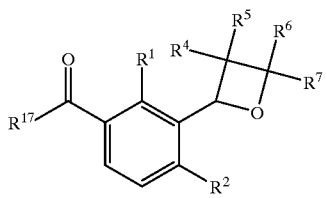

| No. | R$^1$ | R$^2$ | R$^4$ | R$^5$ | R$^6$ | R$^7$ | R$^{17}$ | 1 NMR [sic] [ppm] |
|---|---|---|---|---|---|---|---|---|
| 109.1 | Cl | Cl | —C(CH$_3$)$_3$ | —OSi(CH$_3$)$_3$ | H | H | —OCH$_3$ | 0.1(s, 9H), 1.2(s, 12H), 4.0(s, 3H), 4.7(d, 1H), 5.1(d, 1H), 6.5(s, 1H), 7.4(d, 1H), 7.6(d, 1H) |
| 109.2 | Cl | Cl | —C(CH$_3$)$_3$ | —OH | H | H | —OCH$_3$ | 1.2(s, 12H), 4.0(s, 3H), 4.6(d, 1H), 5.1(d, 1H), 6.4(s, 1H), 7.3(d, 1H), 7.6(d, 1H) |
| 109.3 | Cl | Cl | —C(CH$_3$)$_3$ | —OH | H | H | —OH | 0.9(s, 12H), 4.5(d, 1H), 4.7(d, 1H), 6.4(s, 1H), 7.2 (d, 1H), 7.5(d, 1H) |
| 109.4 | Cl | Cl | H | —CH$_2$CH$_2$O— | H | H | —OCH$_3$ | 2.3(m, 2H), 3.6(m, 2H), 3.9(s, 3H), 4.4(d, 1H), 5.2 (m, 1H), 5.4(m, 1H), 6.1 (d, 1H), 7.3(d, 1H), 7.6(d, 1H) |
| 109.5 | Cl | Cl | H | —CH$_2$CH$_2$O— | H | H | —OH | |
| 109.6 | Cl | Cl | H | —CH$_2$CH$_2$CH$_2$O— | H | H | —OCH$_3$ | 1.6(m, 2H), 2.2(m, 2H), 3.8(m, H), 3.9(s, 3H), 4.9 (m, 1H), 6.1(d, 1H), 7.3(d, 1H), 7.5(d, 1H) |
| 109.7 | Cl | Cl | H | —CH$_2$CH$_2$CH$_2$O— | H | H | —OH | |

Preparation of the End Products 4-(2',4'-Dichloro-3'-(3"-hydroxy-3"-methyl-2"-oxetanylbenzoyl)-5,5-dimethyl-1,3-cyclohexanedione (compound 110.1)

A solution of 0.8 g (0.003 M [sic]) of 2,4-dichloro-3-(3'-hydroxy-3'-methyl-2'-oxetanyl)benzoic acid, 0,4 g (0,003 M [sic]) of 5,5-dimethyl-1,3-cyclohexanedione and 0.7 g (0.003 M [sic]) of dicyclohexylcarbodiimide in 40 ml of dry acetonitrile was stirred at room temperature for 12 h. The precipitate was then filtered off and the filtrate was then taken up in aqueous potassium carbonate solution. After extraction of the aqueous phase with ethyl acetate, the pH was adjusted to 2 using 10% strength aqueous hydrochloric acid, and the mixture was re-extracted with ethyl acetate. The combined organic phases were washed neutral with water, dried with sodium sulfate and filtered and the solvent was distilled off under reduced pressure. The residue was purified over 50 g of silica gel (0.04–0.06 mm) using mixtures of dichloromethane and methanol of from 100:1 to 10:1 (v/v). 0.2 g of 4-(2',4'-dichloro-3'-(3"-hydroxy-3"-methyl-2"-oxetanylbenzoyl)-5,5-dimethyl-1,3-cyclohexanedione was obtained.

Depending on the species, the plants were kept at 10–25° C. or 20–35° C. The test period extended over 2 to 4 weeks. During this time, the plants were tended, and their response to the individual treatments was evaluated.

The evaluation was carried out using a scale from 0 to 100. 100 means no emergence of the plants, or complete destruction of at least the aerial parts, and 0 means no damage, or normal course of growth.

The plants used in the greenhouse experiments belong to the following species:

TABLE 110

Ib

[Structure diagram of compound Ib with substituents $R^1$ through $R^{16}$]

| No. | $R^1$ | $R^2$ | $R^3$ | $R^4$ | $R^5$ | $R^6$ | $R^7$ | $R^{11}$ | $R^{12}$ | $R^{13}$ | $R^{14}$ | $R^{15}$ | $R^{16}$ | m.p. [° C.] | $^1$H-NMR (CDCl$_3$) δ [ppm] |
|---|---|---|---|---|---|---|---|---|---|---|---|---|---|---|---|
| 110.1 | Cl | Cl | H | CH$_3$ | OH | H | H | H | H | CH$_3$ | CH$_3$ | H | H | | 1.0(s, 6H), 2.2(m, 2H), 2.4(m, 2H), 3.4(s, 3H), 4.8(m, 2H), 6.2(d, 1H), 6.9(d, 1H), 7.3(m, 3H) |
| 110.2 | Cl | Cl | H | CH$_3$ | OH | H | H | H | H | H | H | CH$_3$ | CH$_3$ | 96 | / |
| 110.3 | Cl | Cl | H | CH$_3$ | OH | H | H | CH$_3$ | H | =O | | CH$_3$ | CH$_3$ | 154 | / |
| 110.4 | Cl | Cl | H | CH$_3$ | OH | H | H | H | H | H | H | H | H | 166 | / |
| 110.5 | Cl | Cl | H | C(CH$_3$)$_3$ | OH | H | H | H | H | CH$_3$ | CH$_3$ | H | H | 148 | / |
| 110.6 | Cl | Cl | H | C(CH$_3$)$_3$ | OH | H | H | CH$_3$ | CH$_3$ | =O | | CH$_3$ | CH$_3$ | 102 | / |
| 110.7 | Cl | Cl | H | H—OCH$_2$CH$_2$CH$_2$— | | | H | H | H | CH$_3$ | CH$_3$ | H | H | 60 | / |

Use Examples

The herbicidal activity of the substituted 2-benzoylcyclohexane-1,3-diones of the formula I was demonstrated by greenhouse experiments:

The culture containers used were plastic pots containing loamy sand with approximately 3.0% of humus as the substrate. The seeds of the test plants were sown separately for each species.

For the pre-emergence treatment, the active compounds, which had been suspended or emulsified in water, were applied directly after sowing by means of finely distributing nozzles. The containers were irrigated gently to promote germination and growth and subsequently covered with translucent plastic hoods until the plants had rooted. This cover caused uniform germination of the test plants, unless this was adversely affected by the active compounds.

For the post-emergence treatment, the test plants were first grown to a height of 3 to 15 cm, depending on the plant habit, and only then treated with the active compounds which had been suspended or emulsified in water. For this purpose, the test plants were either sown directly and grown in the same containers, or they were first grown separately as seedlings and transplanted into the test containers a few days prior to treatment. The application rate for the post-emergence treatment as 0.5 or 0.25 kg/ha of a.s.

| Scientific name | Common name | Abbreviation |
|---|---|---|
| Echinochloa crus-galli | barnyardgrass | ECHCG |
| Setaria viridis | green foxtail | SETVI |
| Chenopodium album | lambsquarters (goosefoot) | CHEAL |
| Polygonum persicaria | ladythumb | POLPE |
| Solanum nigrum | black nightshade | SOLNI |

TABLE 111

Herbicidal activity when applied by the post-emergence method in the greenhouse 110.1

[Structure of compound 110.1]

| Ex. No. | 110.1 | |
|---|---|---|
| Application rate (kg/ha of a.s.) | 0.5 | 0.25 |

TABLE 111-continued

Herbicidal activity when applied by the post-emergence method in the greenhouse 110.1

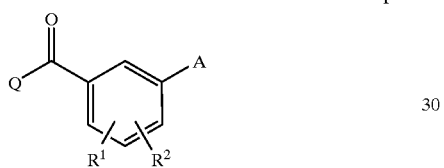

| Test plants | | |
|---|---|---|
| ECHCG | 90 | 90 |
| SETVI | 90 | 80 |
| CHEAL | 98 | 98 |
| POLPE | 95 | 95 |
| SOLNI | 100 | 95 |

We claim:

1. A 2-benzoylcyclohexane-1,3-dione of the formula I:

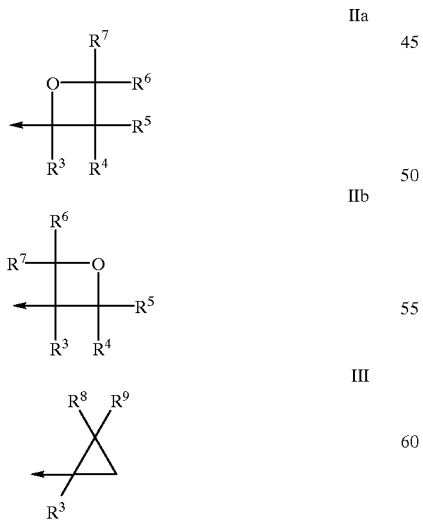

where:

$R^1$ and $R^2$ are each hydrogen, mercapto, nitro, halogen, cyano, thiocyanato, $C_1$–$C_6$-alkyl, $C_1$–$C_6$-haloalkyl, $C_1$–$C_6$-alkoxy, $C_1$–$C_6$-alkyl, $C_2$–$C_6$-alkenyl, $C_2$–$C_6$-alkynyl, —$OR^{10}$, —$OCOR^{10}$, —$OSO_2R^{10}$, —$S(O)_n R^{10}$, —$SO_2R^{10}$, —$SO_2NR^3R^{10}$, —$NR^{10}SO_2R^{10}$ or —$NR^{10}COR$;

Q is a cyclohexane-1,3-dione ring with or without substitution, which is attached in position 2;

A is a group of the formula IIa, IIb or III:

where:

$R^3$ is hydrogen, $C_1$–$C_6$-alkyl or phenyl, where the alkyl and phenyl radicals mentioned may be partially or fully halogenated and/or may carry one to three of the following groups: hydroxyl, mercapto, amino, cyano, $R^{10}$, —$OR^{10}$, —$SR^{10}$, —$NR^8R^{10}$, =$NOR^{10}$, —$OCOR^{10}$, —$SCOR^{10}$, —$NR^8COR^{10}$, —$CO_2R^{10}$, —$COSR^{10}$, —$CONR^8R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals mentioned may in turn be substituted;

$R^4$–$R^7$ may be identical or different and, independently of each other, are:

hydrogen, hydroxyl, mercapto, amino, halogen, $C_1$–$C_6$-alkyl, $C_3$–$C_6$-cycloalkyl, phenyl, —$OR^{10}$, —$S(O)_n R^{10}$, —$OS(O)_n R^{10}$, —$PO(OR^{10})_2$, —$NR^3R^{10}$, —$Si(R^{10})_3$ or —$OCOR^{10}$, where the alkyl and cycloalkyl radicals mentioned and $R^3$ and $R^{10}$ of the radicals —$OR^{10}$, —$S(O)_n R^{10}$, —$OS(O)_n R^{10}$, —$PO(OR^{10})_2$, —$NR^3R^{10}$, —$Si(R^{10})_3$, —$OCOR^{10}$ may be partially or fully halogenated and/or may carry one to three of the following groups:

hydroxyl, mercapto, amino, cyano, $R^{10}$, —$OR^{10}$, —$SR^{10}$, —$NR^8R^{10}$, =$NOR^{10}$, —$OCOR^{10}$, —$SCOR^{10}$, —$NR^8COR^{10}$, —$CO_2R^{10}$, —$COSR^{10}$, —$CONR^8R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals mentioned may in turn be substituted;

$R^4$ and $R^5$ together may form a $C_2$–$C_5$-alkylene or $C_2$–$C_5$-alkenylene chain which may be interrupted once or twice by a nitrogen or an oxygen atom, or may form a group =X, where X is an oxygen atom or a group $CR^3R^{10}$, $NR^{10}$ or $NOR^{10}$;

$R^6$ and $R^7$ together may form a $C_2$–$C_5$-alkylene or $C_2$–$C_5$-alkenylene chain which may be interrupted once or twice by a nitrogen or an oxygen atom, or may form a group =X, where X is an oxygen atom or a group $CR^3R^{10}$, $NR^{10}$ or $NOR^{10}$;

n is zero, one or two;

$R^5$ and $R^6$ together may furthermore, if they are attached to adjacent carbon atoms and if $R^4$ and $R^7$ are each hydrogen, form a $C_3$–$C_4$-alkylene or $C_3$–$C_4$-alkenylene chain which may be interrupted by a nitrogen or an oxygen atom;

$R^8$ and $R^9$ may be identical or different and, independently of each other, are:

hydrogen, nitro, halogen, cyano, $C_1$–$C_6$-alkyl, $C_3$–$C_6$-cycloalkyl, $C_5$–$C_6$-heterocyclyl, —$OR^{10}$, —$SR^{10}$, —$COR^{10}$, —$COOR^{10}$, —$CONR^3R^{10}$, phenyl, phenyl-$C_1$–$C_6$-alkyl and five- or six-membered hetaryl, where the alkyl and cycloalkyl radicals mentioned and $R^3$ and $R^{10}$ of the radicals —$OR^{10}$, —$SR^{10}$, —$COR^{10}$, —$COOR^{10}$, —$CONR^3R^{10}$ may be partially or fully halogenated and/or may carry one to three of the following groups:

hydroxyl, mercapto, amino, cyano, $R^{10}$, —$OR^{10}$, —$SR^{10}$, —$NR^8R^{10}$, =$NOR^{10}$, —$OCOR^{10}$, —$SCOR^{10}$, —$NR^8COR^{10}$, —$CO_2R^{10}$, —$COSR^{10}$, —$CONR^8R^{10}$, $C_1$–$C_4$- alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals mentioned may in turn be substituted;

$R^8$ and $R^9$ together may furthermore form a $C_2$–$C_5$-alkylene or $C_2$–$C_5$-alkenylene chain which may be interrupted once or twice by a nitrogen or an oxygen atom;

$R^{10}$ is hydrogen, $C_1$–$C_6$-alkyl, $C_1$–$C_6$-haloalkyl, $C_2$–$C_6$-alkenyl, $C_2$–$C_6$-alkynyl, phenyl or phenyl-$C_1$–$C_6$-alkyl; where the alkyl radicals mentioned may be partially or fully halogenated and/or may carry one to three of the following groups:

hydroxyl, mercapto, amino, cyano, $R^{10}$, —$OR^{10}$, —$SR^{10}$, —$NR^3R^{10}$, =$NOR^{10}$, —$OCOR^{10}$, —$SCOR^{10}$, —$NR^3COR^{10}$, —$CO_2R^{10}$, —$COSR^{10}$, —$CONR^3R^{10}$, $C_1$–$C_4$-alkyliminooxy, $C_1$–$C_4$-alkoxyamino, $C_1$–$C_4$-alkylcarbonyl, $C_1$–$C_4$-alkoxy-$C_2$–$C_6$-alkoxycarbonyl, $C_1$–$C_4$-alkylsulfonyl, heterocyclyl, heterocyclyloxy, phenyl, benzyl, hetaryl, phenoxy, benzyloxy and hetaryloxy, where the last eight radicals mentioned may in turn be substituted;

and agriculturally useful salts thereof.

2. A 2-benzoylcyclohexane-1,3-dione of the formula I as claimed in claim 1 in which Q is a cyclohexane-1,3-dione ring of the formula IV:

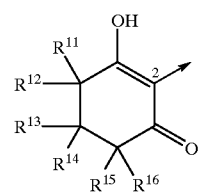

IV which is attached in position 2, where $R^{11}$, $R^{12}$, $R^{14}$ and $R^{16}$ are each hydrogen or $C_1$–$C_4$-alkyl;

$R^{13}$ is hydrogen, $C_1$–$C_4$-alkyl or $C_3$–$C_4$-cycloalkyl, where the last two groups mentioned may carry one to three of the following substituents:

halogen, $C_1$–$C_4$-alkylthio or $C_1$–$C_4$-alkoxy;

or is tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, where the last 6 radicals mentioned may be substituted by one to three $C_1$–$C_4$-alkyl radicals;

$R^{15}$ is hydrogen, $C_1$–$C_4$-alkyl or $C_1$–$C_6$-alkoxycarbonyl;

or $R^{13}$ and $R^{16}$ together form a $\pi$ bond or a three- to six-membered carbocyclic ring;

or the $CR^{13}R^{14}$ unit may be replaced by C=O.

3. A 2-benzoylcyclohexane-1,3-dione of the formula I as claimed in claim 1 which:

$R^1$ is nitro, halogen, cyano, thiocyanato, $C_1$–$C_6$-alkyl, $C_1$–$C_6$-haloalkyl, $C_1$–$C_6$-alkoxy-$C_1$–$C_6$-alkyl, $C_2$–$C_6$-alkenyl, $C_2$–$C_6$-alkynyl, —$OR^5$ or —$S(O)_nR^7$;

$R^2$ is hydrogen or one of the radicals mentioned above under $R^1$.

4. A 2-benzoylcyclohexane-1,3-dione of the formula Ia as claimed in claim 1,

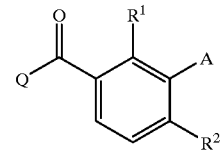

Ia where the substituents $R^1$, $R^2$, Q and A are each as defined in claim 1.

5. A 2-benzoylcyclohexane-1,3-dione of the formula Ia as claimed in claim 3 in which A is a group of the formula IIa or IIb.

6. A 2-benzoylcyclohexane-1,3-dione of the formula Ia as claimed in claim 3 in which A is a group of the formula III.

7. A process for preparing the 2-benzoylcyclohexane-1,3-dione of the formula I as claimed in claim 1, which comprises acylating a cyclohexane-1,3-dione Q with or without substitution with an activated carboxylic acid Va or with a carboxylic acid Vb:

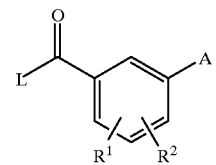

Va

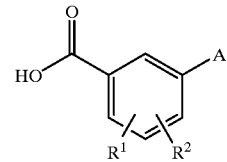

Vb where the substituents $R^1$, $R^2$ and A are each as defined under claim 1 and L is a nucleophilically exchangeable leaving group, and rearranging the acylation product, if appropriate in the presence of a catalyst, to give the compounds I.

8. A composition, which comprises a herbicidally active amount of at least one compound of the formula I or an agriculturally useful salt of I as claimed in claim 1 and auxiliaries which are customarily used for formulating crop protection agents.

9. A process for preparing herbicidally active compositions as claimed in claim 8, which comprises mixing a herbicidally effective amount of at least one compound of the formula I or an agriculturally useful salt of I as claimed in claim 1 and auxiliaries which are customarily used for formulating crop protection agents.

10. A method for controlling undesirable vegetation, which comprises allowing a herbicidally effective amount of at least one compound of the formula I or an agriculturally useful salt of I as claimed in claim 1 to act on plants, their habitat and/or on seeds.

11. A method of using the compounds of the formula I and agriculturally useful salts thereof as claimed in claim 1 as herbicides.

* * * * *